US008759027B2

(12) United States Patent
Zamost et al.

(10) Patent No.: US 8,759,027 B2
(45) Date of Patent: *Jun. 24, 2014

(54) PRODUCTION AND PURIFICATION OF IL-29

(71) Applicant: ZymoGenetics, Inc., Princeton, NJ (US)

(72) Inventors: Bruce L. Zamost, Seattle, WA (US);
Geoffrey F. Lee, Mercer Island, WA (US); Robert M. Dedinsky, Shoreline, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/720,363

(22) Filed: Dec. 19, 2012

(65) Prior Publication Data

US 2013/0143270 A1 Jun. 6, 2013

Related U.S. Application Data

(60) Division of application No. 13/488,840, filed on Jun. 5, 2012, now abandoned, which is a division of application No. 13/114,566, filed on May 24, 2011, now Pat. No. 8,211,670, which is a division of application No. 12/701,358, filed on Feb. 5, 2010, now Pat. No. 7,968,315, which is a division of application No. 12/537,935, filed on Aug. 7, 2009, now Pat. No. 7,759,092, which is a continuation of application No. 11/538,688, filed on Oct. 4, 2006, now abandoned.

(60) Provisional application No. 60/723,544, filed on Oct. 4, 2005.

(51) Int. Cl.
*C12N 15/24* (2006.01)
*C12P 21/02* (2006.01)
*C07K 14/54* (2006.01)

(52) U.S. Cl.
USPC ............... 435/69.52; 435/70.1; 530/412

(58) Field of Classification Search
CPC ........... C12P 21/02; A61K 38/20; C07K 1/14
USPC ................ 435/69.52, 70.1; 530/412
See application file for complete search history.

(56) References Cited

U.S. PATENT DOCUMENTS

| 5,710,027 | A  | 1/1998 | Hauptmann et al. |
|---|---|---|---|
| 6,927,040 | B2 | 8/2005 | Sheppard et al. |
| 7,038,032 | B2 | 5/2006 | Sheppard et al. |
| 7,135,170 | B2 | 11/2006 | Klucher et al. |
| 7,157,559 | B2 | 1/2007 | Brady et al. |
| 7,241,870 | B2 | 7/2007 | Sheppard et al. |
| 7,250,274 | B2 | 7/2007 | Chan et al. |
| 7,252,969 | B2 | 8/2007 | Sheppard et al. |
| 7,253,261 | B2 | 8/2007 | Sheppard et al. |
| 7,351,689 | B2 | 4/2008 | Doyle et al. |
| 7,445,773 | B2 | 11/2008 | Sheppard et al. |
| 7,445,913 | B2 | 11/2008 | Sheppard et al. |
| 7,446,172 | B2 | 11/2008 | Sheppard et al. |
| 7,455,993 | B2 | 11/2008 | Sheppard et al. |
| 7,462,467 | B2 | 12/2008 | Sheppard et al. |
| 7,468,423 | B2 | 12/2008 | Brady et al. |
| 7,479,542 | B2 | 1/2009 | Brady et al. |
| 7,485,699 | B2 | 2/2009 | Sheppard et al. |
| 7,485,700 | B2 | 2/2009 | Sheppard et al. |
| 7,485,701 | B2 | 2/2009 | Brady et al. |
| 7,485,702 | B2 | 2/2009 | Brady et al. |
| 7,495,077 | B2 | 2/2009 | Brady et al. |
| 7,495,078 | B2 | 2/2009 | Brady et al. |
| 7,495,079 | B2 | 2/2009 | Brady et al. |
| 7,498,154 | B2 | 3/2009 | Sheppard et al. |
| 7,514,536 | B2 | 4/2009 | Brady et al. |
| 7,517,961 | B2 | 4/2009 | Brady et al. |
| 7,544,779 | B2 | 6/2009 | Brady et al. |
| 7,582,450 | B2 | 9/2009 | Brady et al. |
| 7,588,918 | B2 | 9/2009 | Brady et al. |
| 7,588,919 | B2 | 9/2009 | Brady et al. |
| 7,595,174 | B2 | 9/2009 | Brady et al. |
| 7,608,427 | B2 | 10/2009 | Brady et al. |
| 7,608,428 | B2 | 10/2009 | Brady et al. |
| 7,622,561 | B2 | 11/2009 | Zamost et al. |
| 7,629,148 | B2 | 12/2009 | Brady et al. |
| 7,629,149 | B2 | 12/2009 | Brady et al. |
| 7,638,305 | B2 | 12/2009 | Brady et al. |
| 7,655,222 | B2 | 2/2010 | Sheppard et al. |
| 7,655,223 | B2 | 2/2010 | Sheppard et al. |
| 7,662,589 | B2 | 2/2010 | Brady et al. |
| 7,662,590 | B2 | 2/2010 | Brady et al. |

(Continued)

FOREIGN PATENT DOCUMENTS

| CN | 1 670 033 | 9/2005 |
|---|---|---|
| JP | 7-135992 | 5/1995 |
| WO | WO 2004/055168 | 7/2004 |
| WO | WO 2005/023862 | 3/2005 |

OTHER PUBLICATIONS

Li et al., "Purification and characterization of recombinant human interleukin-29 expressed in *Escherichia coli*," Journal of Biotechnology, 122(3): 334-340, 2006.
Sheppard et al., "IL-28, Il-29 and their class II cytokine receptor IL-28R," Nature Immunology 4(1):63-68, 2003.
Ogata et al., "Protection against bacteriophage contamination in industrial fermentation processes—Investigation and applications of phage resistance mechanisms in bacteria," Virus, (50)1, pp. 17-26, Jun. 2000.
Endriβ et al., "Loop Deletions Indicate Regions Important for FhuA Transport and Receptor Functions in *Escherichia coli*," Journal of Bacteriology, (186)14, pp. 4818-4823, Jul. 2004.
Sheppard, U.S. Appl. No. 12/352,454, filed Jan. 12, 2009.
Ge, Francis, et al, "PEGylation of cytokines and other therapeutic proteins and peptides: the importance of biological optimisation of coupling techniques", Bibliographic Details: International Journal of Hematology; Jul. 1998; vol. 68(1); pp. 1-18; PMID: 9713164.

(Continued)

*Primary Examiner* — Ruixiang Li
(74) *Attorney, Agent, or Firm* — Bing Hai

(57) ABSTRACT

The expression vectors and methods using an *E. coli* expression system for the large scale production of IL-29 are described. The vectors utilize the IL-29 coding sequence with specific changes in nucleotides in order to optimize codons and mRNA secondary structure for translation in *E. coli*. Also included are methods of producing, purifying and pegylating an IL-29 polypeptide.

20 Claims, No Drawings

(56) References Cited

U.S. PATENT DOCUMENTS

| | | |
|---|---|---|
| 7,662,927 B2 | 2/2010 | Sheppard et al. |
| 7,968,315 B2 | 6/2011 | Zamost et al. |
| 8,211,670 B2 | 7/2012 | Zamost et al. |
| 2006/0172384 A1 | 8/2006 | Reardon et al. |
| 2007/0020227 A1 | 1/2007 | Sheppard |
| 2007/0041936 A1 | 2/2007 | Brady et al. |
| 2007/0042469 A1 | 2/2007 | Brady et al. |
| 2007/0042470 A1 | 2/2007 | Brady et al. |
| 2007/0042471 A1 | 2/2007 | Brady et al. |
| 2007/0048263 A1 | 3/2007 | Meyer |
| 2007/0048798 A1 | 3/2007 | Zamost et al. |
| 2007/0048842 A1 | 3/2007 | Zamost et al. |
| 2007/0048844 A1 | 3/2007 | Brady et al. |
| 2007/0054374 A1 | 3/2007 | Brady et al. |
| 2007/0054375 A1 | 3/2007 | Brady et al. |
| 2007/0054376 A1 | 3/2007 | Brady et al. |
| 2007/0054377 A1 | 3/2007 | Brady et al. |
| 2007/0059804 A1 | 3/2007 | Brady et al. |
| 2007/0065406 A1 | 3/2007 | Brady et al. |
| 2007/0172923 A1 | 7/2007 | Brady et al. |
| 2008/0081786 A1 | 4/2008 | Sheppard et al. |
| 2008/0096252 A1 | 4/2008 | Zamost et al. |
| 2008/0124299 A1 | 5/2008 | Klucher et al. |
| 2008/0167244 A1 | 7/2008 | Doyle et al. |
| 2008/0214788 A1 | 9/2008 | Sheppard et al. |
| 2008/0279816 A1 | 11/2008 | Brady et al. |
| 2009/0018080 A1 | 1/2009 | Klucher et al. |
| 2009/0069274 A1 | 3/2009 | Sheppard et al. |
| 2009/0149636 A1 | 6/2009 | Sheppard et al. |
| 2009/0263352 A1 | 10/2009 | Klucher et al. |
| 2009/0326204 A1 | 12/2009 | Sheppard et al. |
| 2010/0003722 A1 | 1/2010 | Zamost et al. |

OTHER PUBLICATIONS

Ogata, et al., "Protection against bacteriophage contamination in industrial fermentation processes—Investigation and applications of phage resistance mechanisms in bacteria," Virus, (50)1, pp. 17-26, Jun. 2000.

Qm, Sun, et al., "High-level expression and purification of recombinant huGM-CSF (9.127)/1L6 (29-184) fusion protein in *Escherichia coli*", Bibliographic Details: Protein Expression and Purification; Aug. 2005; vol. 42(2); pp. 278.285; PMID: 15935697 & Retraction Notice, 1 pg.

SEQUENCE LISTING

<160> NUMBER OF SEQ ID NOS: 31

<210> SEQ ID NO 1
<211> LENGTH: 549
<212> TYPE: DNA
<213> ORGANISM: Artificial Sequence
<220> FEATURE:
<223> OTHER INFORMATION: recombinant human IL-29 C172S
<220> FEATURE:
<221> NAME/KEY: CDS
<222> LOCATION: (1)...(549)

<400> SEQUENCE: 1

```
atg ggt ccg gtt ccg acc tct aaa cca acc acc act ggt aaa ggt tgc     48
Met Gly Pro Val Pro Thr Ser Lys Pro Thr Thr Thr Gly Lys Gly Cys
 1               5                  10                  15 cac atc ggt cgt ttc aaa tct ctg tct ccg cag gaa ctg gct tct ttc     96
His Ile Gly Arg Phe Lys Ser Leu Ser Pro Gln Glu Leu Ala Ser Phe
             20                  25                  30 aaa aaa gct cgt gac gct ctg gaa gaa tct ctg aaa ctg aaa aac tgg    144
Lys Lys Ala Arg Asp Ala Leu Glu Glu Ser Leu Lys Leu Lys Asn Trp
         35                  40                  45 tct tgc tct tct ccg gtt ttc ccg ggt aac tgg gat ctg cgt ctg ctg    192
Ser Cys Ser Ser Pro Val Phe Pro Gly Asn Trp Asp Leu Arg Leu Leu
     50                  55                  60 cag gtt cgt gaa cgt ccg gtt gct ctg gaa gct gaa ctg gct ctg acc    240
Gln Val Arg Glu Arg Pro Val Ala Leu Glu Ala Glu Leu Ala Leu Thr
 65                  70                  75                  80 ctg aaa gtt ctg gaa gct gct gca ggt cct gct ctg gaa gat gtt ctg    288
Leu Lys Val Leu Glu Ala Ala Ala Gly Pro Ala Leu Glu Asp Val Leu
                 85                  90                  95 gat cag ccg ctg cac act ctg cac cac atc ctg tct cag ctg cag gct    336
Asp Gln Pro Leu His Thr Leu His His Ile Leu Ser Gln Leu Gln Ala
            100                 105                 110 tgc att caa ccg caa ccg acc gct ggt ccg cgt ccg cgt ggt cgt ctg    384
Cys Ile Gln Pro Gln Pro Thr Ala Gly Pro Arg Pro Arg Gly Arg Leu
        115                 120                 125
```

```
cac cac tgg ctg cat cgt ctg cag gaa gct ccg aaa aaa gaa tct gct    432
His His Trp Leu His Arg Leu Gln Glu Ala Pro Lys Lys Glu Ser Ala
        130                 135                 140 ggt tgc ctg gaa gct tct gtt acc ttc aac ctg ttc cgt ctg ctg acc    480
Gly Cys Leu Glu Ala Ser Val Thr Phe Asn Leu Phe Arg Leu Leu Thr
145                 150                 155                 160 cgt gat ctg aaa tac gtt gct gat ggt aac ctg tct ctg cgt acc tct    528
Arg Asp Leu Lys Tyr Val Ala Asp Gly Asn Leu Ser Leu Arg Thr Ser
                165                 170                 175 acc cat ccg gaa tct acc taa                                        549
Thr His Pro Glu Ser Thr *
            180

<210> SEQ ID NO 2
<211> LENGTH: 182
<212> TYPE: PRT
<213> ORGANISM: Artificial Sequence
<220> FEATURE:
<223> OTHER INFORMATION: recombinant human IL-29 C172S

<400> SEQUENCE: 2

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His Ile Leu Ser Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Ser Leu Arg Thr Ser
                165                 170                 175

Thr His Pro Glu Ser Thr
            180

<210> SEQ ID NO 3
<211> LENGTH: 552
<212> TYPE: DNA
<213> ORGANISM: Artificial Sequence
<220> FEATURE:
<223> OTHER INFORMATION: recombinant human IL-29 C172S Leucine insert
<220> FEATURE:
<221> NAME/KEY: CDS
<222> LOCATION: (1)...(552)

<400> SEQUENCE: 3 atg ctg ggt ccg gtt ccg acc tct aaa cca acc acc act ggt aaa ggt    48
Met Leu Gly Pro Val Pro Thr Ser Lys Pro Thr Thr Thr Gly Lys Gly
1               5                   10                  15 tgc cac atc ggt cgt ttc aaa tct ctg tct ccg cag gaa ctg gct tct    96
```

```
Cys His Ile Gly Arg Phe Lys Ser Leu Ser Pro Gln Glu Leu Ala Ser
             20                  25                  30 ttc aaa aaa gct cgt gac gct ctg gaa gaa tct ctg aaa ctg aaa aac   144
Phe Lys Lys Ala Arg Asp Ala Leu Glu Glu Ser Leu Lys Leu Lys Asn
             35                  40                  45 tgg tct tgc tct tct ccg gtt ttc ccg ggt aac tgg gat ctg cgt ctg   192
Trp Ser Cys Ser Ser Pro Val Phe Pro Gly Asn Trp Asp Leu Arg Leu
     50                  55                  60 ctg cag gtt cgt gaa cgt ccg gtt gct ctg gaa gct gaa ctg gct ctg   240
Leu Gln Val Arg Glu Arg Pro Val Ala Leu Glu Ala Glu Leu Ala Leu
 65              70                  75                  80 acc ctg aaa gtt ctg gaa gct gct gca ggt cct gct ctg gaa gat gtt   288
Thr Leu Lys Val Leu Glu Ala Ala Ala Gly Pro Ala Leu Glu Asp Val
                     85                  90                  95 ctg gat cag ccg ctg cac act ctg cac cac atc ctg tct cag ctg cag   336
Leu Asp Gln Pro Leu His Thr Leu His His Ile Leu Ser Gln Leu Gln
                 100                 105                 110 gct tgc att caa ccg caa ccg acc gct ggt ccg cgt ccg cgt ggt cgt   384
Ala Cys Ile Gln Pro Gln Pro Thr Ala Gly Pro Arg Pro Arg Gly Arg
             115                 120                 125 ctg cac cac tgg ctg cat cgt ctg cag gaa gct ccg aaa aaa gaa tct   432
Leu His His Trp Leu His Arg Leu Gln Glu Ala Pro Lys Lys Glu Ser
 130                 135                 140 gct ggt tgc ctg gaa gct tct gtt acc ttc aac ctg ttc cgt ctg ctg   480
Ala Gly Cys Leu Glu Ala Ser Val Thr Phe Asn Leu Phe Arg Leu Leu
145                 150                 155                 160 acc cgt gat ctg aaa tac gtt gct gat ggt aac ctg tct ctg cgt acc   528
Thr Arg Asp Leu Lys Tyr Val Ala Asp Gly Asn Leu Ser Leu Arg Thr
                 165                 170                 175 tct acc cat ccg gaa tct acc taa                                   552
Ser Thr His Pro Glu Ser Thr *
             180
```

<210> SEQ ID NO 4
<211> LENGTH: 183
<212> TYPE: PRT
<213> ORGANISM: Artificial Sequence
<220> FEATURE:
<223> OTHER INFORMATION: recombinant human IL-29 C172S Leucine insert

<400> SEQUENCE: 4

```
Met Leu Gly Pro Val Pro Thr Ser Lys Pro Thr Thr Thr Gly Lys Gly
 1               5                  10                  15

Cys His Ile Gly Arg Phe Lys Ser Leu Ser Pro Gln Glu Leu Ala Ser
             20                  25                  30

Phe Lys Lys Ala Arg Asp Ala Leu Glu Glu Ser Leu Lys Leu Lys Asn
             35                  40                  45

Trp Ser Cys Ser Ser Pro Val Phe Pro Gly Asn Trp Asp Leu Arg Leu
     50                  55                  60

Leu Gln Val Arg Glu Arg Pro Val Ala Leu Glu Ala Glu Leu Ala Leu
 65              70                  75                  80

Thr Leu Lys Val Leu Glu Ala Ala Ala Gly Pro Ala Leu Glu Asp Val
                     85                  90                  95

Leu Asp Gln Pro Leu His Thr Leu His His Ile Leu Ser Gln Leu Gln
                 100                 105                 110

Ala Cys Ile Gln Pro Gln Pro Thr Ala Gly Pro Arg Pro Arg Gly Arg
             115                 120                 125

Leu His His Trp Leu His Arg Leu Gln Glu Ala Pro Lys Lys Glu Ser
 130                 135                 140
```

```
Ala Gly Cys Leu Glu Ala Ser Val Thr Phe Asn Leu Phe Arg Leu Leu
145                 150                 155                 160

Thr Arg Asp Leu Lys Tyr Val Ala Asp Gly Asn Leu Ser Leu Arg Thr
                165                 170                 175

Ser Thr His Pro Glu Ser Thr
            180

<210> SEQ ID NO 5
<211> LENGTH: 531
<212> TYPE: DNA
<213> ORGANISM: Artificial Sequence
<220> FEATURE:
<223> OTHER INFORMATION: recombinant human IL-29 C172S d2-7
<220> FEATURE:
<221> NAME/KEY: CDS
<222> LOCATION: (1)...(531)

<400> SEQUENCE: 5 atg aaa cca acc acc act ggt aaa ggt tgc cac atc ggt cgt ttc aaa      48
Met Lys Pro Thr Thr Thr Gly Lys Gly Cys His Ile Gly Arg Phe Lys
1               5                   10                  15 tct ctg tct ccg cag gaa ctg gct tct ttc aaa aaa gct cgt gac gct      96
Ser Leu Ser Pro Gln Glu Leu Ala Ser Phe Lys Lys Ala Arg Asp Ala
                20                  25                  30 ctg gaa gaa tct ctg aaa ctg aaa aac tgg tct tgc tct tct ccg gtt     144
Leu Glu Glu Ser Leu Lys Leu Lys Asn Trp Ser Cys Ser Ser Pro Val
            35                  40                  45 ttc ccg ggt aac tgg gat ctg cgt ctg ctg cag gtt cgt gaa cgt ccg     192
Phe Pro Gly Asn Trp Asp Leu Arg Leu Leu Gln Val Arg Glu Arg Pro
        50                  55                  60 gtt gct ctg gaa gct gaa ctg gct ctg acc ctg aaa gtt ctg gaa gct     240
Val Ala Leu Glu Ala Glu Leu Ala Leu Thr Leu Lys Val Leu Glu Ala
65                  70                  75                  80 gct gca ggt cct gct ctg gaa gat gtt ctg gat cag ccg ctg cac act     288
Ala Ala Gly Pro Ala Leu Glu Asp Val Leu Asp Gln Pro Leu His Thr
                85                  90                  95 ctg cac cac atc ctg tct cag ctg cag gct tgc att caa ccg caa ccg     336
Leu His His Ile Leu Ser Gln Leu Gln Ala Cys Ile Gln Pro Gln Pro
            100                 105                 110 acc gct ggt ccg cgt ccg cgt ggt cgt ctg cac cac tgg ctg cat cgt     384
Thr Ala Gly Pro Arg Pro Arg Gly Arg Leu His His Trp Leu His Arg
        115                 120                 125 ctg cag gaa gct ccg aaa aaa gaa tct gct ggt tgc ctg gaa gct tct     432
Leu Gln Glu Ala Pro Lys Lys Glu Ser Ala Gly Cys Leu Glu Ala Ser
130                 135                 140 gtt acc ttc aac ctg ttc cgt ctg ctg acc cgt gat ctg aaa tac gtt     480
Val Thr Phe Asn Leu Phe Arg Leu Leu Thr Arg Asp Leu Lys Tyr Val
145                 150                 155                 160 gct gat ggt aac ctg tct ctg cgt acc tct acc cat ccg gaa tct acc     528
Ala Asp Gly Asn Leu Ser Leu Arg Thr Ser Thr His Pro Glu Ser Thr
                165                 170                 175 taa                                                                  531
*

<210> SEQ ID NO 6
<211> LENGTH: 176
<212> TYPE: PRT
<213> ORGANISM: Artificial Sequence
<220> FEATURE:
<223> OTHER INFORMATION: recombinant human IL-29 C172S d2-7

<400> SEQUENCE: 6

Met Lys Pro Thr Thr Thr Gly Lys Gly Cys His Ile Gly Arg Phe Lys
```

```
                1               5                   10                  15
            Ser Leu Ser Pro Gln Glu Leu Ala Ser Phe Lys Lys Ala Arg Asp Ala
                         20                  25                  30

Leu Glu Glu Ser Leu Lys Leu Lys Asn Trp Ser Cys Ser Ser Pro Val
                         35                  40                  45

Phe Pro Gly Asn Trp Asp Leu Arg Leu Leu Gln Val Arg Glu Arg Pro
                50                  55                  60

Val Ala Leu Glu Ala Glu Leu Ala Leu Thr Leu Lys Val Leu Glu Ala
             65                  70                  75                  80

Ala Ala Gly Pro Ala Leu Glu Asp Val Leu Asp Gln Pro Leu His Thr
                             85                  90                  95

Leu His His Ile Leu Ser Gln Leu Gln Ala Cys Ile Gln Pro Gln Pro
                            100                 105                 110

Thr Ala Gly Pro Arg Pro Arg Gly Arg Leu His His Trp Leu His Arg
                            115                 120                 125

Leu Gln Glu Ala Pro Lys Lys Glu Ser Ala Gly Cys Leu Glu Ala Ser
                        130                 135                 140

Val Thr Phe Asn Leu Phe Arg Leu Leu Thr Arg Asp Leu Lys Tyr Val
            145                 150                 155                 160

Ala Asp Gly Asn Leu Ser Leu Arg Thr Ser Thr His Pro Glu Ser Thr
                            165                 170                 175

<210> SEQ ID NO 7
<211> LENGTH: 549
<212> TYPE: DNA
<213> ORGANISM: Artificial Sequence
<220> FEATURE:
<223> OTHER INFORMATION: recombinant human IL-29 C1 mutant
<220> FEATURE:
<221> NAME/KEY: CDS
<222> LOCATION: (1)...(549)
<220> FEATURE:
<221> NAME/KEY: variation
<222> LOCATION: 33, 47, 48, 57
<223> OTHER INFORMATION: n = A, T, G or C

<400> SEQUENCE: 7 atg ggt ccg gtt ccg acc tct aaa cca acc mcn act ggt aaa ggt dnn       48
Met Gly Pro Val Pro Thr Ser Lys Pro Thr Xaa Thr Gly Lys Gly Xaa
 1               5                  10                  15 cac atc grn cgt ttc aaa tct ctg tct ccg cag gaa ctg gct tct ttc       96
His Ile Xaa Arg Phe Lys Ser Leu Ser Pro Gln Glu Leu Ala Ser Phe
                 20                  25                  30 aaa aaa gct cgt gac gct ctg gaa gaa tct ctg aaa ctg aaa aac tgg     144
Lys Lys Ala Arg Asp Ala Leu Glu Glu Ser Leu Lys Leu Lys Asn Trp
             35                  40                  45 tct tgc tct tct ccg gtt ttc ccg ggt aac tgg gat ctg cgt ctg ctg     192
Ser Cys Ser Ser Pro Val Phe Pro Gly Asn Trp Asp Leu Arg Leu Leu
         50                  55                  60 cag gtt cgt gaa cgt ccg gtt gct ctg gaa gct gaa ctg gct ctg acc     240
Gln Val Arg Glu Arg Pro Val Ala Leu Glu Ala Glu Leu Ala Leu Thr
 65                  70                  75                  80 ctg aaa gtt ctg gaa gct gct gca ggt cct gct ctg gaa gat gtt ctg     288
Leu Lys Val Leu Glu Ala Ala Ala Gly Pro Ala Leu Glu Asp Val Leu
                 85                  90                  95 gat cag ccg ctg cac act ctg cac cac atc ctg tct cag ctg cag gct     336
Asp Gln Pro Leu His Thr Leu His His Ile Leu Ser Gln Leu Gln Ala
            100                 105                 110 tgc att caa ccg caa ccg acc gct ggt ccg cgt ccg cgt ggt cgt ctg     384
Cys Ile Gln Pro Gln Pro Thr Ala Gly Pro Arg Pro Arg Gly Arg Leu
        115                 120                 125
```

```
cac cac tgg ctg cat cgt ctg cag gaa gct ccg aaa aaa gaa tct gct      432
His His Trp Leu His Arg Leu Gln Glu Ala Pro Lys Lys Glu Ser Ala
    130                 135                 140 ggt tgc ctg gaa gct tct gtt acc ttc aac ctg ttc cgt ctg ctg acc      480
Gly Cys Leu Glu Ala Ser Val Thr Phe Asn Leu Phe Arg Leu Leu Thr
145                 150                 155                 160 cgt gat ctg aaa tac gtt gct gat ggt ray ctg tgc ctg cgt acc tct      528
Arg Asp Leu Lys Tyr Val Ala Asp Gly Xaa Leu Cys Leu Arg Thr Ser
                165                 170                 175 acc cat ccg gaa tct acc taa                                          549
Thr His Pro Glu Ser Thr *
            180

<210> SEQ ID NO 8
<211> LENGTH: 182
<212> TYPE: PRT
<213> ORGANISM: Artificial Sequence
<220> FEATURE:
<223> OTHER INFORMATION: recombinant human IL-29 C1 mutant
<220> FEATURE:
<221> NAME/KEY: VARIANT
<222> LOCATION: (11)...(11)
<223> OTHER INFORMATION: Xaa = Thr or Pro
<220> FEATURE:
<221> NAME/KEY: VARIANT
<222> LOCATION: (16)...(16)
<223> OTHER INFORMATION: Xaa = Ser, Ala, Thr, Val or Asn
<220> FEATURE:
<221> NAME/KEY: VARIANT
<222> LOCATION: (19)...(19)
<223> OTHER INFORMATION: Xaa = Gly or Asp
<220> FEATURE:
<221> NAME/KEY: VARIANT
<222> LOCATION: (170)...(170)
<223> OTHER INFORMATION: Xaa = Asn or Asp

<400> SEQUENCE: 8

Met Gly Pro Val Pro Thr Ser Lys Pro Thr Xaa Thr Gly Lys Gly Xaa
 1               5                  10                  15

His Ile Xaa Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Xaa Leu Cys Leu Arg Thr Ser
                165                 170                 175

Thr His Pro Glu Ser Thr
            180
```

<210> SEQ ID NO 9
<211> LENGTH: 549
<212> TYPE: DNA
<213> ORGANISM: Artificial Sequence
<220> FEATURE:
<223> OTHER INFORMATION: recombinant human IL-29 C5 mutant
<220> FEATURE:
<221> NAME/KEY: CDS
<222> LOCATION: (1)...(549)
<220> FEATURE:
<221> NAME/KEY: variation
<222> LOCATION: 33, 57, 515, 516
<223> OTHER INFORMATION: n = A, T, G or C

<400> SEQUENCE: 9

```
atg ggt ccg gtt ccg acc tct aaa cca acc mcn act ggt aaa ggt tgc      48
Met Gly Pro Val Pro Thr Ser Lys Pro Thr Xaa Thr Gly Lys Gly Cys
1               5                   10                  15 cac atc grn cgt ttc aaa tct ctg tct ccg cag gaa ctg gct tct ttc      96
His Ile Xaa Arg Phe Lys Ser Leu Ser Pro Gln Glu Leu Ala Ser Phe
                20                  25                  30 aaa aaa gct cgt gac gct ctg gaa gaa tct ctg aaa ctg aaa aac tgg     144
Lys Lys Ala Arg Asp Ala Leu Glu Glu Ser Leu Lys Leu Lys Asn Trp
            35                  40                  45 tct tgc tct tct ccg gtt ttc ccg ggt aac tgg gat ctg cgt ctg ctg     192
Ser Cys Ser Ser Pro Val Phe Pro Gly Asn Trp Asp Leu Arg Leu Leu
        50                  55                  60 cag gtt cgt gaa cgt ccg gtt gct ctg gaa gct gaa ctg gct ctg acc     240
Gln Val Arg Glu Arg Pro Val Ala Leu Glu Ala Glu Leu Ala Leu Thr
65                  70                  75                  80 ctg aaa gtt ctg gaa gct gct gca ggt cct gct ctg gaa gat gtt ctg     288
Leu Lys Val Leu Glu Ala Ala Ala Gly Pro Ala Leu Glu Asp Val Leu
                85                  90                  95 gat cag ccg ctg cac act ctg cac cac atc ctg tct cag ctg cag gct     336
Asp Gln Pro Leu His Thr Leu His His Ile Leu Ser Gln Leu Gln Ala
            100                 105                 110 tgc att caa ccg caa ccg acc gct ggt ccg cgt ccg cgt ggt cgt ctg     384
Cys Ile Gln Pro Gln Pro Thr Ala Gly Pro Arg Pro Arg Gly Arg Leu
        115                 120                 125 cac cac tgg ctg cat cgt ctg cag gaa gct ccg aaa aaa gaa tct gct     432
His His Trp Leu His Arg Leu Gln Glu Ala Pro Lys Lys Glu Ser Ala
130                 135                 140 ggt tgc ctg gaa gct tct gtt acc ttc aac ctg ttc cgt ctg ctg acc     480
Gly Cys Leu Glu Ala Ser Val Thr Phe Asn Leu Phe Arg Leu Leu Thr
145                 150                 155                 160 cgt gat ctg aaa tac gtt gct gat ggt ray ctg dnn ctg cgt acc tct     528
Arg Asp Leu Lys Tyr Val Ala Asp Gly Xaa Leu Xaa Leu Arg Thr Ser
                165                 170                 175 acc cat ccg gaa tct acc taa                                         549
Thr His Pro Glu Ser Thr *
            180
```

<210> SEQ ID NO 10
<211> LENGTH: 182
<212> TYPE: PRT
<213> ORGANISM: Artificial Sequence
<220> FEATURE:
<223> OTHER INFORMATION: recombinant human IL-29 C5 mutant
<220> FEATURE:
<221> NAME/KEY: VARIANT
<222> LOCATION: (11)...(11)
<223> OTHER INFORMATION: Xaa = Thr or Pro
<220> FEATURE:
<221> NAME/KEY: VARIANT
<222> LOCATION: (19)...(19)
<223> OTHER INFORMATION: Xaa = Gly or Asp
<220> FEATURE:

```
<221> NAME/KEY: VARIANT
<222> LOCATION: (170)...(170)
<223> OTHER INFORMATION: Xaa = Asp or Asn
<220> FEATURE:
<221> NAME/KEY: VARIANT
<222> LOCATION: (172)...(172)
<223> OTHER INFORMATION: Xaa = Ser, Ala, Thr, Val or Asn

<400> SEQUENCE: 10

Met Gly Pro Val Pro Thr Ser Lys Pro Thr Xaa Thr Gly Lys Gly Cys
 1               5                  10                  15

His Ile Xaa Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Xaa Leu Xaa Leu Arg Thr Ser
                165                 170                 175

Thr His Pro Glu Ser Thr
            180

<210> SEQ ID NO 11
<211> LENGTH: 549
<212> TYPE: DNA
<213> ORGANISM: Homo sapiens
<220> FEATURE:
<221> NAME/KEY: CDS
<222> LOCATION: (1)...(549)

<400> SEQUENCE: 11 atg ggt ccg gtt ccg acc tct aaa cca acc acc act ggt aaa ggt tgc      48
Met Gly Pro Val Pro Thr Ser Lys Pro Thr Thr Thr Gly Lys Gly Cys
 1               5                  10                  15 cac atc ggt cgt ttc aaa tct ctg tct ccg cag gaa ctg gct tct ttc      96
His Ile Gly Arg Phe Lys Ser Leu Ser Pro Gln Glu Leu Ala Ser Phe
            20                  25                  30 aaa aaa gct cgt gac gct ctg gaa gaa tct ctg aaa ctg aaa aac tgg     144
Lys Lys Ala Arg Asp Ala Leu Glu Glu Ser Leu Lys Leu Lys Asn Trp
        35                  40                  45 tct tgc tct tct ccg gtt ttc ccg ggt aac tgg gat ctg cgt ctg ctg     192
Ser Cys Ser Ser Pro Val Phe Pro Gly Asn Trp Asp Leu Arg Leu Leu
    50                  55                  60 cag gtt cgt gaa cgt ccg gtt gct ctg gaa gct gaa ctg gct ctg acc     240
Gln Val Arg Glu Arg Pro Val Ala Leu Glu Ala Glu Leu Ala Leu Thr
65                  70                  75                  80 ctg aaa gtt ctg gaa gct gct gca ggt cct gct ctg gaa gat gtt ctg     288
Leu Lys Val Leu Glu Ala Ala Ala Gly Pro Ala Leu Glu Asp Val Leu
                85                  90                  95
```

```
gat cag ccg ctg cac act ctg cac cac atc ctg tct cag ctg cag gct     336
Asp Gln Pro Leu His Thr Leu His His Ile Leu Ser Gln Leu Gln Ala
            100                 105                 110 tgc att caa ccg caa ccg acc gct ggt ccg cgt ccg cgt ggt cgt ctg     384
Cys Ile Gln Pro Gln Pro Thr Ala Gly Pro Arg Pro Arg Gly Arg Leu
        115                 120                 125 cac cac tgg ctg cat cgt ctg cag gaa gct ccg aaa aaa gaa tct gct     432
His His Trp Leu His Arg Leu Gln Glu Ala Pro Lys Lys Glu Ser Ala
    130                 135                 140 ggt tgc ctg gaa gct tct gtt acc ttc aac ctg ttc cgt ctg ctg acc     480
Gly Cys Leu Glu Ala Ser Val Thr Phe Asn Leu Phe Arg Leu Leu Thr
145                 150                 155                 160 cgt gat ctg aaa tac gtt gct gat ggt aac ctg tgc ctg cgt acc tct     528
Arg Asp Leu Lys Tyr Val Ala Asp Gly Asn Leu Cys Leu Arg Thr Ser
                165                 170                 175 acc cat ccg gaa tct acc taa                                          549
Thr His Pro Glu Ser Thr  *
            180

<210> SEQ ID NO 12
<211> LENGTH: 182
<212> TYPE: PRT
<213> ORGANISM: Homo sapiens

<400> SEQUENCE: 12

Met Gly Pro Val Pro Thr Ser Lys Pro Thr Thr Thr Gly Lys Gly Cys
  1               5                  10                  15

His Ile Gly Arg Phe Lys Ser Leu Ser Pro Gln Glu Leu Ala Ser Phe
             20                  25                  30

Lys Lys Ala Arg Asp Ala Leu Glu Glu Ser Leu Lys Leu Lys Asn Trp
         35                  40                  45

Ser Cys Ser Ser Pro Val Phe Pro Gly Asn Trp Asp Leu Arg Leu Leu
     50                  55                  60

Gln Val Arg Glu Arg Pro Val Ala Leu Glu Ala Gly Leu Ala Leu Thr
 65                  70                  75                  80

Leu Lys Val Leu Glu Ala Ala Gly Pro Ala Leu Glu Asp Val Leu
                 85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Cys Leu Arg Thr Ser
                165                 170                 175

Thr His Pro Glu Ser Thr
            180

<210> SEQ ID NO 13
<211> LENGTH: 9
<212> TYPE: DNA
<213> ORGANISM: Artficial Sequence
<220> FEATURE:
<223> OTHER INFORMATION: Zymo2 translational enhancer

<400> SEQUENCE: 13 aatacatta                                                             9
```

```
<210> SEQ ID NO 14
<211> LENGTH: 49
<212> TYPE: DNA
<213> ORGANISM: Artificial Sequence
<220> FEATURE:
<223> OTHER INFORMATION: Oligonucleotide primer ZC42188

<400> SEQUENCE: 14
cggctcgtat aatgtgtgga attgtgagcg gataacaatt cccctctag            49

<210> SEQ ID NO 15
<211> LENGTH: 53
<212> TYPE: DNA
<213> ORGANISM: Artificial Sequence
<220> FEATURE:
<223> OTHER INFORMATION: Oligonucleotide ZC42187

<400> SEQUENCE: 15
gcggataaca attcccctct agaaataatt ttgtattaca ttaagaagga gat        53

<210> SEQ ID NO 16
<211> LENGTH: 63
<212> TYPE: DNA
<213> ORGANISM: Artificial Sequence
<220> FEATURE:
<223> OTHER INFORMATION: Oligonucleotide ZC42194

<400> SEQUENCE: 16
gctgaaaatc ttatctcatc cgccaaaaca cccgggatat atatctcctt cttaatgtaa  60
tac                                                                63

<210> SEQ ID NO 17
<211> LENGTH: 42
<212> TYPE: DNA
<213> ORGANISM: Artificial Sequence
<220> FEATURE:
<223> OTHER INFORMATION: Oligonucleotide ZC29741

<400> SEQUENCE: 17
tctgatttaa tctgtatcag gctgaaaatc ttatctcatc cg                    42

<210> SEQ ID NO 18
<211> LENGTH: 62
<212> TYPE: DNA
<213> ORGANISM: Artificial Sequence
<220> FEATURE:
<223> OTHER INFORMATION: Oligonucleotide ZC44559

<400> SEQUENCE: 18
atgggtccgg ttccgacctc taaccaacc accactggta aaggttgcca catcggtcgt   60
tt                                                                 62

<210> SEQ ID NO 19
<211> LENGTH: 78
<212> TYPE: DNA
<213> ORGANISM: Artificial Sequence
<220> FEATURE:
<223> OTHER INFORMATION: Oligonucleotide ZC44566

<400> SEQUENCE: 19
tcttccagag cgtcacgagc tttttgaaa gaagccagtt cctgcggaga cagagatttg   60
aaacgaccga tgtggcaa                                                78
```

-continued

<210> SEQ ID NO 20
<211> LENGTH: 84
<212> TYPE: DNA
<213> ORGANISM: Artificial Sequence
<220> FEATURE:
<223> OTHER INFORMATION: Oligonucleotide ZC44565

<400> SEQUENCE: 20
tcgtgacgct ctggaagaat ctctgaaact gaaaaactgg tcttgctctt ctccggtttt    60
cccgggtaac tgggatctgc gtct                                           84

<210> SEQ ID NO 21
<211> LENGTH: 74
<212> TYPE: DNA
<213> ORGANISM: Artificial Sequence
<220> FEATURE:
<223> OTHER INFORMATION: Oligonucleotide ZC44562

<400> SEQUENCE: 21
tcagggtcag agccagttca gcttccagag caaccggacg ttcacgaacc tgcagcagac    60
gcagatccca gtta                                                      74

<210> SEQ ID NO 22
<211> LENGTH: 73
<212> TYPE: DNA
<213> ORGANISM: Artificial Sequence
<220> FEATURE:
<223> OTHER INFORMATION: Oligonucleotide ZC44563

<400> SEQUENCE: 22
aactggctct gaccctgaaa gttctggaag ctgctgcagg tcctgctctg aagatgttc     60 tggatcagcc gct                                                       73

<210> SEQ ID NO 23
<211> LENGTH: 60
<212> TYPE: DNA
<213> ORGANISM: Artificial Sequence
<220> FEATURE:
<223> OTHER INFORMATION: Oligonucleotide ZC44560

<400> SEQUENCE: 23
atgcaagcct gcagctgaga caggatgtgg tgcagagtgt gcagcggctg atccagaaca    60

<210> SEQ ID NO 24
<211> LENGTH: 76
<212> TYPE: DNA
<213> ORGANISM: Artificial Sequence
<220> FEATURE:
<223> OTHER INFORMATION: Oligonucleotide ZC44561

<400> SEQUENCE: 24
tcagctgcag gcttgcattc aaccgcaacc gaccgctggt ccgcgtccgc gtggtcgtct    60
gcaccactgg ctgcat                                                    76

<210> SEQ ID NO 25
<211> LENGTH: 71
<212> TYPE: DNA
<213> ORGANISM: Artificial Sequence
<220> FEATURE:
<223> OTHER INFORMATION: Oligonucleotide ZC44564

<400> SEQUENCE: 25
aacagaagct tccaggcaac cagcagattc tttttcgga gcttcctgca gacgatgcag     60
ccagtggtgc a                                                         71

<210> SEQ ID NO 26
<211> LENGTH: 69
<212> TYPE: DNA
<213> ORGANISM: Artificial Sequence
<220> FEATURE:
<223> OTHER INFORMATION: Oligonucleotide ZC44557

<400> SEQUENCE: 26
tgcctggaag cttctgttac cttcaacctg ttccgtctgc tgacccgtga tctgaaatac      60
gttgctgat                                                              69

<210> SEQ ID NO 27
<211> LENGTH: 65
<212> TYPE: DNA
<213> ORGANISM: Artificial Sequence
<220> FEATURE:
<223> OTHER INFORMATION: Oligonucleotide ZC44558

<400> SEQUENCE: 27
ttaggtagat tccggatggg tagaggtacg caggcacagg ttaccatcag caacgtattt      60
cagat                                                                  65

<210> SEQ ID NO 28
<211> LENGTH: 41
<212> TYPE: DNA
<213> ORGANISM: Artificial Sequence
<220> FEATURE:
<223> OTHER INFORMATION: Oligonucleotide ZC44340

<400> SEQUENCE: 28
cgttgctgat ggtaacctgt ctctgcgtac ctctacccat c                          41

<210> SEQ ID NO 29
<211> LENGTH: 41
<212> TYPE: DNA
<213> ORGANISM: Artificial Sequence
<220> FEATURE:
<223> OTHER INFORMATION: Oligonucleotide ZC44341

<400> SEQUENCE: 29
gatgggtaga ggtacgcaga gacaggttac catcagcaac g                          41

<210> SEQ ID NO 30
<211> LENGTH: 64
<212> TYPE: DNA
<213> ORGANISM: Artificial Sequence
<220> FEATURE:
<223> OTHER INFORMATION: Oligonucleotide ZC49249

<400> SEQUENCE: 30
gaaataattt tgtattacat taagaaggag atatatatat gaaaccaacc accactggta      60
aagg                                                                   64

<210> SEQ ID NO 31
<211> LENGTH: 65
<212> TYPE: DNA
<213> ORGANISM: Artificial Sequence
<220> FEATURE:
<223> OTHER INFORMATION: Oligonucleotide ZC45403

```
<400> SEQUENCE: 31
tctgtatcag gctgaaaatc ttatctcatc cgccaaaaca ttaggtagat tccggatggg    60
tagag                                                                65
```

PRODUCTION AND PURIFICATION OF IL-29

CROSS-REFERENCES

The present application is a divisional of U.S. patent application Ser. No. 13/488,840, filed Jun. 5, 2012, which is a divisional of U.S. patent application Ser. No. 13/114,566, filed May 24, 2011, now U.S. Pat. No. 8,211,670, which is a divisional of U.S. patent application Ser. No. 12/701,358, filed Feb. 5, 2010, now U.S. Pat. No. 7,968,315, which is a divisional of U.S. patent application Ser. No. 12/537,935, filed Aug. 7, 2009, now U.S. Pat. No. 7,759,092, which is a continuation of U.S. patent application Ser. No. 11/538,688, filed Oct. 4, 2006, now abandoned, which claims the benefit of U.S. Patent Application Ser. No. 60/723,544, filed Oct. 4, 2005, all of which are herein incorporated by reference in their entireties.

BACKGROUND

The increased availability and identification of genes from human and other genomes has led to an increased need for efficient expression and purification of recombinant proteins. The expression of proteins in bacteria is by far the most widely used approach for the production of cloned genes. For many reasons, expression in bacteria is preferred to expression in eukaryotic cells. For example, bacteria are much easier to grow than eukaryotic cells. More specifically, the availability of a wealth of sophisticated molecular genetic tools and thousands of mutants make *E. coli*, as an expression host, extremely useful for protein production. However, the high-level production of functional proteins in *E. coli.*, especially those from eukaryotic sources has often been difficult.

IL-28A, IL-28B, and IL-29 comprise a recently discovered new family of proteins that have sequence homology to type I interferons and genomic homology to IL-10. This new family is fully described in co-owned PCT application WO 02/086087 and Sheppard et al., Nature Immunol. 4:63-68, 2003. Functionally, IL-28A, IL-28B and IL-29 resemble type I INFs in their ability to induce an antiviral state in cells but, unlike type I IFNs, they do not display antiproliferative activity against certain B cell lines.

Recombinant IL-29 has been produced in prokaryotic cells, in particular *E. coli*. The resulting bacterial produced protein is not glycosylated, and is produced in an aggregated state. Production of IL-29 from *E. coli* requires that the aggregated proteins be solubilized from the insoluble inclusion bodies and renatured or refolded. Without renaturation, the specific activity of the recombinant protein will be significantly reduced.

Despite advances in the expression of recombinant proteins in bacterial hosts, there exists a need for improved methods for producing biologically active and purified recombinant IL-29 proteins in prokaryotic systems which result in higher yields for protein production. These and other aspects of the invention will become evident upon reference to the following detailed description.

DESCRIPTION

Definitions

In the description that follows, a number of terms are used extensively. The following definitions are provided to facilitate understanding of the invention.

Unless otherwise specified, "a," "an," "the," and "at least one" are used interchangeably and mean one or more than one.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

The term "contig" denotes a nucleic acid molecule that has a contiguous stretch of identical or complementary sequence to another nucleic acid molecule. Contiguous sequences are said to "overlap" a given stretch of a nucleic acid molecule either in their entirety or along a partial stretch of the nucleic acid molecule.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

"Linear DNA" denotes non-circular DNA molecules with free 5' and 3' ends. Linear DNA can be prepared from closed circular DNA molecules, such as plasmids, by enzymatic digestion or physical disruption.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoters include "inducible promoters", for example, but are not limited to, IPTG-inducible promoters (such as the tac promoters; trc promoters; lac promoters; bacteriophage T7, T3, T5 promoters; and nprM-lac promoters), trp promoters, phoA promoters, recA promoters, cspA promoters, tetA promoters, and bacteriophage $\lambda p_L$. See Sambrook et al., Molecular Cloning: *A Laboratory Manual*, 3rd ed., Cold Spring Harbor Laboratory Press, Cold Spring Harbor, N.Y., 2001. Addition of an "inducing agent", e.g., isopropyl thiogalactopyranoside (IPTG) for an IPTG-inducible promoter, will induce expression of the gene or genes under the control of the IPTG-inducible promoter. A typical promoter will have three components, consisting of consensus sequences at −35 and −10 with a sequence of between 16 and 19 nucleotides between them (Lisset, S. and Margalit, H., *Nucleic Acids Res.* 21: 1512, 1993). Promoters of this sort include the lac, tip, trp-lac (tac) and trp-lac(trc) promoters. If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a eukaryotic regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner. Bacterial promoters have regulatory elements that bind and modulate the activity of the core promoter, such as operator sequences that bind activator or repressor molecules.

A "cloning vector" is a nucleic acid molecule, such as a plasmid, cosmid, or bacteriophage, which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide resistance to antibiotic.

An "expression vector" is a nucleic acid molecule encoding a gene that is expressed in a host cell. Typically, an expression vector comprises a transcriptional promoter, a gene, an origin of replication, a selectable marker, and a transcriptional terminator. Gene expression is usually placed under the control of a promoter, and such a gene is said to be "operably linked to" the promoter. Similarly, a regulatory element and a core promoter are operably linked if the regulatory element modulates the activity of the core promoter. An expression vector may also be known as an expression construct.

A "recombinant host" is a cell that contains a heterologous nucleic acid molecule, such as a cloning vector or expression vector.

The term "expression" refers to the biosynthesis of a gene product. For example, in the case of a structural gene, expression involves transcription of the structural gene into mRNA and the translation of mRNA into one or more polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein. Proteins are defined herein in terms of their amino acid backbone structures; substituents such as carbohydrate groups and non-peptidic groups are generally not specified, but may be present nonetheless.

A peptide or polypeptide encoded by a non-host DNA molecule is a "heterologous" peptide or polypeptide.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" or "N-terminal" and "carboxyl-terminal" or "C-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "fusion protein" is a hybrid protein expressed by a nucleic acid molecule comprising nucleotide sequences of at least two genes.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

The term "isotonic" is used herein for its conventional meaning, which is a tonicity equal to that of blood, equivalent to a 0.9% solution of NaCl. "An isotonic amount" of a salt is that amount required to make a solution isotonic or to produce an isotonic solution upon reconstitution of a lyophilized preparation.

Concentrations are specified herein in units of molarity or % w/v of liquid compositions. When the composition is in the form of a lyophilized powder, the concentrations of the respective components will be such as to provide the specified concentration on reconstitution of the powder.

Due to the imprecision of standard analytical methods, molecular weights and lengths of polymers are understood to be approximate values. When such a value is expressed as "about" X or "approximately" X, the stated value of X will be understood to be accurate to ±10%.

The present invention provides an expression vector for producing an IL-29 polypeptide comprising the operably linked elements of a prokaryotic origin of replication, a transcriptional initiation DNA element, and polynucleotide sequence selected from the group consisting of SEQ ID NOs: 1, 3, 5, 7, 9 and 11 and a transcriptional terminator. In another aspect, the expression vector is the vector pTAP440 or pTAP395. Optionally, the expression vector may further include a selectable marker, such as kanamycin.

In another aspect, the present invention provides prokaryotic host cells transformed with expression vectors comprising a polynucleotide sequence encoding an IL-29 polypeptide (e.g., SEQ ID NOs: 2, 4, 6, 8, 10, 12, and biologically active mutants), vector pTAP440 or vector pTAP395. In other embodiments, the host strain is *E. coli* strain W3110, zGOLD1, or zGOLD5.

In another aspect, the present invention provides methods for producing an IL-29 polypeptide under conditions wherein the IL-29 polypeptide is expressed. In one embodiment, the method comprises culturing a host cell expressing an IL-29 polypeptide after being transformed with pTAP440 or pTAP395. In another embodiment, the method comprises culturing a host cell transformed with an expression vector comprising a polypeptide selected from the group consisting of SEQ ID NOs: 2, 4, 6, 8, 10, 12, and biologically active mutants. The method also comprises recovering the host cells from the growth medium, and then isolating the IL-29 polypeptide from the host cells.

In other aspects, the present invention provides a method of producing an IL-29 polypeptide comprising the steps as described above, in a fed batch fermentation process or a batch fermentation process.

The present invention also provides methods of producing an IL-29 polypeptide comprising culturing a host cell in a suitable growth medium in a shake flask to an optical density (OD) of between 5 and 20 at 600 nm, inoculating a fermentation vessel with 1 to 5% v/v (e.g., 1% v/v and 2% v/v) of shake flask medium containing host cells, culturing the host cells in a growth medium at a pH of 6.2 to 7.2 (e.g., pH 6.8), where a feed solution is fed into the fermentation vessel before 10 to 20 hours (e.g., 15 hours) elapsed fermentation time (EFT), adding an inducing agent to the fermentation vessel at 20 to 30 hours EFT (e.g., 24 hours), and harvesting the host cells at 48 to 56 hours EFT. In one embodiment, the inducing agent is isopropyl thiogalactopyranoside (IPTG) at 0.5 to 2 mM (e.g., 1 mM). In another embodiment, the feed solution comprises a carbohydrate, e.g., glycerol and glucose, and the feed is 10 to 30 grams/Liter (g/L) (e.g., 10-20 g/L) of carbohydrate per hour. In another embodiment, the glycerol in the feed solution is 40 to 70% v/v glycerol (e.g., 50% w/v) or the glucose is 40 to 70% w/v glucose (e.g., 50% w/v). In further embodiments, the glycerol is about 70% v/v or the glucose is about 60% w/v.

The present invention also provides methods of producing an IL-29 polypeptide comprising seeding a flask with an inoculum comprising an *E. coli* W3110, ZGold1, or ZGold5 host cells expressing an IL-29 polypeptide selected from the group consisting of SEQ ID NOs: 2, 4, 6, 8, 10, 12, and biologically active mutants, or an *E. coli* W3110, ZGold1, or ZGold5 host cell comprising a pTAP440 or pTAP395 vector, wherein an IL-29 polypeptide is expressed, and with growth medium comprising about 5 to 7 g/L glycerol or glucose, culturing the inoculum in a growth medium for 16 to 20 hours at about 30° C. to about 37° C., transferring the cultured inoculum in growth medium to a batch fermentator at a concentration 1 to 5% v/v inoculum (e.g., 1 to 2% v/v), fermenting the batch fermentation at about 37° C. and about pH 6.8 with about 10 to 30 g/L (e.g., 10 to 20 g/L) glycerol or glucose, introducing a glucose feed at about 6 to 8 hours EFT of about 5 to 15 grams of glucose or glycerol per liter per hour and continuing until end of a fermentation run, adding IPTG at about 24 hours EFT to final concentration of 0.5 to 2 mM (e.g., 1 mM), fermenting an additional 20 to 30 hours (e.g., 24 hours), harvesting fermentation broth from the fermenter, adding an equal volume of water to the fermentation broth, and homogenizing and centrifuging to collect a cell pellet or cell slurry comprising IL-29 protein material.

In another aspect, the present invention provides methods of isolating insoluble IL-29 polypeptide comprising a sequence of amino acid residues selected from the group consisting of SEQ ID NOs: 2, 4, 6, 8, 10, 12, and biologically active mutants comprising separating water insoluble IL-29 polypeptide from a cell pellet or slurry, dissolving the insoluble IL-29 material in a chaotropic solvent, diluting the chaotropic solvent and refolding the IL-29 polypeptide; and isolating the IL-29 polypeptide, wherein the isolated IL-29 polypeptide is capable of being biologically active. In one embodiment of the invention, the isolated IL-29 polypeptide is at least 90% pure. In another embodiment, the isolated IL-29 polypeptide is at least 90% pure and has an endotoxin level of less than 10 endotoxin units per mg IL-29 polypeptide in a Limulus amoebocyte lysate assay based on USP <85>.

The present invention also provides a method of isolating insoluble IL-29 polypeptide comprising a sequence of amino acid residues selected from the group consisting of SEQ ID NOs: 2, 4, 6, 8, 10, 12, and biologically active mutants comprising separating from a fermentation broth a cell pellet or cell slurry comprising water insoluble IL-29 polypeptide material, homogenizing the cell pellet or cell slurry to collect inclusion bodies, dissolving the insoluble IL-29 polypeptide material in a chaoptropic solvent comprising a guanidine salt, diluting the chaotropic solvent by addition of a refolding buffer comprising arginine salts and a mixture of reducing and oxidizing components, isolating the IL-29 polypeptide by removing unfolded and aggregated proteins by filtering, and purifying the IL-29 refolded polypeptide on a cation exchange column, wherein the isolated and purified IL-29 is capable of being biologically active.

In another aspect, the present invention provides a method of isolating insoluble IL-29 polypeptide comprising a sequence of amino acid residues selected from the group consisting of SEQ ID NOs: 2, 4, 6, 8, 10, 12, and biologically active mutants comprising separating from a fermentation broth a cell pellet or cell slurry comprising water insoluble IL-29 material, homogenizing the cell pellet or cell slurry to collect inclusion bodies, dissolving the insoluble IL-29 protein material in a chaotropic solvent comprising a guanidine salt, diluting the chaotropic solvent by addition of a refolding buffer comprising arginine salts and a mixture of reducing and oxidizing components, isolating the IL-29 polypeptide by removing unfolded and aggregated proteins by filtering, purifying the IL-29 refolded polypeptide on a cation exchange column, and purifying the IL-29 eluate on a hydrophobic interaction column, wherein the isolated and purified IL-29 polypeptide is capable of being biologically active.

In another aspect, the present invention provides a method for isolating insoluble IL-29 polypeptide comprising a sequence of amino acid residues selected from the group consisting of SEQ ID NOs: 2, 4, 6, 8, 10, 12, and biologically active mutants comprising separating from a fermentation broth a cell pellet or cell slurry comprising water insoluble IL-29 polypeptide material, homogenizing the cell pellet or cell slurry to collect inclusion bodies, dissolving the insoluble IL-29 polypeptide material in a chaotropic solvent comprising about 6 M guanidine hydrochloride, 40 mM dithriothreitol (DTT) for about one hour at room temperature, refolding the dissolved inclusion bodies in a solution by diluting into refolding buffer comprising about 2 mM DTT, 4 mM cystine oxidation-reduction pair at least 20 times, adjusting the pH to about 5.5 with about 20% acetic acid and allowing the solution to react for at least five hours, diluting the solution with about 1+1.4 volumes 25 mM acetate, pH 5.5, filtering the solution, loading the solution on a Tosohaas SP-550C resin column equilibrated to pH 5.5 using sodium acetate buffer, washing the resin column with about 2 M sodium chloride, washing the resin column with about 0.6 M sodium chloride to elute bound IL-29 polypeptide, adding ammonium sulfate to a concentration of about 1.5 M to eluate and filtering eluate solution, loading eluate solution onto a Tosohaas butyl 650-M column equilibrated to 1.5 M ammonium sulfate, 0.05 sodium chloride in sodium acetate buffer, diluting eluate onto a SP Sepharose HP column equilibrated with sodium acetate buffer, washing column with 20 column volume linear gradient from 0.3 0.7 M sodium chloride, concentration the IL-29 protein, and exchanging buffer to formulation buffer using tangential flow ultrafiltration.

The present invention also provides for the covalently attaching a polyethylene glycol (PEG) to a purified IL-29 polypeptide. The PEG can be attached to the N- or C-terminus of the IL-29 polypeptide. The PEG may be 20 kDa methoxyPEG-propionaldehyde. The present invention also provides for the purification of mono-PEGylated IL-29.

The present invention also provides for a method of producing an IL-29 polypeptide comprising (a) culturing a prokaryotic host cell comprising a nucleic acid molecule encoding an IL-29 polypeptide operably linked to an inducible promoter in a first growth medium under conditions wherein the encoded IL-29 polypeptide is expressed in a shake flask to an OD600 of 5 to 20; (b) inoculating a fermentation vessel with 1 to 5% v/v of shake flask medium containing host cells; (c) culturing the host cells in a second growth medium at a pH of 6.2 to 7.2, wherein a carbohydrate feed solution is fed into the fermentation vessel at 6 to 8 hours elapsed fermentation time; (d) adding an inducing agent to the fermentation vessel at 20 to 30 hours elapsed fermentation time; and (e) harvesting the prokaryotic host cells at 48 to 56 hours elapsed fermentation time. Optionally, the carbohydrate feed solution may comprise a glycerol or glucose at a concentration of 10 to 30 g/L growth medium, and a feed rate of 5-15 grams of glycerol or glucose per liter per hour. The prokaryotic host cell may be *Escherichia coli*, such as, for instance, W3110, ZGOLD1, and ZGOLD5. In addition, the prokaryotic host cell, e.g., *Escherichia coli*, may be OmpT deficient and/or fhuA deficient. The encoded IL-29 polypeptide may include an amino acid sequence selected from the group of SEQ ID NOs: 2, 4, 6, 8, 10 and 12. The inducing agent of step (d) may be isopropyl thiogalactopyranoside, which may be added to the culture at a concentration of 0.5 mM to 2 mM.

The present invention also provides a method of recovering an IL-29 polypeptide from a prokaryotic host cell comprising (a) culturing a prokaryotic host cell comprising a nucleic acid molecule encoding an IL-29 polypeptide operably linked to an inducible promoter in growth medium under conditions wherein the encoded IL-29 polypeptide is expressed; (b) adding an inducing agent to induce expression of the IL-29 polypeptide; (c) harvesting the prokaryotic host cells; (d) lysing the prokaryotic host cells; (e) centrifuging the lysed prokaryotic host cells; (f) recovering the inclusion body pellet; (g) solubilizing the inclusion body pellet in 4-6 M guanidine hydrochloride and 10-50 mM dithiothreitol for 1-2 hours at 15-25° C.; and (h) adding the solubilized IL-29 polypeptide to a refolding buffer comprising 0.05-0.5% polyethylene glycol, salt, 0.5 M-1.25 M arginine and a mixture of reduced and oxidized molecules for 1-26 hours at a temperature of 4-30° C. and a pH 7.3-8.5, wherein the solubilized IL-29 polypeptide is refolded; (i) quenching the refolding reaction by adjusting the pH to 5.5-6.5; (j) diluting the quenched refolding solution 1.5- to 10-fold in water or low ionic strength buffer at pH 5-7; and (k) filtering the quenched, diluted refold solution through filters to remove precipitate or particulates. The prokaryotic host cells of step (d) may be lysed by homogenization. The lysed prokaryotic host cells of step (e) may be centrifuged by either batch or continuous centrifugation. The IL-29 polypeptide of step (h) may be added to the refolding buffer to a final concentration of 0.05-3.0 mg/ml. The mixture of reduced and oxidized molecules of the refolding buffer of step (h) may be molecules selected from the group of cysteine and cystine, dithiothreitol and cystine, reduced glutathione and oxidized glutathione, and dithiothreitol and oxidized glutathione. The present invention also provides for an IL-29 polypeptide produced and/or recovered by methods as described herein.

The present invention also provides a method of purifying an IL-29 polypeptide comprising (a) providing the produced and recovered IL-29 polypeptide as described herein; (b)

loading the filtered solution comprising refolded IL-29 polypeptide of step (a) onto a cation exchange chromatography column equilibrated with sodium acetate at pH 5.5; (c) eluting bound IL-29 polypeptide with sodium chloride in sodium acetate, pH 5.5; and (d) adjusting the eluate with ammonium sulfate to 1 M concentration, and passing the adjusted IL-29 polypeptide eluate through a 0.45 μm filter. Optionally, the IL-29 polypeptide may elute from the cation exchange column to form a pool at about 0.7 M-0.8 M sodium chloride after using a linear gradient elution of 0-2M sodium chloride. In another aspect in purifying an IL-29 polypeptide the method may further comprise (e) loading the IL-29 polypeptide of step (d) onto a hydrophobic interaction chromatography column equilibrated with 50 mM sodium acetate, 1.5 M ammonium sulfate, pH 5.5; (f) eluting the IL-29 polypeptide with a linear 50 mM sodium acetate, 1.5 M ammonium sulfate to 50 mM sodium acetate with no ammonium sulfate, pH 5.5; (g) diluting the eluate about 6-fold with water or low ionic strength buffer and passing the diluted IL-29 polypeptide eluate through a 0.2 μm or 0.45 μm filter. Optionally, the IL-29 polypeptide may elute from the hydrophobic interaction chromatography column at about 0.75 M ammonium sulfate to 0 M ammonium sulfate. In another aspect in purifying an IL-29 polypeptide the method may even further comprise (h) loading the IL-29 polypeptide of step (g) onto a high performance cation exchange chromatography column equilibrated with 50 mM sodium acetate comprising 0-300 mM sodium chloride, pH 5.5; and (i) eluting the IL-29 polypeptide with a higher concentration of sodium chloride in 50 mM sodium acetate, pH 5.5, in a step or gradient elution format. Optionally, the IL-29 polypeptide may elute from the high performance cation exchange chromatography column at about 0.4 M sodium chloride to 0.6 M sodium chloride after using a gradient elution of 300 to 800 mM sodium chloride. The IL-29 polypeptide may be at least 98% pure by sodium dodecyl sulfate polyacrylamide gel analysis and aggregates may be less than 0.2% by size exclusion HPLC. The present invention also provides for an IL-29 polypeptide produced and/or recovered and/or purified by methods as described herein.

The present invention also provides a method of concentrating a purified IL-29 polypeptide comprising (a) providing a purified IL-29 polypeptide as described herein; (b) adding the IL-29 polypeptide to a tangential flow filtration plate and frame system comprising one or more 3-10 kDa molecular weight cut-off membrane; (c) applying a transmembrane pressure of 15-25 psi to the system to ultrafilter the solution to a higher concentration; and (c) filtering the concentrated IL-29 polypeptide through a 0.2 μm membrane. The IL-29 polypeptide may be at least 98% pure by sodium dodecyl sulfate polyacrylamide gel analysis and aggregates may be less than 0.2% by size exclusion HPLC. The IL-29 polypeptide may have an endotoxin level of less than 10 endotoxin units per milligram of IL-29 polypeptide in a Limulus amoebocyte lysate assay based on USP <85>. The present invention also provides for an IL-29 polypeptide produced and/or recovered and/or purified and/or concentrating by methods as described herein.

The present invention also provides a method of monopegylating an IL-29 polypeptide comprising (a) providing 3-5 g/L IL-29 polypeptide in a sodium acetate buffer solution; (b) adding 10-20 mM sodium cyanoborohydride to the solution of step (a); (c) adding a 2-fold molar excess of derivatized polyethylene glycol to the solution of step (b); and (d) mixing the solution of step (c) for 10-18 hours at 16-20° C. Optionally, the monopegylated IL-29 polypeptide may have at least 99% monopegylated as measured by reversed phase HPLC.

The present invention also provides for monopegylated IL-29 polypeptides as produced by methods as described herein.

The present invention also provides a method of purifying monopegylated IL-29 polypeptide comprising (e) providing monopegylated IL-29 polypeptide as described herein; (f) diluting the solution of step (e) 2-fold with 50 mM sodium acetate, pH 5.5; (g) filtering the solution of step (f) through a 0.2 μm membrane; (h) loading the solution of step (g) onto a high performance cation exchange chromatography column equilibrated with 50 mM sodium acetate, 200 mM sodium chloride, pH 5.5; (i) eluting monopegylated IL-29 polypeptide from the high performance cation exchange chromatography column with a linear 50 mM sodium acetate, 500 mM sodium chloride gradient, pH 5.5; (j) adding the monopegylated IL-29 polypeptide to a tangential flow filtration plate and frame system comprising one or more 3-10 kDa molecular weight cut-off membrane; (k) applying a transmembrane pressure of 15-25 psi to the system to ultrafilter the solution to a higher concentration; (l) using the system to buffer exchange the concentrated IL-29 polypeptide into an appropriate formulation buffer by diafiltration; and (m) filtering the concentrated monopegylated IL-29 polypeptide through a 0.2 μm membrane. The polyethylene glycol may include a 20 kDa or 30 kDa mono-methoxyPEG-propionaldehyde. The polyethylene glycol may be N-terminally or C-terminally attached to the IL-29 polypeptide. Optionally, the monopegylated IL-29 polypeptide may have at least 99% monopegylated as measured by reversed phase HPLC. The present invention also provides for monopegylated IL-29 polypeptides as produced and purified by methods as described herein.

IL-29 Polynucleotides and Polypeptides

The human IL-29 gene encodes a mature polypeptide, not including the signal sequence, of 182 amino acids. The IL-29 sequence as expressed using a prokaryotic expression system has an N-terminal methionine, and the nucleotide and corresponding amino acid sequences are shown in SEQ ID NOs:11 and 12 (referred to herein as IL-29 wildtype sequences), respectively. The nucleotide sequence of SEQ ID NO:11 shows a codon optimized sequence that is within the scope of the present invention. "IL-29", "recombinant IL-29", "recombinant human IL-29", are used interchangeably herein and refer to an IL-29 molecule in general and include IL-29 wildtype (SEQ ID NO:12), IL-29C172S (SEQ ID NO:2), IL-29 C172S Leucine Insert (SEQ ID NO:4), IL-29 C172S d2-7 (SEQ ID NO:6), IL-29 C1 mutants (SEQ ID NO:8), IL-29 C5 mutants (SEQ ID NO:10), fragments (N-terminal, C-terminal and N- and C-terminal fragments), variants and fusions thereof.

The present invention also provides isolated IL-29 polypeptides that have a substantially similar sequence identity to the polypeptide of SEQ ID NO:6. The term "substantially similar sequence identity" is used herein to denote polypeptides comprising at least 80%, at least 90%, at least 95%, at least 96%, at least 97%, at least 97.5%, at least 98%, at least 98.5%, at least 99%, at least 99.5%, or greater than 99.5% sequence identity to the amino acid sequences.

Zcyto21 or IL-29 polypeptides of the present invention also include a mutation at the fifth cysteine, C5, of the mature polypeptide. For example, C5 from the N-terminus of the polypeptide of SEQ ID NO:12, is the cysteine at position 172. This fifth cysteine or C5 of IL-29 can be mutated, for example, to any amino acid which will not form a disulfide bond with another cysteine (e.g., serine, alanine, threonine, valine, or asparagine). These IL-29 C5 mutant polypeptides have a disulfide bond pattern of C1(Cys16 of SEQ ID NO:10)/C3(Cys113 of SEQ ID NO:10) and C2(Cys50 of SEQ ID NO:10)/C4(Cys146 of SEQ ID NO:10). IL-29 C5 mutant molecules of the present invention include polynucleotide molecules as shown in SEQ ID NO:9, including DNA and RNA molecules, that encode IL-29 C5 mutant polypeptides as shown in SEQ ID NO:10 (U.S. Patent Application Ser. Nos. 60/700,905 and 60/700,951, PCT publication WO 03/066002 (Kotenko et al.) and PCT publication WO 02/092762 (Baum et al.)).

The various uses, for example, for an IL-29 molecule of the present invention include a use as an antiviral drug (e.g., for the treatment of hepatitis C, hepatitis B, human immunodeficiency virus) as well as a therapeutic agent for various autoimmune disorders (e.g., multiple sclerosis) and various cancers (e.g., hepatocellular carcinoma, renal cell carcinoma, pancreatic cancer, colon cancer, various B-cell malignancies), which are more fully disclosed in commonly assigned U.S. Pat. No. 6,927,040, U.S. Pat. No. 7,038,032, WO 04/037995, WO 05/023862, U.S. Patent Publication No. 2005-0244423, U.S. Patent Publication No. 2006-012644, U.S. patent application Ser. No. 11/458,945, and U.S. patent application Ser. No. 11/489,894, all of which are herein incorporated by reference in their entirety.

The present invention also includes biologically active mutants of IL-29 C5 cysteine mutants, which provide at least partial antiviral activity, or have therapeutic activity for autoimmune diseases and/or various cancers. The biologically active mutants of IL-29 C5 cysteine mutants of the present invention include N-, C-, and N- and C-terminal deletions of IL-29, e.g., the polypeptides of SEQ ID NO:10 encoded by the polynucleotides of SEQ ID NO:9.

N-terminally modified biologically active mutants of IL-29 C5 mutants include, for example, amino acid residues 2-182 of SEQ ID NO:10 which is encoded by nucleotides 4-546 of SEQ ID NO:9; amino acid residues 3-182 of SEQ ID NO:10 which is encoded by nucleotides 7-546 of SEQ ID NO:9; amino acid residues 4-182 of SEQ ID NO:10 which is encoded by nucleotides 10-546 of SEQ ID NO:9; amino acid residues 5-182 of SEQ ID NO:10 which is encoded by nucleotides 13-546 of SEQ ID NO:9; amino acid residues 6-182 of SEQ ID NO:10 which is encoded by nucleotides 16-546 of SEQ ID NO:9; amino acid residues 7-182 of SEQ ID NO:10 which is encoded by nucleotides 19-546 of SEQ ID NO:9; amino acid residues 8-182 of SEQ ID NO:10 which is encoded by nucleotides 22-546 of SEQ ID NO:9; amino acid residues 9-182 of SEQ ID NO:10 which is encoded by nucleotides 25-546 of SEQ ID NO:9; amino acid residues 10-182 of SEQ ID NO:10 which is encoded by nucleotides 28-546 of SEQ ID NO:9; amino acid residues 11-182 of SEQ ID NO:10 which is encoded by nucleotides 31-546 of SEQ ID NO:9; amino acid residues 12-182 of SEQ ID NO:10 which is encoded by nucleotides 34-546 of SEQ ID NO:9; amino acid residues 13-182 of SEQ ID NO:10 which is encoded by nucleotides 37-546 of SEQ ID NO:9; amino acid residues 14-182 of SEQ ID NO:10 which is encoded by nucleotides 40-546 of SEQ ID NO:9; amino acid residues 15-182 of SEQ ID NO:10 which is encoded by nucleotides 43-546 of SEQ ID NO:9. The N-terminally modified biologically active mutants of IL-29 C5 mutants of the present invention may also include an N-terminal methione if expressed, for instance, in E. coli.

C-terminally modified biologically active mutants of IL-29 C5 mutants include, for example, amino acid residues 1-181 of SEQ ID NO:10 which is encoded by nucleotides 1-543 of SEQ ID NO:9; amino acid residues 1-180 of SEQ ID NO:10 which is encoded by nucleotides 1-540 of SEQ ID NO:9; amino acid residues 1-179 of SEQ ID NO:10 which is encoded by nucleotides 1-537 of SEQ ID NO:9; amino acid residues 1-178 of SEQ ID NO:10 which is encoded by nucleotides 1-534 of SEQ ID NO:9; amino acid residues 1-177 of SEQ ID NO:10 which is encoded by nucleotides 1-531 of SEQ ID NO:9; amino acid residues 1-176 of SEQ ID NO:10 which is encoded by nucleotides 1-528 of SEQ ID NO:9; amino acid residues 1-175 of SEQ ID NO:10 which is encoded by nucleotides 1-525 of SEQ ID NO:9; amino acid residues 1-174 of SEQ ID NO:10 which is encoded by nucleotides 1-522 of SEQ ID NO:9; amino acid residues 1-173 of SEQ ID NO:10 which is encoded by nucleotides 1-519 of SEQ ID NO:9; amino acid residues 1-172 of SEQ ID NO:10 which is encoded by nucleotides 1-516 of SEQ ID NO:9. The C-terminally modified biologically active mutants of IL-29 C5 mutants of the present invention may also include an N-terminal Methione if expressed, for instance, in E. coli.

N-terminally and C-terminally modified biologically active mutants of IL-29 C5 mutants include, for example, amino acid residues 2-182 of SEQ ID NO:10 which is encoded by nucleotides 4-546 of SEQ ID NO:9; amino acid residues 2-181 of SEQ ID NO:10 which is encoded by nucleotides 4-543 of SEQ ID NO:9; amino acid residues 2-180 of SEQ ID NO:10 which is encoded by nucleotides 4-540 of SEQ ID NO:9; amino acid residues 2-179 of SEQ ID NO:10 which is encoded by nucleotides 4-537 of SEQ ID NO:9; amino acid residues 2-178 of SEQ ID NO:10 which is encoded by nucleotides 4-534 of SEQ ID NO:9; amino acid residues 2-177 of SEQ ID NO:10 which is encoded by nucleotides 4-531 of SEQ ID NO:9; amino acid residues 2-176 of SEQ ID NO:10 which is encoded by nucleotides 4-528 of SEQ ID NO:9; amino acid residues 2-175 of SEQ ID NO:10 which is encoded by nucleotides 4-525 of SEQ ID NO:9; amino acid residues 2-174 of SEQ ID NO:10 which is encoded by nucleotides 4-522 of SEQ ID NO:9; amino acid residues 2-173 of SEQ ID NO:10 which is encoded by nucleotides 4-519 of SEQ ID NO:9; amino acid residues 2-172 of SEQ ID NO:10 which is encoded by nucleotides 4-516 of SEQ ID NO:9; amino acid residues 3-182 of SEQ ID NO:10 which is encoded by nucleotides 7-546 of SEQ ID NO:9; amino acid residues 3-181 of SEQ ID NO:10 which is encoded by nucleotides 7-543 of SEQ ID NO:9; amino acid residues 3-180 of SEQ ID NO:10 which is encoded by nucleotides 7-540 of SEQ ID NO:9; amino acid residues 3-179 of SEQ ID NO:10 which is encoded by nucleotides 7-537 of SEQ ID NO:9; amino acid residues 3-178 of SEQ ID NO:10 which is encoded by nucleotides 7-534 of SEQ ID NO:9; amino acid residues 3-177 of SEQ ID NO:10 which is encoded by nucleotides 7-531 of SEQ ID NO:9; amino acid residues 3-176 of SEQ ID NO:10 which is encoded by nucleotides 7-528 of SEQ ID NO:9; amino acid residues 3-175 of SEQ ID NO:10 which is encoded by nucleotides 7-525 of SEQ ID NO:9; amino acid residues 3-174 of SEQ ID NO:10 which is encoded by nucleotides 7-522 of SEQ ID NO:9; amino acid residues 3-173 of SEQ ID NO:10 which is encoded by nucleotides 7-519 of SEQ ID NO:9; amino acid residues 3-172 of SEQ ID NO:10 which is encoded by nucleotides 7-516 of SEQ ID NO:9; amino acid residues 4-182 of SEQ ID NO:10 which is encoded by nucleotides 10-546 of SEQ ID NO:9; amino acid residues 4-181 of SEQ ID NO:10 which is encoded by nucleotides 10-543 of SEQ ID NO:9; amino acid residues 4-180 of SEQ ID NO:10 which is encoded by nucleotides 10-540 of SEQ ID NO:9; amino acid residues 4-179 of SEQ ID NO:10 which is encoded by nucleotides 10-537 of SEQ ID NO:9; amino acid residues 4-178 of SEQ ID NO:10 which is encoded by nucleotides 10-534 of SEQ ID NO:9; amino acid residues 4-177 of SEQ ID NO:10 which is encoded by nucleotides 10-531 of SEQ ID NO:9; amino acid residues 4-176 of SEQ ID NO:10 which is encoded by nucleotides 10-528 of SEQ ID NO:9; amino acid residues 4-175 of SEQ ID NO:10 which is encoded by nucleotides 10-525 of SEQ ID NO:9; amino acid residues 4-174 of SEQ ID NO:10 which is encoded by nucleotides 10-522 of SEQ ID NO:9; amino acid residues 4-173 of SEQ ID NO:10 which is encoded by nucleotides 10-519 of SEQ ID NO:9; amino acid residues 4-172 of SEQ ID NO:10 which is encoded by nucleotides 10-516 of SEQ ID NO:9; amino acid residues 5-182 of SEQ ID NO:10 which is encoded by nucleotides 13-546 of SEQ ID NO:9; amino acid residues 5-181 of SEQ ID NO:10 which is encoded by nucleotides 13-543 of SEQ ID NO:9; amino acid residues 5-180 of SEQ ID NO:10 which is encoded by nucleotides 13-540 of SEQ ID NO:9; amino acid residues 5-179 of SEQ ID NO:10 which is encoded by nucleotides 13-537 of SEQ ID NO:9; amino acid residues 5-178 of SEQ ID NO:10 which is encoded by nucleotides 13-534 of SEQ ID NO:9; amino acid residues 5-177 of SEQ ID NO:10 which is encoded by nucleotides 13-531 of SEQ ID NO:9; amino acid residues 5-176 of SEQ ID NO:10 which is encoded by nucleotides 13-528 of SEQ ID NO:9; amino acid residues 5-175 of SEQ ID NO:10 which is encoded by nucleotides 13-525 of SEQ ID NO:9; amino acid residues 5-174 of SEQ ID NO:10 which is encoded by nucleotides 13-522 of SEQ ID NO:9; amino acid residues 5-173 of SEQ ID NO:10 which is encoded by nucleotides 13-519 of SEQ ID NO:9; amino acid residues 5-172 of SEQ ID NO:10 which is encoded by nucleotides 13-516 of SEQ ID NO:9; amino acid residues 6-182 of SEQ ID NO:10 which is encoded by nucleotides 16-546 of SEQ ID NO:9; amino acid residues 6-181 of SEQ ID NO:10 which is encoded by nucleotides 16-543 of SEQ ID NO:9; amino acid residues 6-180 of SEQ ID NO:10 which is encoded by nucleotides 16-540 of SEQ ID NO:9; amino acid residues 6-179 of SEQ ID NO:10 which is encoded by nucleotides 16-537 of SEQ ID NO:9; amino acid residues 6-178 of SEQ ID NO:10 which is encoded by nucleotides 16-534 of SEQ ID NO:9; amino acid residues 6-177 of SEQ ID NO:10 which is encoded by nucleotides 16-531 of SEQ ID NO:9; amino acid residues 6-176 of SEQ ID NO:10 which is encoded by nucleotides 16-528 of SEQ ID NO:9; amino acid residues 6-175 of SEQ ID NO:10 which is encoded by nucleotides 16-525 of SEQ ID NO:9; amino acid residues 6-174 of SEQ ID NO:10 which is encoded by nucleotides 16-522 of SEQ ID NO:9; amino acid residues 6-173 of SEQ ID NO:10 which is encoded by nucleotides 16-519 of SEQ ID NO:9; amino acid residues 6-172 of SEQ ID NO:10 which is encoded by nucleotides 16-516 of SEQ ID NO:9; amino acid residues 7-182 of SEQ ID NO:10 which is encoded by nucleotides 19-546 of SEQ ID NO:9; amino acid residues 7-181 of SEQ ID NO:10 which is encoded by nucleotides 19-543 of SEQ ID NO:9; amino acid residues 7-180 of SEQ ID NO:10 which is encoded by nucleotides 19-540 of SEQ ID NO:9; amino acid residues 7-179 of SEQ ID NO:10 which is encoded by nucleotides 19-537 of SEQ ID NO:9; amino acid residues 7-178 of SEQ ID NO:10 which is encoded by nucleotides 19-534 of SEQ ID NO:9; amino acid residues 7-177 of SEQ ID NO:10 which is encoded by nucleotides 19-531 of SEQ ID NO:9; amino acid residues 7-176 of SEQ ID NO:10 which is encoded by nucleotides 19-528 of SEQ ID NO:9; amino acid residues 7-175 of SEQ ID NO:10 which is encoded by nucleotides 19-525 of SEQ ID NO:9; amino acid residues 7-174 of SEQ ID NO:10 which is encoded by nucleotides 19-522 of SEQ ID NO:9; amino acid residues 7-173 of SEQ ID NO:10 which is encoded by nucleotides 19-519 of SEQ ID NO:9; amino acid residues 7-172 of SEQ ID NO:10 which is encoded by nucleotides 19-516 of SEQ ID NO:9; amino acid residues 8-182 of SEQ ID NO:10 which is encoded by nucleotides 22-546 of SEQ ID NO:9; amino acid residues 8-181 of SEQ ID NO:10 which is encoded by nucleotides 22-543 of SEQ ID NO:9; amino acid residues 8-180 of SEQ ID NO:10 which is encoded by nucleotides 22-540 of SEQ ID NO:9; amino acid residues 8-179 of SEQ ID NO:10 which is encoded by nucleotides 22-537 of SEQ ID NO:9; amino acid residues 8-178 of SEQ ID NO:10 which is encoded by nucleotides 22-534 of SEQ ID NO:9; amino acid residues 8-177 of SEQ ID NO:10 which is encoded by nucleotides 22-531 of SEQ ID NO:9; amino acid residues 8-176 of SEQ ID NO:10 which is encoded by nucleotides 22-528 of SEQ ID NO:9; amino acid residues 8-175 of SEQ ID NO:10 which is encoded by nucleotides 22-525 of SEQ ID NO:9; amino acid residues 8-174 of SEQ ID NO:10 which is encoded by nucleotides 22-522 of SEQ ID NO:9; amino acid residues 8-173 of SEQ ID NO:10 which is encoded by nucleotides 22-519 of SEQ ID NO:9; amino acid residues 8-172 of SEQ ID NO:10 which is encoded by nucleotides 22-516 of SEQ ID NO:9; amino acid residues 9-182 of SEQ ID NO:10 which is encoded by nucleotides 25-546 of SEQ ID NO:9; amino acid residues 9-181 of SEQ ID NO:10 which is encoded by nucleotides 25-543 of SEQ ID NO:9; amino acid residues 9-180 of SEQ ID NO:10 which is encoded by nucleotides 25-540 of SEQ ID NO:9; amino acid residues 9-179 of SEQ ID NO:10 which is encoded by nucleotides 25-537 of SEQ ID NO:9; amino acid residues 9-178 of SEQ ID NO:10 which is encoded by nucleotides 25-534 of SEQ ID NO:9; amino acid residues 9-177 of SEQ ID NO:10 which is encoded by nucleotides 25-531 of SEQ ID NO:9; amino acid residues 9-176 of SEQ ID NO:10 which is encoded by nucleotides 25-528 of SEQ ID NO:9; amino acid residues 9-175 of SEQ ID NO:10 which is encoded by nucleotides 25-525 of SEQ ID NO:9; amino acid residues 9-174 of SEQ ID NO:10 which is encoded by nucleotides 25-522 of SEQ ID NO:9; amino acid residues 9-173 of SEQ ID NO:10 which is encoded by nucleotides 25-519 of SEQ ID NO:9; amino acid residues 9-172 of SEQ ID NO:10 which is encoded by nucleotides 25-516 of SEQ ID NO:9; amino acid residues 10-182 of SEQ ID NO:10 which is encoded by nucleotides 28-546 of SEQ ID NO:9; amino acid residues 10-181 of SEQ ID NO:10 which is encoded by nucleotides 28-543 of SEQ ID NO:9; amino acid residues 10-180 of SEQ ID NO:10 which is encoded by nucleotides 28-540 of SEQ ID NO:9; amino acid residues 10-179 of SEQ ID NO:10 which is encoded by nucleotides 28-537 of SEQ ID NO:9; amino acid residues 10-178 of SEQ ED NO:10 which is encoded by nucleotides 28-534 of SEQ ID NO:9; amino acid residues 10-177 of SEQ ID NO:10 which is encoded by nucleotides 28-531 of SEQ ID NO:9; amino acid residues 10-176 of SEQ ID NO:10 which is encoded by nucleotides 28-528 of SEQ ID NO:9; amino acid residues 10-175 of SEQ ID NO:10 which is encoded by nucleotides 28-525 of SEQ ID NO:9; amino acid residues 10-174 of SEQ ID NO:10 which is encoded by nucleotides 28-522 of SEQ ID NO:9; amino acid residues 10-173 of SEQ ID NO:10 which is encoded by nucleotides 28-519 of SEQ ID NO:9; amino acid residues 10-172 of SEQ ID NO:10 which is encoded by nucleotides 28-516 of SEQ ID NO:9; amino acid residues 11-182 of SEQ ID NO:10 which is encoded by nucleotides 31-546 of SEQ ID NO:9; amino acid residues 11-181 of SEQ ID NO:10 which is encoded by nucleotides 31-543 of SEQ ID NO:9; amino acid residues 11-180 of SEQ ID NO:10 which is encoded by nucleotides 31-540 of SEQ ID NO:9; amino acid residues 11-179 of SEQ ID NO:10 which is encoded by nucleotides 31-537 of SEQ ID NO:9; amino acid residues 11-178 of SEQ ID NO:10 which is encoded by nucleotides 31-534 of SEQ ID NO:9; amino acid residues 11-177 of SEQ ID NO:10 which is encoded by nucleotides 31-531 of SEQ ID NO:9; amino acid residues 11-176 of SEQ ID NO:10 which is encoded by nucleotides 31-528 of SEQ ID NO:9; amino acid residues 11-175 of SEQ ID NO:10 which is encoded by nucleotides 31-525 of SEQ ID NO:9; amino acid residues 11-174 of SEQ ID NO:10 which is encoded by nucleotides 31-522 of SEQ ID NO:9; amino acid residues 11-173 of SEQ ID NO:10 which is encoded by nucleotides 31-519 of SEQ ID NO:9; amino acid residues 11-172 of SEQ ID NO:10 which is encoded by nucleotides 31-516 of SEQ ID NO:9; amino acid residues 12-182 of SEQ ID NO:10 which is encoded by nucleotides 34-546 of SEQ ID NO:9; amino acid residues 12-181 of SEQ ID NO:10 which is encoded by nucleotides 34-543 of SEQ ID NO:9; amino acid residues 12-180 of SEQ ID NO:10 which is encoded by nucleotides 34-540 of SEQ ID NO:9; amino acid residues 12-179 of SEQ ID NO:10 which is encoded by nucleotides 34-537 of SEQ ID NO:9; amino acid residues 12-178 of SEQ ID NO:10 which is encoded by nucleotides 34-534 of SEQ ID NO:9; amino acid residues 12-177 of SEQ ID NO:10 which is encoded by nucleotides 34-531 of SEQ ID NO:9; amino acid residues 12-176 of SEQ ID NO:10 which is encoded by nucleotides 34-528 of SEQ ID NO:9; amino acid residues 12-175 of SEQ ID NO:10 which is encoded by nucleotides 34-525 of SEQ ID NO:9; amino acid residues 12-174 of SEQ ID NO:10 which is encoded by nucleotides 34-522 of SEQ ID NO:9; amino acid residues 12-173 of SEQ ID NO:10 which is encoded by nucleotides 34-519 of SEQ ID NO:9; amino acid residues 12-172 of SEQ ID NO:10 which is encoded by nucleotides 34-516 of SEQ ID NO:9; amino acid residues 13-182 of SEQ ID NO:10 which is encoded by nucleotides 37-546 of SEQ ID NO:9; amino acid residues 13-181 of SEQ ID NO:10 which is encoded by nucleotides 37-543 of SEQ ID NO:9; amino acid residues 13-180 of SEQ ID NO:10 which is encoded by nucleotides 37-540 of SEQ ID NO:9; amino acid residues 13-179 of SEQ ID NO:10 which is encoded by nucleotides 37-537 of SEQ ID NO:9; amino acid residues 13-178 of SEQ ID NO:10 which is encoded by nucleotides 37-534 of SEQ ID NO:9; amino acid residues 13-177 of SEQ ID NO:10 which is encoded by nucleotides 37-531 of SEQ ID NO:9; amino acid residues 13-176 of SEQ ID NO:10 which is encoded by nucleotides 37-528 of SEQ ID NO:9; amino acid residues 13-175 of SEQ ID NO:10 which is encoded by nucleotides 37-525 of SEQ ID NO:9; amino acid residues 13-174 of SEQ ID NO:10 which is encoded by nucleotides 37-522 of SEQ ID NO:9; amino acid residues 13-173 of SEQ ID NO:10 which is encoded by nucleotides 37-519 of SEQ ID NO:9; amino acid residues 13-172 of SEQ ID NO:10 which is encoded by nucleotides 37-516 of SEQ ID NO:9; amino acid residues 14-182 of SEQ ID NO:10 which is encoded by nucleotides 40-546 of SEQ ID NO:9; amino acid residues 14-181 of SEQ ID NO:10 which is encoded by nucleotides 40-543 of SEQ ID NO:9; amino acid residues 14-180 of SEQ ID NO:10 which is encoded by nucleotides 40-540 of SEQ ID NO:9; amino acid residues 14-179 of SEQ ID NO:10 which is encoded by nucleotides 40-537 of SEQ ID NO:9; amino acid residues 14-178 of SEQ ID NO:10 which is encoded by nucleotides 40-534 of SEQ ID NO:9; amino acid residues 14-177 of SEQ ID NO:10 which is encoded by nucleotides 40-531 of SEQ ID NO:9; amino acid residues 14-176 of SEQ ID NO:10 which is encoded by nucleotides 40-528 of SEQ ID NO:9; amino acid residues 14-175 of SEQ ID NO:10 which is encoded by nucleotides 40-525 of SEQ ID NO:9; amino acid residues 14-174 of SEQ ID NO:10 which is encoded by nucleotides 40-522 of SEQ ID NO:9; amino acid residues 40-173 of SEQ ID NO:10 which is encoded by nucleotides 40-519 of SEQ ID NO:9; amino acid residues 14-172 of SEQ ID NO:10 which is encoded by nucleotides 40-516 of SEQ ID NO:9; amino acid residues 15-182 of SEQ ID NO:10 which is encoded by nucleotides 43-546 of SEQ ID NO:9; amino acid residues 15-181 of SEQ ID NO:10 which is encoded by nucleotides 43-543 of SEQ ID NO:9; amino acid residues 15-180 of SEQ ID NO:10 which is encoded by nucleotides 43-540 of SEQ ID NO:9; amino acid residues 15-179 of SEQ ID NO:10 which is encoded by nucleotides 43-537 of SEQ ID NO:9; amino acid residues 15-178 of SEQ ID NO:10 which is encoded by nucleotides 43-534 of SEQ ID NO:9; amino acid residues 15-177 of SEQ ID NO:10 which is encoded by nucleotides 43-531 of SEQ ID NO:9; amino acid residues 15-176 of SEQ ID NO:10 which is encoded by nucleotides 43-528 of SEQ ID NO:9; amino acid residues 15-175 of SEQ ID NO:10 which is encoded by nucleotides 43-525 of SEQ ID NO:9; amino acid residues 15-174 of SEQ ID NO:10 which is encoded by nucleotides 43-522 of SEQ ID NO:9; amino acid residues 15-173 of SEQ ID NO:10 which is encoded by nucleotides 43-519 of SEQ ID NO:9; amino acid residues 15-172 of SEQ ID NO:10 which is encoded by nucleotides 43-516 of SEQ ID NO:9; amino acid residues 16-182 of SEQ ID NO:10 which is encoded by nucleotides 46-546 of SEQ ID NO:9; amino acid residues 16-181 of SEQ ID NO:10 which is encoded by nucleotides 46-543 of SEQ ID NO:9; amino acid residues 16-180 of SEQ ID NO:10 which is encoded by nucleotides 46-540 of SEQ ID NO:9; amino acid residues 16-179 of SEQ ID NO:10 which is encoded by nucleotides 46-537 of SEQ ID NO:9; amino acid residues 16-178 of SEQ ID NO:10 which is encoded by nucleotides 46-534 of SEQ ID NO:9; amino acid residues 16-177 of SEQ ID NO:10 which is encoded by nucleotides 46-531 of SEQ ID NO:9; amino acid residues 16-176 of SEQ ID NO:10 which is encoded by nucleotides 46-528 of SEQ ID NO:9; amino acid residues 16-175 of SEQ ID NO:10 which is encoded by nucleotides 46-525 of SEQ ID NO:9; amino acid residues 16-174 of SEQ ID NO:10 which is encoded by nucleotides 46-522 of SEQ ID NO:9; amino acid residues 16-173 of SEQ ID NO:10 which is encoded by nucleotides 46-519 of SEQ ID NO:9; and amino acid residues 16-172 of SEQ ID NO:10 which is encoded by nucleotides 46-516 of SEQ ID NO:9. The N-terminally and C-terminally modified biologically active mutants of IL-29 C5 mutants of the present invention may also include an N-terminal Methione if expressed, for instance, in *E. coli*.

In addition to the IL-29 C5 mutants, the present invention also includes IL-29 polypeptides comprising a mutation at the first cysteine position, C1, of the mature polypeptide. For example, C1 from the N-terminus of the polypeptide of SEQ ID NO:12, is the cysteine at position 16. These IL-29 C1 mutant polypeptides have a predicted disulfide bond pattern of C2(Cys50 of SEQ ID NO:8)/C4(Cys146 of SEQ ID NO:8) and C3(Cys113 of SEQ ID NO:8)/C5(Cys172 of SEQ ID NO:8). IL-29 C1 mutant molecules of the present invention include polynucleotide molecules as shown in SEQ ID NO:7, including DNA and RNA molecules, that encode IL-29 C1 mutant polypeptides as shown in SEQ ID NO:8.

The present invention also includes biologically active mutants of IL-29 C1 cysteine mutants which provide at least partial antiviral activity, or have therapeutic activity for autoimmune diseases and/or various cancers. The biologically active mutants of IL-29 C1 cysteine mutants of the present invention include N-, C-, and N- and C-terminal deletions of IL-29, e.g., the polypeptides of SEQ ID NO:8 encoded by the polynucleotides of SEQ ID NO:7.

N-terminally modified biologically active mutants of IL-29 C1 mutants include, for example, amino acid residues 2-182 of SEQ ID NO:8 which is encoded by nucleotides 4-546 of SEQ ID NO:7; amino acid residues 3-182 of SEQ ID NO:8 which is encoded by nucleotides 7-546 of SEQ ID NO:7; amino acid residues 4-182 of SEQ ID NO:8 which is encoded by nucleotides 10-546 of SEQ ID NO:7; amino acid residues 5-182 of SEQ ID NO:8 which is encoded by nucleotides 13-546 of SEQ ID NO:7; amino acid residues 6-182 of SEQ ID NO:8 which is encoded by nucleotides 16-546 of SEQ ID NO:7; amino acid residues 7-182 of SEQ ID NO:8 which is encoded by nucleotides 19-546 of SEQ ID NO:7; amino acid residues 8-182 of SEQ ID NO:8 which is encoded by nucleotides 22-546 of SEQ ID NO:7; amino acid residues 9-182 of SEQ ID NO:8 which is encoded by nucleotides 25-546 of SEQ ID NO:7; amino acid residues 10-182 of SEQ ID NO:8 which is encoded by nucleotides 28-546 of SEQ ID NO:7; amino acid residues 11-182 of SEQ ID NO:8 which is encoded by nucleotides 31-546 of SEQ ID NO:7; amino acid residues 12-182 of SEQ ID NO:8 which is encoded by nucleotides 34-182 of SEQ ID NO:7; amino acid residues 13-182 of SEQ ID NO:8 which is encoded by nucleotides 37-546 of SEQ ID NO:7; amino acid residues 14-182 of SEQ ID NO:8 which is encoded by nucleotides 40-546 of SEQ ID NO:7; amino acid residues 15-182 of SEQ ID NO:8 which is encoded by nucleotides 43-546 of SEQ ID NO:7; and amino acid residues 16-182 of SEQ ID NO:8 which is encoded by nucleotides 46-546 of SEQ ID NO:7. The N-terminally modified biologically active mutants of IL-29 C1 mutants of the present invention may also include an N-terminal Methione if expressed, for instance, in *E. coli.*

C-terminally modified biologically active mutants of IL-29 C1 mutants include, for example, amino acid residues 1-181 of SEQ ID NO:8 which is encoded by nucleotides 1-543 of SEQ ID NO:7; amino acid residues 1-180 of SEQ ID NO:8 which is encoded by nucleotides 1-540 of SEQ ID NO:7; amino acid residues 1-179 of SEQ ID NO:8 which is encoded by nucleotides 1-537 of SEQ ID NO:7; amino acid residues 1-178 of SEQ ID NO:8 which is encoded by nucleotides 1-534 of SEQ ID NO:7; amino acid residues 1-177 of SEQ ID NO:8 which is encoded by nucleotides 1-531 of SEQ ID NO:7; amino acid residues 1-176 of SEQ ID NO:8 which is encoded by nucleotides 1-528 of SEQ ID NO:7; amino acid residues 1-175 of SEQ ID NO:8 which is encoded by nucleotides 1-525 of SEQ ID NO:7; amino acid residues 1-174 of SEQ ID NO:8 which is encoded by nucleotides 1-522 of SEQ ID NO:7; amino acid residues 1-173 of SEQ ID NO:8 which is encoded by nucleotides 1-519 of SEQ ID NO:7; and amino acid residues 1-172 of SEQ ID NO:8 which is encoded by nucleotides 1-516 of SEQ ID NO:7. The C-terminally modified biologically active mutants of IL-29 C1 mutants of the present invention may also include an N-terminal methione if expressed, for instance, in *E. coli.*

N-terminally and C-terminally modified biologically active mutants of IL-29 C1 mutants include, for example, amino acid residues 2-181 of SEQ ID NO:8 which is encoded by nucleotides 4-543 of SEQ ID NO:7; amino acid residues 2-180 of SEQ ID NO:8 which is encoded by nucleotides 4-540 of SEQ ID NO:7; amino acid residues 2-179 of SEQ ID NO:8 which is encoded by nucleotides 4-537 of SEQ ID NO:7; amino acid residues 2-178 of SEQ ID NO:8 which is encoded by nucleotides 4-534 of SEQ ID NO:7; amino acid residues 2-177 of SEQ ID NO:8 which is encoded by nucleotides 4-531 of SEQ ID NO:7; amino acid residues 2-176 of SEQ ID NO:8 which is encoded by nucleotides 4-528 of SEQ ID NO:7; amino acid residues 2-175 of SEQ ID NO:8 which is encoded by nucleotides 4-525 of SEQ ID NO:7; amino acid residues 2-174 of SEQ ID NO:8 which is encoded by nucleotides 4-522 of SEQ ID NO:7; amino acid residues 2-173 of SEQ ID NO:8 which is encoded by nucleotides 4-519 of SEQ ID NO:7; amino acid residues 2-172 of SEQ ID NO:8 which is encoded by nucleotides 4-516 of SEQ ID NO:7; amino acid residues 3-181 of SEQ ID NO:8 which is encoded by nucleotides 7-543 of SEQ ID NO:7; amino acid residues 3-180 of SEQ ID NO:8 which is encoded by nucleotides 7-540 of SEQ ID NO:7; amino acid residues 3-179 of SEQ ID NO:8 which is encoded by nucleotides 7-537 of SEQ ID NO:7; amino acid residues 3-178 of SEQ ID NO:8 which is encoded by nucleotides 7-534 of SEQ ID NO:7; amino acid residues 3-177 of SEQ ID NO:8 which is encoded by nucleotides 7-531 of SEQ ID NO:7; amino acid residues 3-176 of SEQ ID NO:8 which is encoded by nucleotides 7-528 of SEQ ID NO:7; amino acid residues 3-175 of SEQ ID NO:8 which is encoded by nucleotides 7-525 of SEQ ID NO:7; amino acid residues 3-174 of SEQ ID NO:8 which is encoded by nucleotides 7-522 of SEQ ID NO:7; amino acid residues 3-173 of SEQ ID NO:8 which is encoded by nucleotides 7-519 of SEQ ID NO:7; amino acid residues 3-172 of SEQ ID NO:8 which is encoded by nucleotides 7-516 of SEQ ID NO:7; amino acid residues 4-181 of SEQ ID NO:8 which is encoded by nucleotides 10-543 of SEQ ID NO:7; amino acid residues 4-180 of SEQ ID NO:8 which is encoded by nucleotides 10-540 of SEQ ID NO:7; amino acid residues 4-179 of SEQ ID NO:8 which is encoded by nucleotides 10-537 of SEQ ID NO:7; amino acid residues 4-178 of SEQ ID NO:8 which is encoded by nucleotides 10-534 of SEQ ID NO:7; amino acid residues 4-177 of SEQ ID NO:8 which is encoded by nucleotides 10-531 of SEQ ID NO:7; amino acid residues 4-176 of SEQ ID NO:8 which is encoded by nucleotides 10-528 of SEQ ID NO:7; amino acid residues 4-175 of SEQ ID NO:8 which is encoded by nucleotides 10-525 of SEQ ID NO:7; amino acid residues 4-174 of SEQ ID NO:8 which is encoded by nucleotides 10-522 of SEQ ID NO:7; amino acid residues 4-173 of SEQ ID NO:8 which is encoded by nucleotides 10-519 of SEQ ID NO:7; amino acid residues 4-172 of SEQ ID NO:8 which is encoded by nucleotides 10-516 of SEQ ID NO:7; amino acid residues 5-181 of SEQ ID NO:8 which is encoded by nucleotides 13-543 of SEQ ID NO:7; amino acid residues 5-180 of SEQ ID NO:8 which is encoded by nucleotides 13-540 of SEQ ID NO:7; amino acid residues 5-179 of SEQ ID NO:8 which is encoded by nucleotides 13-537 of SEQ ID NO:7; amino acid residues 5-178 of SEQ ID NO:8 which is encoded by nucleotides 13-534 of SEQ ID NO:7; amino acid residues 5-177 of SEQ ID NO:8 which is encoded by nucleotides 13-531 of SEQ ID NO:7; amino acid residues 5-176 of SEQ ID NO:8 which is encoded by nucleotides 13-528 of SEQ ID NO:7; amino acid residues 5-175 of SEQ ID NO:8 which is encoded by nucleotides 13-525 of SEQ ID NO:7; amino acid residues 5-174 of SEQ ID NO:8 which is encoded by nucleotides 13-522 of SEQ ID NO:7; amino acid residues 5-173 of SEQ ID NO:8 which is encoded by nucleotides 13-519 of SEQ ID NO:7; amino acid residues 5-172 of SEQ ED NO:8 which is encoded by nucleotides 13-516 of SEQ ID NO:7; amino acid residues 6-181 of SEQ ID NO:8 which is encoded by nucleotides 16-543 of SEQ ID NO:7; amino acid residues 6-180 of SEQ ID NO:8 which is encoded by nucleotides 16-540 of SEQ ID NO:7; amino acid residues 6-179 of SEQ ID NO:8 which is encoded by nucleotides 16-537 of SEQ ID NO:7; amino acid residues 6-178 of SEQ ID NO:8 which is encoded by nucleotides 16-534 of SEQ ID NO:7; amino acid residues 6-177 of SEQ ID NO:8 which is encoded by nucleotides 16-531 of SEQ ID NO:7; amino acid residues 6-176 of SEQ ID NO:8 which is encoded by nucleotides 16-528 of SEQ ID NO:7; amino acid residues 6-175 of SEQ ID NO:8 which is encoded by nucleotides 16-525 of SEQ ID NO:7; amino acid residues 6-174 of SEQ ID NO:8 which is encoded by nucleotides 16-522 of SEQ ID NO:7; amino acid residues 6-173 of SEQ ID NO:8 which is encoded by nucleotides 16-519 of SEQ ID NO:7; amino acid residues 6-172 of SEQ ID NO:8 which is encoded by nucleotides 16-516 of SEQ ID NO:7;

amino acid residues 7-181 of SEQ ID NO:8 which is encoded by nucleotides 19-543 of SEQ ID NO:7; amino acid residues 7-180 of SEQ ID NO:8 which is encoded by nucleotides 19-540 of SEQ ID NO:7; amino acid residues 7-179 of SEQ ID NO:8 which is encoded by nucleotides 19-537 of SEQ ID NO:7; amino acid residues 7-178 of SEQ ID NO:8 which is encoded by nucleotides 19-534 of SEQ ID NO:7; amino acid residues 7-177 of SEQ ID NO:8 which is encoded by nucleotides 19-531 of SEQ ID NO:7; amino acid residues 7-176 of SEQ ID NO:8 which is encoded by nucleotides 19-528 of SEQ ID NO:7; amino acid residues 7-175 of SEQ ID NO:8 which is encoded by nucleotides 19-525 of SEQ ID NO:7; amino acid residues 7-174 of SEQ ID NO:8 which is encoded by nucleotides 19-522 of SEQ ID NO:7; amino acid residues 7-173 of SEQ ID NO:8 which is encoded by nucleotides 19-519 of SEQ ID NO:7; amino acid residues 7-172 of SEQ ID NO:8 which is encoded by nucleotides 19-516 of SEQ ID NO:7; amino acid residues 8-181 of SEQ ID NO:8 which is encoded by nucleotides 22-543 of SEQ ID NO:7; amino acid residues 8-180 of SEQ ID NO:8 which is encoded by nucleotides 22-540 of SEQ ID NO:7; amino acid residues 8-179 of SEQ ID NO:8 which is encoded by nucleotides 22-537 of SEQ ID NO:7; amino acid residues 8-178 of SEQ ID NO:8 which is encoded by nucleotides 22-534 of SEQ ID NO:7; amino acid residues 8-177 of SEQ ID NO:8 which is encoded by nucleotides 22-531 of SEQ ID NO:7; amino acid residues 8-176 of SEQ ID NO:8 which is encoded by nucleotides 22-528 of SEQ ID NO:7; amino acid residues 8-175 of SEQ ID NO:8 which is encoded by nucleotides 22-525 of SEQ ID NO:7; amino acid residues 8-174 of SEQ ID NO:8 which is encoded by nucleotides 22-522 of SEQ ID NO:7; amino acid residues 8-173 of SEQ ID NO:8 which is encoded by nucleotides 22-519 of SEQ ID NO:7; amino acid residues 8-172 of SEQ ID NO:8 which is encoded by nucleotides 22-516 of SEQ ID NO:7; amino acid residues 9-181 of SEQ ID NO:8 which is encoded by nucleotides 25-543 of SEQ ID NO:7; amino acid residues 9-180 of SEQ ID NO:8 which is encoded by nucleotides 25-540 of SEQ ID NO:7; amino acid residues 9-179 of SEQ ID NO:8 which is encoded by nucleotides 25-537 of SEQ ID NO:7; amino acid residues 9-178 of SEQ ID NO:8 which is encoded by nucleotides 25-534 of SEQ ID NO:7; amino acid residues 9-177 of SEQ ID NO:8 which is encoded by nucleotides 25-531 of SEQ ID NO:7; amino acid residues 9-176 of SEQ ID NO:8 which is encoded by nucleotides 25-528 of SEQ ID NO:7; amino acid residues 9-175 of SEQ ID NO:8 which is encoded by nucleotides 25-525 of SEQ ID NO:7; amino acid residues 9-174 of SEQ ID NO:8 which is encoded by nucleotides 25-522 of SEQ ID NO:7; amino acid residues 9-173 of SEQ ID NO:8 which is encoded by nucleotides 25-519 of SEQ ID NO:7; amino acid residues 9-172 of SEQ ID NO:8 which is encoded by nucleotides 25-516 of SEQ ID NO:7; amino acid residues 10-181 of SEQ ID NO:8 which is encoded by nucleotides 28-543 of SEQ ID NO:7; amino acid residues 10-180 of SEQ ID NO:8 which is encoded by nucleotides 28-540 of SEQ ID NO:7; amino acid residues 10-179 of SEQ ID NO:8 which is encoded by nucleotides 28-537 of SEQ ID NO:7; amino acid residues 10-178 of SEQ ID NO:8 which is encoded by nucleotides 28-534 of SEQ ID NO:7; amino acid residues 10-177 of SEQ ID NO:8 which is encoded by nucleotides 28-531 of SEQ ID NO:7; amino acid residues 10-176 of SEQ ID NO:8 which is encoded by nucleotides 28-528 of SEQ ID NO:7; amino acid residues 10-175 of SEQ ID NO:8 which is encoded by nucleotides 28-525 of SEQ ID NO:7; amino acid residues 10-174 of SEQ ID NO:8 which is encoded by nucleotides 28-522 of SEQ ID NO:7; amino acid residues 10-173 of SEQ ID NO:8 which is encoded by nucleotides 28-519 of SEQ ID NO:7; amino acid residues 10-172 of SEQ ID NO:8 which is encoded by nucleotides 28-516 of SEQ ID NO:7; amino acid residues 11-181 of SEQ ID NO:8 which is encoded by nucleotides 31-543 of SEQ ID NO:7; amino acid residues 11-180 of SEQ ID NO:8 which is encoded by nucleotides 31-540 of SEQ ID NO:7; amino acid residues 11-179 of SEQ ID NO:8 which is encoded by nucleotides 31-537 of SEQ ID NO:7; amino acid residues 11-178 of SEQ ID NO:8 which is encoded by nucleotides 31-534 of SEQ ID NO:7; amino acid residues 11-177 of SEQ ID NO:8 which is encoded by nucleotides 31-531 of SEQ ID NO:7; amino acid residues 11-176 of SEQ ID NO:8 which is encoded by nucleotides 31-528 of SEQ ID NO:7; amino acid residues 11-175 of SEQ ID NO:8 which is encoded by nucleotides 31-525 of SEQ ID NO:7; amino acid residues 11-174 of SEQ ID NO:8 which is encoded by nucleotides 31-522 of SEQ ID NO:7; amino acid residues 11-173 of SEQ ID NO:8 which is encoded by nucleotides 31-519 of SEQ ID NO:7; amino acid residues 11-172 of SEQ ID NO:8 which is encoded by nucleotides 31-516 of SEQ ID NO:7; amino acid residues 12-181 of SEQ ID NO:8 which is encoded by nucleotides 34-543 of SEQ ID NO:7; amino acid residues 12-180 of SEQ ID NO:8 which is encoded by nucleotides 34-540 of SEQ ID NO:7; amino acid residues 12-179 of SEQ ID NO:8 which is encoded by nucleotides 34-537 of SEQ ID NO:7; amino acid residues 12-178 of SEQ ID NO:8 which is encoded by nucleotides 34-534 of SEQ ID NO:7; amino acid residues 12-177 of SEQ ID NO:8 which is encoded by nucleotides 34-531 of SEQ ID NO:7; amino acid residues 12-176 of SEQ ID NO:8 which is encoded by nucleotides 34-528 of SEQ ID NO:7; amino acid residues 12-175 of SEQ ID NO:8 which is encoded by nucleotides 34-525 of SEQ ID NO:7; amino acid residues 12-174 of SEQ ID NO:8 which is encoded by nucleotides 34-522 of SEQ ID NO:7; amino acid residues 12-173 of SEQ ID NO:8 which is encoded by nucleotides 34-519 of SEQ ID NO:7; amino acid residues 12-172 of SEQ ID NO:8 which is encoded by nucleotides 34-516 of SEQ ID NO:7; amino acid residues 13-181 of SEQ ID NO:8 which is encoded by nucleotides 37-543 of SEQ ID NO:7; amino acid residues 13-180 of SEQ ID NO:8 which is encoded by nucleotides 37-540 of SEQ ID NO:7; amino acid residues 13-179 of SEQ ID NO:8 which is encoded by nucleotides 37-537 of SEQ ID NO:7; amino acid residues 13-178 of SEQ ID NO:8 which is encoded by nucleotides 37-534 of SEQ ID NO:7; amino acid residues 13-177 of SEQ ID NO:8 which is encoded by nucleotides 37-531 of SEQ ID NO:7; amino acid residues 13-176 of SEQ ID NO:8 which is encoded by nucleotides 37-528 of SEQ ID NO:7; amino acid residues 13-175 of SEQ ID NO:8 which is encoded by nucleotides 37-525 of SEQ ID NO:7; amino acid residues 13-174 of SEQ ID NO:8 which is encoded by nucleotides 37-522 of SEQ ID NO:7; amino acid residues 13-173 of SEQ ID NO:8 which is encoded by nucleotides 37-519 of SEQ ID NO:7; amino acid residues 13-172 of SEQ ID NO:8 which is encoded by nucleotides 37-516 of SEQ ID NO:7; amino acid residues 14-181 of SEQ ID NO:8 which is encoded by nucleotides 40-543 of SEQ ID NO:7; amino acid residues 14-180 of SEQ ID NO:8 which is encoded by nucleotides 40-540 of SEQ ID NO:7; amino acid residues 14-179 of SEQ ID NO:8 which is encoded by nucleotides 40-537 of SEQ ID NO:7; amino acid residues 14-178 of SEQ ID NO:8 which is encoded by nucleotides 40-534 of SEQ ID NO:7; amino acid residues 14-177 of SEQ ID NO:8 which is encoded by nucleotides 40-531 of SEQ ID NO:7; amino acid residues 14-176 of SEQ ID NO:8 which is encoded by nucleotides 40-528 of SEQ ID NO:7; amino acid residues 14-175 of SEQ ID NO:8 which is encoded by nucleotides 40-525 of SEQ ID NO:7; amino acid residues 14-174 of SEQ ID NO:8 which is encoded by nucleotides 40-522 of SEQ ID NO:7; amino acid residues 14-173 of SEQ ID NO:8 which is encoded by nucleotides 40-519 of SEQ ID NO:7; amino acid residues 14-172 of SEQ ID NO:8 which is encoded by nucleotides 40-516 of SEQ ID NO:7; amino acid residues 15-181 of SEQ ID NO:8 which is encoded by nucleotides 43-543 of SEQ ID NO:7; amino acid residues 15-180 of SEQ ID NO:8 which is encoded by nucleotides 43-540 of SEQ ID NO:7; amino acid residues 15-179 of SEQ ID NO:8 which is encoded by nucleotides 43-537 of SEQ ID NO:7; amino acid residues 15-178 of SEQ ID NO:8 which is encoded by nucleotides 43-534 of SEQ ID NO:7; amino acid residues 15-177 of SEQ ID NO:8 which is encoded by nucleotides 43-531 of SEQ ID NO:7; amino acid residues 15-176 of SEQ ID NO:8 which is encoded by nucleotides 43-528 of SEQ ID NO:7; amino acid residues 15-175 of SEQ ID NO:8 which is encoded by nucleotides 43-525 of SEQ ID NO:7; amino acid residues 15-174 of SEQ ID NO:8 which is encoded by nucleotides 43-522 of SEQ ID NO:7; amino acid residues 15-173 of SEQ ID NO:8 which is encoded by nucleotides 43-519 of SEQ ID NO:7; amino acid residues 15-172 of SEQ ID NO:8 which is encoded by nucleotides 43-516 of SEQ ID NO:7; amino acid residues 16-181 of SEQ ID NO:8 which is encoded by nucleotides 46-543 of SEQ ID NO:7; amino acid residues 16-180 of SEQ ID NO:8 which is encoded by nucleotides 46-540 of SEQ ID NO:7; amino acid residues 16-179 of SEQ ID NO:8 which is encoded by nucleotides 46-537 of SEQ ID NO:7; amino acid residues 16-178 of SEQ ID NO:8 which is encoded by nucleotides 46-534 of SEQ ID NO:7; amino acid residues 16-177 of SEQ ID NO:8 which is encoded by nucleotides 46-531 of SEQ ID NO:7; amino acid residues 16-176 of SEQ ID NO:8 which is encoded by nucleotides 46-528 of SEQ ID NO:7; amino acid residues 16-175 of SEQ ID NO:8 which is encoded by nucleotides 46-525 of SEQ ID NO:7; amino acid residues 16-174 of SEQ ID NO:8 which is encoded by nucleotides 46-522 of SEQ ID NO:7; amino acid residues 16-173 of SEQ ID NO:8 which is encoded by nucleotides 46-519 of SEQ ID NO:7; and amino acid residues 16-172 of SEQ ID NO:8 which is encoded by nucleotides 46-516 of SEQ ID NO:7. The N-terminally and C-terminally modified biologically active mutants of IL-29 C1 mutants of the present invention may also include an N-terminal methione if expressed, for instance, in E. coli.

The IL-29 polypeptides of the present invention include, for example, SEQ ID NOs: 2, 4, 6, 8, 10 and 12, which are encoded by IL-29 polynucleotide molecules as shown in SEQ ID NOs: 1, 3, 5, 7, 9 and 11, respectively, fragments, mutants (including biologically active N-terminal, C-terminal and N- and C-terminal mutants), variants and fusions thereof.

Expression of Recombinant IL-29

The present invention provides expression vectors and methods for producing and purifying recombinant IL-29 protein from a prokaryotic host. IL-29 was previously designated zcyto21 (IL-29 and zcyto21 are used interchangeably herein), and is fully described in commonly assigned U.S. Pat. No. 6,927,040, U.S. Pat. No. 7,038,032, WO 04/037995, WO 05/023862, U.S. Patent Publication No. 2005-0244423, U.S. Patent Publication No. 2006-012644, U.S. patent application Ser. No. 11/458,945, and U.S. patent application Ser. No. 11/489,894, all of which are herein incorporated by reference in their entirety. In particular, the expression vectors and methods of the present invention comprise an E. coli expression system for the large scale production of IL-29 utilizing an IL-29 coding sequence with specific changes in nucleotides in order to optimize codons and mRNA secondary structure for translation in E. coli. Using the expression vectors and growth conditions as described herein significantly improved the yield of recombinant protein recovered from the bacteria. In another embodiment, to facilitate the development of high cell density fed-batch fermentation, another E. coli strain, W3110, was selected as a host for the large scale production of IL-29. This host strain is non-pathogenic and can grow to high cell density in minimally defined fermentation media.

The present invention also provides methods for recovering recombinant IL-29 protein from a prokaryotic host when the IL-29 protein is expressed by the host and found within the host cell as an unglycosylated, insoluble inclusion body. When the prokaryotic cell is lysed to isolate the inclusion bodies (also called refractile bodies), the inclusion bodies are aggregates of IL-29. Therefore, the inclusion bodies must be disassociated and dissolved to isolate the IL-29 protein, and generally this requires the use of a denaturing chaotropic solvent, resulting in recovering a polypeptide that must be refolded to have significant biological activity. Once the IL-29 protein is refolded, the protein must be captured and purified. Thus, the present invention provides for methods for isolating insoluble IL-29 protein from prokaryotic cells, dissolving the insoluble IL-29 protein material in a chaotropic solvent, diluting the chaotropic solvent in such a manner that the IL-29 protein is refolded and isolated. The present invention also includes methods for capturing the renatured IL-29 protein from the dilute refold buffer using cation exchange chromatography, and purifying the refolded IL-29 protein using hydrophobic interaction chromatography ("HIC"). Further purification is achieved using high performance cation exchange chromatography to remove charged variants from the recombinant IL-29 solution.

The IL-29 DNA coding sequence as used herein comprises the mature human gene, i.e., no signal sequence. The DNA sequence was synthesized to reflect E. coli codon bias, and a methionine was added to the N-terminus of the mature protein for translation initiation.

An optimal E. coli production host should 1) be non-pathogenic; 2) express the target protein well; 3) maintain stability of the expression vector; and 4) grow well in defined, minimal fermentation media. E. coli strain W3110, for example, can be used as the host for production of recombinant protein because it fulfills these requirements. W3110 is a prototrophic derivative of K-12. This strain was isolated in early 1950s by Dr Joshua Lederberg and his research team at the University of Wisconsin. Like other K-12 derivatives, E. coli strain W3110 does not survive in non-sterile water, soil, or sewage (Smith H W, Infect Dis. 1978 May; 137(5):655-660; Bogosian G. et al., Adv Appl Microbiol. 1991; 36:87-131; Bogosian G. et al., Appl Environ Microbial. 1996 November; 62(11):4114-20; Heitkamp M. A. et al., J Ind Microbial. 1993 July; 11(4):243-52; Bogosian G. et al., J Ind Microbiol. 1993 July; 11(4):235-41; Bogosian G. et al., J Ind Microbiol. 1992 January; 9(1):27-36). Furthermore, this strain is unable to adhere to mammalian intestinal cells and does not colonize the mammalian intestinal tract. Based on these findings, W3110 is considered non-pathogenic and unlikely to survive in mammalian tissues and cause disease. Additionally, W3110 has been used extensively as a host for protein production (Kane J. F. et al., Trends Biotechnol., 6:95-101; and Kane J. F. et al, In: Surface reactive peptides and polymers: discovery and commercialization (C S Sikes and A P Wheeler, eds.) American Chemical Society Books, Washington, D.C.) and grows to very high density in a fed-batch fermentation process.

OmpT is a perisplasmic endopeptidase that cleaves specifically between two consecutive basic residues and is active under denaturing conditions such as 8 M urea and 6M guanidine-HCl (White C. B. et al., *J Biol. Chem.*, 1995 Jun. 2; 270(22):12990-4; and Dekker N. et al., *Biochemistry.* 2001 Feb. 13; 40(6):1694-701). OmpT has been associated with the degradation of recombinant proteins expressed as inclusion bodies in *E. coli*. While W3110 is a robust host for fermentation and expression of the protein, it is not ideal for downstream processing of IL-29. Once the cells are lysed, the OmpT protease may cleave the recombinantly-produced protein.

*E. coli* is susceptible to infection by T-odd bacteriophage which may result in slowed growth or failed fermentations (Ogata S. et al., *Uirusu.* 2000 June; 50(1):17-26). This can have serious economic consequences. The ferrichrome-iron receptor encoded by the fhuA gene of *E. coli* K-12 is a multifunctional outer membrane receptor required for the binding and uptake of ferrichrome and serves as the attachment site for T-odd bacteriophage. Antibodies against the carboxyl terminus of the fhuA gene product can prevent infection by bacteriophage T5 (Moeck G. S. et al., *J Bacteriol.* 1995 November; 177(21):6118-25).

In order to streamline the process for production of IL-29, the ompT and fhuA genes have been removed from the host strain W3110 by homologous recombination (Datsenko K A, Wanner B L. One-step inactivation of chromosomal genes in *Escherichia coli* K-12 using PCR products. *Proc. Natl. Acad Sci USA.* 2000 Jun. 6; 97(12):6640-5; Murphy K C, Campellone K G, Poteete A R. PCR-mediated gene replacement in *Escherichia coli. Gene.* 2000 Apr. 4; 246(1-2):321-30; and Yu D, Ellis H M, Lee E C, Jenkins N A, Copeland N G, Court D L. An efficient recombination system for chromosome engineering in *Escherichia coli. Proc Natl Acad Sci USA.* 2000 May 23; 97(11):5978-83.). This newly developed host strain is known as ZGOLD5 (more fully described below).

Examplary production strains of the present invention consist of various *E. coli* host strains carrying different expression vectors. For example, *E. coli* W3110 stably maintains the kanamycin-selectable plasmid for IL-29 expression. W3110 has the genotype F– IN(rrnD⁻ rrnE)1 lambda⁻. ZGOLD1 [F– IN(rrnD⁻ rrnE)1 lambda⁻ ΔompT::tet] is an ΔompT mutant derived from W3110. ZGOLD5 [F– IN(rrnD⁻ rrnE)1 lambda⁻ ΔompT::tet ΔfhuA::Cm] is a ΔfhuA mutant derived from ZGOLD1 (W3110). F⁻ denotes lack of the endogenous *E. coli* F plasmid (New England Biolabs 2005-6 Catalog, page 270). IN(rrnD⁻ rrnE)1 denotes an inversion at the chromosomal loci containing the rrnD and rrnE operons (Hill C W and Gray J W, *Genetics.,* 1988 August; 119(4):771-778). The number 1 indicates that this is the first reported allele of this inversion. This chromosomal rearrangement is predicted to have no effect on production of IL-29. rph1 is a 1 bp deletion that results in a frame shift over the last 15 codons in RNase PH, the protein that removes nucleotides from the 3' ends of tRNA precursors. This lesion exerts a polar effect on the adjacent pyrE gene, which encodes orotate phosphoribosyltransferase. This leads to starvation for pyrimidine on minimal medium. This partial auxotrophy, however, can be readily compensated for by supplementing the media. ilvG is a gene that codes for a subunit of acetolactate synthase H and acetohydroxybutanoate synthase II. These enzymes are involved in valine/leucine and isoleucine biosynthesis pathways, respectively. The ilvG gene of K12 derivatives, including W3110 and ZGOLD5, contain a polar frameshift in the middle of the gene causing premature polypeptide chain termination (Parekh B S and Hatfield G W, *J Bacteriol.,* 1997 March; 179(6):2086-2088). This truncated protein is sensitive to valine and experiences feedback inhibition when valine is present. The pathways leading to the synthesis of isoleucine and valine are shut down in the presence of valine even if the cell is starved for isoleucine. The mixed feed, which includes yeast extract, compensates for the strain's inability to produce isoleucine in the presence of valine. λ—indicates the absence of bacteriophage λ sequences in the lysogenic or lytic state. ompT codes for a periplasmic endopeptidase that cleaves between two consecutive base residues (White et al., *J Biol. Chem.,* 1995 Jun. 2; 270(22):12990-4; and Dekker et al., *Biochemistry.* 2001 Feb. 13; 40(6):1694-701). The ompT gene was removed from this strain to eliminate any potential degradation by OmpT (RES-10544). fhuA codes for a multifunctional outer membrane protein involved in the binding and uptake of ferrichrome and the attachment of T-odd phage (Ogata et al., *Uirusu.* 2000 June; 50(1):17-26; and Moeck et al., *J Bacteriol.,* 1995 November; 177(21):6118-25). The gene was removed to prevent the infection of the strain by T-odd phage, especially in fermentation tanks.

Expression vectors that are suitable for production of a desired protein in prokaryotic cells typically comprise (1) prokaryotic DNA elements coding for a bacterial origin for the maintenance of the expression vector in a bacterial host; (2) DNA elements that control initiation of transcription, such as a promoter; (3) DNA elements that control the processing of transcripts, such as a transcriptional terminator, and (4) a gene encoding a selectable marker, such as antibiotic resistance. The prokaryotic host cell produces IL-29 upon introduction of an expression vector and addition of an appropriate inducer. Accordingly, the present invention contemplates expression vectors comprising a promoter, the IL-29 optimized polynucleotide sequence, and a terminator sequence. Exemplary optimized IL-29 polynucleotide sequence are shown in SEQ ID NOs: 1, 3, 5, 7, 9 and 11. In another embodiment, the expression vector further comprises a selectable marker. In one embodiment, the selectable marker is kanamycin resistance.

Expression vectors can also comprise polynucleotide sequences that encode a peptide tag to aid in purification of the desired protein. Peptide tags that are useful for isolating recombinant polypeptides include, for example, polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329: 215 (1996), Morganti et al, *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

One of ordinary skill in the art will be familiar with a multitude of molecular techniques for the preparation of the expression vector. For example, the IL-29 polynucleotide can be prepared by synthesizing nucleic acid molecules using mutually priming, long oligonucleotides and the nucleotide sequences described herein (see, for example, Ausubel et al., *Short Protocols in Molecular Biology,* 3$^{rd}$ Edition, John Wiley & Sons, at page 4s 8-8 to 8-9 (1995)). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology,* Vol. 15: *PCR Protocols: Current Methods and Applications,* White (ed.), pages 263-268, (Humana Press, Inc. 1993), and Holowachuk et al., *PCR Methods Appl.* 4:299 (1995)).

Another method for constructing expression systems utilizes homologous recombination using a yeast system. See U.S. Pat. No. 6,207,442, Plasmid Construction by Homologous Recombination, incorporated herein by reference. The system provides a universal acceptor plasmid that can be used to clone a DNA encoding any polypeptide of interest, including polypeptide fusions. The system provides methods for preparing double stranded, circular DNA molecules comprising a region encoding a protein of interest. One or more donor DNA fragments encoding the protein of interest, i.e., IL-29, are combined with an acceptor plasmid, a first DNA linker, and a second DNA linker in a *Saccharomyces cerevisiae* host cell whereby the donor DNA fragment is joined to the acceptor plasmid by homologous recombination of the donor DNA, acceptor plasmid, and linkers to form the closed, circular plasmid.

A nucleic acid molecule of the present invention can also be synthesized with "gene machines" using protocols such as the phosphoramidite method. If chemically-synthesized, double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes (>300 base pairs), however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

Examples of alternate techniques that can be used to prepare the IL-29 gene and expression vector include, for example, restriction endonuclease digestion and ligation, and polymerase chain reaction, all of which are well known in the art.

A wide variety of selectable marker genes is available (see, for example, Kaufman, *Meth. Enzymol.* 185:487 (1990); Kaufman, *Meth. Enzymol.* 185:537 (1990)). It is common for expression vectors to comprise selection markers, such as tetracycline resistance, amplicillin resistance, kanamycin resistance, neomycin resistance, or chlormaphenicol resistance. A selectable marker will permit selection and/or detection of cells that have been transformed with expression vector from cells that have not been transformed. An expression vector can carry more than one such antibiotic resistance gene. An example of selectable marker without antibiotic resistance uses the hok/sok system from plasmid R1. The hok gene encodes the toxic Hok protein of 52 amino acids and the sok gene encodes an antisense RNA, which is complementary to the hok mRNA leader sequence. This selectable marker is known to one skilled in the art and is described in more detail by Gerdes, K. et al., *Genetic Engineering*, 19:49-61, 1997.

A wide variety of suitable recombinant host cells is encompassed by the present invention and includes, but is not limited to, gram-negative prokaryotic host organisms. Suitable strains of *E. coli* include W3110, K12-derived strains MM294, TG-1, JM-107, BL21, and UT5600. Other suitable strains include: BL21(DE3), BL21(DE3)pLysS, BL21(DE3) pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, ER1647, *E. coli* K12, *E. coli* K12 RV308, *E. coli* K12 C600, *E. coli*HB101, *E. coli* K12 C600 R.sub.k-M.sub.k-, *E. coli* K12 RR1 (see, for example, Brown (ed.), *Molecular Biology Labfax* (Academic Press 1991)). Other gram-negative prokaryotic hosts can include *Serratia, Pseudomonas, Caulobacter*. Prokaryotic hosts can include gram-positive organisms such as *Bacillus*, for example, *B. subtilis* and *B. thuringienesis*, and *B. thuringienesis* var. *israelensis*, as well as *Streptomyces*, for example, *S. lividans, S. ambofaciens, S. fradiae*, and *S. griseofuscus*. Suitable strains of *Bacillus subtilis* include BR151, YB886, MI119, MI120, and B170 (see, for example, Hardy, "Bacillus Cloning Methods," in *DNA Cloning: A Practical Approach*, Glover (ed.) (IRL Press 1985)). Standard techniques for propagating vectors in prokaryotic hosts are well-known to those of skill in the art (see, for example, Ausubel et al. (eds.), *Short Protocols in Molecular Biology*, 3$^{rd}$ Edition (John Wiley & Sons 1995); Wu et al., *Methods in Gene Biotechnology* (CRC Press, Inc. 1997)). For an overview of protease deficient strains in prokaryotes, see, Meerman et al., *Biotechnology* 12:1107-1110, 1994.

Techniques for manipulating cloned DNA molecules and introducing exogenous DNA into a variety of host cells are disclosed by Sambrook et al., Molecular Cloning: *A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987. Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient that is complemented by the selectable marker carried on the expression vector or co-transfected into the host cell. Liquid cultures are provided with sufficient aeration by conventional means, such as shaking of small flasks or sparging of fermentors. Transformed cells can be selected and propagated to provide recombinant host cells that express the gene of interest. IL-29 can be expressed in *E. coli* using the MBP (maltose binding protein) fusion system (New England Biolabs (NEB; Beverly, Mass.)). In this system, the IL-29 cDNA is attached to the 3' end of the malE gene to form an MBP-IL-29 fusion protein. Fusion protein expression is driven by the tac promoter and is "off" until the promoter is induced by addition of 1 mM IPTG (isopropyl b-thiogalactosylpyranoside). The constructs can be built as in-frame fusions with MBP in accordance with the Multiple Cloning Site (MCS) of the pMAL-c2 vector (NEB), and according to the manufacturer's specifications.

An *E. coli* expression vector has been constructed that contains a codon optimized gene coding for human IL-29. This vector (pSDH175) vector contains the following functional elements: a lacI repressor, tac promoter, G10 translational enhancer, SmaI cloning site, transcriptional terminator, Kanamycin selectable marker, and a pMB1 origin of replication and ROB gene. All of the plasmid numbers (vectors), as indicated in below Table 1 contain the same functional elements as the pSDH175 vector, but for the indicated substitutions of the translational enhancer. The particular IL-29 molecule expressed by the various plasmids or vectors of Table 1 is also indicated in the IL-29 construct column. A number of changes to the protein structure of IL-29 were made to enhance expression or improve refolding. The cysteine in position 172 of the wild type IL-29 protein (SEQ ID NO:12) was changed to a serine (SEQ ID NO:2 or C172S) and the resulting expression vector was labeled pSDH177. The G10 translational enhancer of pSDH177 was replaced with the Zymo2 vector (SEQ ID NO:13) and this vector was labeled pCHAN15. The amino acids in position 2-7 of SEQ ID NO:2 were deleted from the pCHAN15 vector to form the pTAP440 vector encoding this alternative form of IL-29 as shown in SEQ ID NO:6. The polypeptide of SEQ ID NO:6 is also referred herein as IL-29 C172S d2-7 or C172S d2-7. In vector pTAP438, a leucine was inserted into position 2, behind the N-terminal methionine of SEQ ID NO:2 and is shown as SEQ ID NO:4. The polypeptide of SEQ ID NO:4 is also referred to herein as IL-29 C172S Leu Insert or C172S Leu Insert. These vectors were transformed into a number of host strains to form the expression strains listed in Table 1 below. Recombinant human IL-29 has been produced in fed batch fermentations using a number of *E. coli* production hosts and vectors. The IL-29 is produced as insoluble, refractile inclusion bodies in the different *E. coli* host strains used.

TABLE 1

| Production Strain | Host Strain | Plasmid Number | Translational enhancer | IL-29 construct |
|---|---|---|---|---|
| EE669 | W3110 | pSDH175 | G10 | Codon optimized wildtype (SEQ ID NO: 11) |
| EE675 | W3110 | pSDH177 | G10 | Codon optimized C172S (SEQ ID NO: 1) |
| EE698 | W3110 | pSDH 188 | RBS2 ribosome-binding site | Codon optimized C172S (SEQ ID NO: 1) |
| EE826 | W3110 | pTAP440 | Zymo2 | C172S d2-7. Codon optimized (SEQ ID NO: 5) |
| EE708 | ZGOLD1 | pSDH188 | RBS2 ribosome-binding site | Codon optimized C172S (SEQ ID NO: 1) |
| EE733 | ZGOLD1 | pCHAN15 | Zymo2 | Codon optimized C172S (SEQ ID NO: 1) |
| EE833 | ZGOLD1 | pTAP440 | Zymo2 | C172S d2-7. Codon optimized (SEQ ID NO: 5) |
| EE831 | ZGOLD1 | pTAP438 | Zymo2 | C172S Leu Insert (SEQ ID NO: 3) |
| EE867 | ZGOLD5 | pTAP440 | Zymo2 | C172S d2-7. Codon optimized. (SEQ ID NO: 5) |
| EE870 | ZGOLD5 | pCHAN15 | Zymo2 | Codon optimized C172S (SEQ ID NO: 1) |

High IL-29 expression levels have been obtained using *E. coli* ZGOLD5 (EE867) cells, described below, containing the expression vector pTAP440. A number of fed batch fermentation methods have been developed for the production of IL-29 using this strain. Either a one stage or two stage seeding method can be used to start the fermentations. The seed medium is a defined recipe (ZSM), described below in Table 2, containing 2% glucose and is inoculated using vials from a working cell bank (WCB). The fermentation is started with an inoculum from an overnight (16-18 hours) culture grown in ZSM. The production medium (PCOL18) is a defined salts medium containing 1-2% glucose, 1% soy hydrolysate and 0.5% yeast extract. The initial batch phase is run for 7-8 hours, followed by glucose only feeding for the next 12 hours. The feed rate is maintained constant throughout the fermentation. The IL-29 expression is induced by addition of isopropyl thiogalactopyranoside (IPTG) to a final concentration of 1 mM at 24 hours elapsed fermentation time (EFT). Total fermentation time is about 48 hours.

TABLE 2

| ZSM seed medium recipe per liter medium | |
|---|---|
| Ingredient | Amount |
| Yeast Extract | 5.0 g |
| Sodium Sulfate dibasic | 2.0 g |
| Ammonium Sulfate dibasic | 2.5 g |
| Ammonium Chloride | 0.5 g |
| Potassium Phosphate dibasic | 14.6 g |
| Potassium Phosphate monobasic | 3.6 g |
| Deionized water | QS to 1.0 L |
| After autoclaving add: | |
| 60% Glucose (wt/v) | 33 mL |
| Trace Elements Solution | 3 mL |
| 1M MgSO4 | 3 mL |
| Kanamycin (25 mg/mL stock concentration) | 1.0 mL |

Fermentation

In one embodiment of the present invention batch fermentation can be used, particularly when large scale production of IL-29 using the expression system of the present invention is required. Generally, batch fermentation comprises that a first stage seed flask is prepared by growing *E. coli* strains expressing IL-29 in a suitable medium in shake flask culture to allow for growth to an optical density (OD) of 5 to 20 at 600 nm. A suitable medium contains nitrogen from a source(s) such as ammonium sulfate, ammonium phosphate, ammonium chloride, yeast extract, hydrolyzed animal proteins, hydrolyzed plant proteins or hydrolyzed caseins. Phosphate will be supplied from potassium phosphate, ammonium phosphate, phosphoric acid or sodium phosphate. Other components of the medium include magnesium chloride or magnesium sulfate, ferric sulfate or ferric chloride, and other trace elements. Growth medium can be supplemented with carbohydrates, such as fructose, glucose, galactose, lactose, and glycerol, to improve growth.

A first stage seed flask is prepared as follows: The IL-29 producing *E. coli* strains (e.g., W3110, ZGold1 and ZGold5) are grown in a suitable medium in shake flask culture to allow for growth to an optical density (OD) of between 5 and 20 at 600 nm. A suitable medium can be, for example: Super Broth II, APS-Super Broth, or ZSM. Growth medium can be supplemented with carbohydrates to improve growth. The preferred carbohydrate additions can be, for example, glycerol or glucose added from 1 to 20 g/L medium with a preference between 10-20 g/L. Growth is started by inoculating a shake flask (baffled flask from 500 ml to 3000 ml) containing a preferred growth medium with *E. coli* containing kanamycin (10-50 ug/ml) from a frozen stock culture. Growth in the shake flasks is at a temperature between 28 and 40° C. with a preference for growth between 30 and 37° C. The flasks are incubated with agitation set between 200 and 300 rpm.

A. Fed Batch Culture—Glucose Only Feeding (PCOL001 or PCOL0013)

Fermentation vessels are prepared with a suitable growth medium (for example, see Table 3 below) and sterilized. The pH of the medium is adjusted to a pH between 6.2 and 7.2 with a preference for about pH 6.8. Growth medium can be supplemented with carbohydrates to improve growth. The preferred carbohydrate additions would be glycerol or glucose added from 10 to 30 g/L medium with a preference between 10-20 g/L. The vessels are set to the proper aeration and agitation levels and inoculated from a first stage seed flask culture or $2^{nd}$ stage seed vessel that has been grown between 10 and 20 hours and has an OD between 5 and 20 at 600 nm. The inoculation level is between 1 and 5% (on a volume/volume basis) with a preference between 1 and 2% v/v. The dissolved oxygen level is maintained above 20% saturation by increasing agitation speed, increasing the aeration rate, sparging in oxygen or various combinations thereof.

A carbohydrate solution is fed into the fermentor at a pre-determined rate starting after 6-8 hours elapsed fermentation time (EFT). The feeding should be started no longer than 10 hours EFT. The feed is continued until the end of the fermentation. The feed solutions (glycerol or glucose) are prepared at 40-70% w/v with a preference for 50% glucose (w/v). Feed rates can vary between 5-15 grams of glucose or glycerol per liter per hour, with a preference between 8-10 g/l/hr (starting volume). At a time between 20 and 30 hours EFT with a preference of 24 hours, IPTG is added to the culture to a concentration of 1 mM. At a time between 48 and 56 hours EFT, the fermentation is harvested.

TABLE 3

PCOL13 Medium Recipe per Liter Medium

| Ingredients prior to autoclavation | Amount |
|---|---|
| Yeast extract | 5.0 g |
| (NH4)2SO4 | 9.9 g |
| KH2PO4 | 1.75 g |
| K2HPO4 | 12.25 g |
| Antifoam AF204 | 0.1 mL |
| Deionized water | QS to 0.92 L |
| Post Sterilization additives: | |
| 1M MgSO4 | 10.0 mL |
| Trace Elements Solution | 34.0 mL |
| 60% Glucose (wt/vol) | 33 mL |
| 1M CaCl2 | 1 mL |
| Kanamycin (25 mg/mL stock concentration) | 1 mL |

B. Fed Batch Culture—Glucose Only Feeding (PCOL0013+ Additives)

Fermentation vessels are prepared with a suitable growth medium (for example, see Table 3 above) and sterilized. The pH of the medium is adjusted to a pH between 6.2 and 7.2 with a preference for about pH 6.8. Growth medium can be supplemented with carbohydrates to improve growth. The preferred carbohydrate additions would be glycerol or glucose added from 10 to 30 g/L medium with a preference between 10-20 g/L. Growth medium can be supplemented with proteins to improve growth. The preferred protein additions are soy peptone and/or yeast extract added from 5 to 30 g/L medium with a preference between 5-10 g/L. The vessels are set to the proper aeration and agitation levels and inoculated from a first stage seed flask culture or $2^{nd}$ stage seed vessel that has been grown between 10 and 20 hours and has an OD between 5 and 20 at 600 nm. The inoculation level is between 1 and 5% (v/v) with a preference between 1 and 2% v/v. The dissolved oxygen level is maintained above 20% saturation by increasing agitation speed, increasing the aeration rate, sparging in oxygen or various combinations.

A carbohydrate solution is fed into the fermentor at a pre-determined rate starting after 6-8 hours elapsed fermentation time (EFT). The feeding needs to be started no longer than 10 hours EFT. The feed is continued until the end of the fermentation. The feed solutions (glycerol or glucose) are prepared at 40-70% w/v with a preference for 50% glucose (w/v). Feed rates to can vary between 5-15 grams of glucose or glycerol per liter per hour, with a preference between 8-10 g/l/hr (starting volume). At a time between 20 and 30 hours EFT with a preference of 24 hours, IPTG is added to the culture to a concentration of 1 mM. At a time between 48 and 56 hours EFT, the fermentation is harvested.

C. Fed Batch Culture—Mixed Feed (PCOL18)

Fermentation vessels are prepared with a suitable growth medium and sterilized. The pH of the medium is adjusted to a pH between 6.2 and 7.2 with a preference for about pH 6.8. Growth medium can be supplemented with carbohydrates to improve growth. The preferred carbohydrate additions would be glycerol or glucose added from 10 to 30 g/L medium with a preference between 10-20 g/L. The vessels are set to the proper aeration and agitation levels and inoculated from a first stage seed flask culture or $2^{nd}$ stage seed vessel that has been grown between 10 and 20 hours and has an OD between 5 and 20 at 600 nm. The inoculation level is between 1 and 5% (v/v) with a preference between 1 and 2% v/v. The dissolved oxygen level is maintained above 20% saturation by increasing agitation speed, increasing the aeration rate, sparging in oxygen or various combinations.

A carbohydrate solution is fed into the fermentor at a pre-determined rate starting after 6-8 hours elapsed fermentation time (EFT). The feeding needs to be started no longer than 10 hours EFT. The feed solutions (glycerol or glucose) are prepared at 40-70% w/v with a preference for 50% glucose (w/v). Feed rates to be used can vary between 5-15 grams of glucose or glycerol per liter per hour, with a preference between 8-10 g/l/hr. At a time between 20 and 30 hours EFT with a preference of 24 hours, IPTG is added to the culture to a concentration of 1 mM. At a time between 20 and 30 hours EFT with a preference of 24 hours the glucose feed rate is decreased to 2-6 g/L/hr feed. A second feed containing yeast extract (20-30-% w/w) with a preference for 25% (w/w) is started at a rate between 2-6 g/L/hr with a preference for 2 g/L/hr. At a time between 48 and 56 hours EFT, the fermentation is harvested.

IL-29 Recovery

Following fermentation the cells are harvested by centrifugation, re-suspended in deionized water and homogenized in an APV-Gaulin homogenizer or other type of cell disruption equipment. Alternatively, the cells are taken directly from the fermentor, deionized water is added, and then homogenized in an APV-Gaulin homogenizer. The homogenate is then centrifuged (either continuous or batch-mode), and the pellet containing the inclusion bodies is obtained after decanting the supernatant. The inclusion body pellet is then washed in water, or Tris buffers with or without varying levels of the following compounds: sodium chloride, urea, Triton X-100, sodium lauryl sulfate.

A. Homogenization and Pellet Washing (Direct Homogenization)

At the end of the fermentation run the temperature is adjusted downward to between 4 and 20° C. The fermentation broth is harvested from the vessel and collection of the broth through the sample port. Alternatively, the broth can be pumped out through one of the sample ports. The fermentation broth can contain between 10-30% solids.

A homogenizer is used to disrupt the E. coli cells, but bead mills and sonicators can also be used. A homogenizer (APV-Gaulin 1000, APV 2000, or Niro Soavi) should be chilled to 4-15° C. prior to use. An equal amount of chilled deionized water is added to the fermentation broth. The fermentation broth is passed through the homogenizer and the cell suspension is collected into a chilled container. The homogenizer pressure should be set between 8700-11,600 pounds per square inch ("psi") (600-800 bar) for maximum cell disruption. The suspension is passed through the homogenizer between 1-5 passes with a preference of 3 passes.

B. Batch Harvest and Inclusion Body Washing

At the end of the homogenization process the disrupted cells are transferred to 1 L centrifuge bottles, placing 0.75-1.0 L in each. A Beckman J6MI centrifuge with KompSpin KAJ7.100 rotor at 7,500 to 16,000×G can be used to harvest the pellet. The Beckman Avanti JHC centrifuge with the Beckman JLA-8.1 fixed angle rotor (7,500 to 16,000×G) or the Aries JS 5.0 Swinging Bucket rotor with 2.25 L bottles at 7,500 to 16,000×G can be used as well.

The bottles are centrifuged at 4° C. for 30 minutes. A centrifugation force of 7500 to 16,000×G is used. The culture broth or supernatant is poured off. Deionized water or buffer containing various additives is added to the pellets. Additives can be Triton X 100 (0.1-5%), sodium chloride (10-500 mM), zinc chloride (1-10 mM), EDTA (1-10 mM), sucrose (10-500 mM), sodium lauryl sulfate (0.1-2.0%) or urea (1-8 M). The wash solution is added in an equal volume to the supernatant decanted. The pellets are re-suspended into the liquid by mixing with a spatula followed by mixing with a motorized mixing device such as the Omni EZ homogenizer. Mixing is performed until the IB pellet is well suspended. The solution is centrifuged at 7500-16,000×G, 4° C. for 30 minutes. The broth from the cell pellet is poured off and add water or buffer is added to the pellets. After pellet re-suspension, the centrifugation step is repeated and the supernatant poured off. This process can be repeated as many times as needed.

C. Continuous Cell Harvest and Inclusion Body Washing

At the end of the homogenization process the disrupted cells are transferred to a chilled hold tank. The solution is passed through an appropriate continuous centrifuge such as a Carr or Westfalia disc stack centrifuge. The solution can be passed through at feed rates between 1-200 L per hour depending on the centrifuge used. The centrifugal force of the centrifuge should be between 7,500 and 15,000×G. For non-discharging centrifuges such as a Carr Biopilot or Sharpies clarifier, the solution is passed through the centrifuge and the pellets collected into the bowl. The inclusion body paste is scraped out of the bowl. The pellets can be used as is or re-diluted and passed through the centrifuge again. The supernatant is discarded.

For continuous discharging centrifuges, such as a Westfalia C6 disc stack centrifuge, the solution is passed through and solids are kept in the bowl. The supernatant stream is continuously discharged. At predetermined set points, the solids in the bowl can be discharged as a slurry into an appropriate collection vessel. Alternatively, water or buffer can be passed over the solids when they are in the bowl to provide a washing step for the solids. The solids can then be discharged at a pre-determined point.

Solubilization of Inclusion Bodies

The washed inclusion body pellet is solubilized in guanidine hydrochloride (4-6 M) containing dithiothreitol (DTT) at 10-50 mM. Solubilization is carried out for 1-2 hours at 15-25° C. The solubilized material is then clarified by centrifugation or used without clarification. HPLC analysis is performed to determine the amount of IL-29 in the soluble fraction. Based on this concentration, the GuHCl/IL-29 solute will be diluted into a refold buffer mixture to a final concentration between 1.25 and 2.0 mg/mL.

A. Solubilization of Washed Inclusion Bodies

The washed inclusion body prep can be solubilized using guanidine hydrochloride (5-8 M) or urea (7-8 M) containing a reducing agent such as beta mercaptoethanol (10-100 mM) or dithiothreitol (5-50 mM). The solutions can be prepared in Tris, phosphate, HEPES or other appropriate buffers. Inclusion bodies can also be solubilized in Tris buffer at pH 10-11.5 with or without urea (1-2 M). Cells from 1 liter of fermentation broth can be solubilized using 50-200 ml of the described solutions. The preferred method is to solubilize the washed inclusion body pellets from 1 liter of fermentation broth in 150 ml of 6 M GuHCl prepared in 100 mM Tris pH 8.0 containing 40 mM DTT. The slurry is re-suspended by mixing with a spatula followed by homogenization with an Omni EZ homogenizer or mixing with a mechanical device. Incubate the mixture for 30-90 minutes with mixing at 4-30° C. to finish the solubilization process. The sample can be centrifuged at 7500-16,000×G at 4° C. for 10-30 minutes using an appropriate centrifuge. The supernatant sample is decanted and retained. Non-clarified samples can also be used for refolding.

B. Solubilization of Washed Inclusion Body Slurries

The washed inclusion body preparation can be produced as slurry of inclusion bodies in water. This is typical after centrifugation and washing using a continuous centrifuge. Solubilizing agents such as guanidine hydrochloride (4-6 M) or urea (4-7 M) can be added in dry powder form to the inclusion body slurries. Buffer (Tris, phosphate, HEPES), salts (magnesium chloride, sodium chloride, potassium chloride) and other compounds such as PEG 3500 can also be added in powder form to the slurried mixture. Reducing agents such as beta mercaptoethanol (10-100 mM) or dithiothreitol (5-50 mM) can be added in powder or liquid form. The slurry is re-suspended by mixing with a high-powered mixer and impeller, an Omni EZ homogenizer, or mixing with a mechanical device. The mixture is incubated for 30-90 minutes with mixing at 4-30° C. to finish the solubilization process. The solubilized inclusion body slurry can is then be centrifuged at 7500-16,000×G at 4° C. for 10-30 minutes using an appropriate centrifuge. The supernatant sample is decanted and retained. Alternatively, the solution is used without clarification.

Refolding

The refolding is performed by slowly adding the solute solution to a refolding mixture of arginine, cystine, cysteine, DTT and salts. The IL-29 solute can be added by batch or fed batch. The recombinant human IL-29 refolding reaction is quenched by adjusting the pH to 5.8 to 6.1, preferably about 5.9. The acidified refold is diluted 4.25-fold in 25 mM sodium acetate, pH 5.6 to precipitate misfolded and unfolded proteins and to condition the refold for loading to the capture column. The precipitate is allowed to settle overnight and then the supernatant is clarified through a depth filter train composed of a coarse (nominal 0.8 μm) and fine (nominal 0.2 μm) filter in series.

The concentration of the IL-29 in the solubilized fraction is determined by reversed phase HPLC. The determination of the refolding buffer volume is based on the amount of solute and the concentration of IL-29 present in the solute. The refolding buffer can contain a variety of salts and polyethylene glycol (0.05-0.5%). Arginine (0.5 to 1.25 M) is used to prevent aggregation. The preferred level of arginine is 1.0 M with an IL-29 concentration of 2.0 mg/ml. An oxido shuffling system is used to initiate disulfide bonding of the IL-29 molecule.

The oxido shuffling system is based on mixtures of reduced and oxidized molecules such as cysteine and cystine, DTT and cystine, reduced glutathione and oxidized glutathione, or DTT and oxidized glutathione. The ratio of reduced to oxidized glutathione or cystine can range between 1:1 to 6:1 with a concentration range between 0.5 and 8 mM. The optimal concentration for refolding IL-29 is about 4 mM cysteine:2 mM cystine.

The solute containing IL-29 is added rapidly (1-30 minutes), or slowly (0.5-5 hours) to the refolding buffer with mixing. The IL-29 can be added in one addition, in multiple additions or fed in over time. The IL-29 is added to the refolding mixture to a final concentration between 0.5 mg/ml and 3.0 mg/ml, preferably 1.5 mg/ml and 2.0 mg/ml. The temperature range is between 4-30° C. The pH is between 7.3 and 8.5. The vessel containing the refold mixture is left open to the atmosphere or can be sparged with air or nitrogen during renaturation. The refolding is allowed to take place for 1-26 hours after the end of the solute addition. Thereafter the refolding reaction is quenched by adjusting the solution pH to 5.5-6.5, and preferably to pH 5.9.

Capture of Refolded IL-29

The clarified, diluted IL-29 is captured on a cation exchange column, e.g., ToyoPearl SP 550C (Tosoh Bioscience), at pH 5.5. The equilibration buffer is 50 mM sodium acetate, pH 5.5, and the bound IL-29 is eluted with an increasing linear gradient to 2 M sodium chloride, in 50 mM sodium acetate, pH 5.5. The capture column eluate pool is adjusted to 1.0 M $(NH_4)_2SO_4$ and then passed through a 0.45 µm filter to remove insoluble material.

This step uses a cation exchange column to capture properly folded IL-29 from a diluted and clarified refold solution. In order for IL-29 to bind to the column a dilution of the refolded solution is first carried out. Currently the refolded IL-29 is diluted 1.5- to 10-fold in water or low ionic strength buffer at pH 5-7. Preferably a 1:4.25 dilution is carried out, using 25 mM sodium acetate, pH 5.6. The conductivity of the solution after dilution should be not more than 30 mS/cm. A precipitate forms and is allowed to settle out of solution for 0.5-18 hr at 10-25° C. The settling preferably occurs for 10-16 hr at 16-22° C. The settled supernatant is then filtered to remove any remaining precipitate in solution. A depth filter train, composed of a 0.8 µm nominal filter in series with a 0.2 µm nominal filter, has been used to remove the precipitate. One can also use a single depth filters or other filter types, such as a bag filter or a graded density filter, or combinations of filters, to clarify the diluted refold supernatant. One can also use centrifugation, either continuous or batch-mode, to remove the precipitate.

Recombinant IL-29 in the refold solution is captured on a cation exchange column at pH 5.5. Typically the column contains ToyoPearl SP 550C resin from Tosoh Bioscience. The column is equilibrated with 50 mM sodium acetate, pH 5.5, and then loaded with clarified, diluted refold to a 1.0-17.5 g IL-29 per liter resin load factor. Preferably the column is loaded with 5-15 g IL-29 per liter resin. After loading, the column is washed with 2-5 CV of equilibration buffer to remove unbound material, and bound IL-29 is then eluted with a linear 0-2M sodium chloride gradient in 50 mM sodium acetate, pH 5.5. IL-29 elutes from SP550C such that the eluate pool is at approximately 0.7-0.8 M sodium chloride.

Many different cation exchange resins for this step, including other sulfopropyl resins such as SP Sepharose XL from GE Healthcare, or weak cation exchangers such as carboxymethyl, can be used as well as different types of solid supports such as agarose or cellulose, and different resin bead particle sizes. One could also run this column at different pH's in the range from 5.0 to 7.0, and with different buffers and salts.

Modified gradient or step elution strategies or formats may be employed to elute recombinant human IL-29 from the column. One can also use expanded bed chromatography to carry out this purification.

Purification of IL-29

The filtered and conditioned solution is loaded to a hydrophobic interaction chromatography ("HIC") column, e.g., ToyoPearl Super Butyl 550C (Tosoh Bioscience), previously equilibrated with 50 mM sodium acetate, 1.5 M $(NH_4)_2SO_4$, pH 5.5. The HIC column is washed with equilibration buffer to remove unbound material and then IL-29 is eluted with a linear gradient to 50 mM sodium acetate, pH 5.5. The HIC eluate pool is diluted 6-fold in water then filtered and applied to a cation exchange column, SP Sepharose HP (GE Healthcare), equilibrated in 50 mM sodium acetate, 300 mM sodium chloride, pH 5.5. The high performance cation exchange column is washed with equilibration buffer and then eluted with a linear gradient to 50 mM sodium acetate, 800 mM sodium chloride, pH 5.5. The eluate pool is then concentrated by ultrafiltration in a tangential flow filtration system equipped with a 5 kDa molecular weight cut-off polyether sulfone membrane. The concentrated product, IL-29 bulk intermediate, is filtered, aliquotted and stored at $\leq -60°$ C.

A. Intermediate Purification of Recombinant Human IL-29

This step is designed to achieve further purification of IL-29, using hydrophobic interaction chromatography (HIC) to remove host cell proteins and IL-29 hydrophobic variants. Typically ToyoPearl Super Butyl 550C resin (Tosoh Bioscience) is used for this step. The resin is equilibrated with 50 mM sodium acetate, 1.5 M $(NH_4)_2SO_4$, pH 5.5. The pool of IL-29 eluted from the capture column is adjusted to 1.0 M $(NH_4)_2SO_4$, via 2-fold dilution with 50 mM sodium acetate, 2.0 M $(NH_4)_2SO_4$, pH 5.5, and then passed through a 0.2 µm or 0.45 µm nominal filter. The adjusted and filtered IL-29 is then loaded onto the equilibrated resin to a load factor between 1.0-20 g IL-29 per liter resin, and preferably to $\leq 18$ g IL-29 per liter resin. The column is washed with equilibration buffer to remove unbound material and then IL-29 is eluted with a linear gradient from 50 mM sodium acetate, 1.0 M $(NH_4)_2SO_4$ to 50 mM sodium acetate with no ammonium sulfate, at pH 5.5. IL-29 elutes from the column from approximately 0.75 M $(NH_4)_2SO_4$ to 0 M $(NH_4)_2SO_4$. All preceding steps are performed at 16-24° C.

One of ordinary skill in the art can use other hydrophobic interaction chromatography resins for this step, including but not limited to other butyl substituted resins, such as ToyoPearl Butyl 650M (Tosoh Bioscience), or those substituted with phenyl, such as ToyoPearl Phenyl 650M (Tosoh Bioscience) or Phenyl Sepharose Fast Flow (GE Healthcare). In addition, different types of solid supports, such as agarose or cellulose, and different resin bead particle sizes, may be used. One can also run this column at different pH's, in the range from 5.0 to 9.0, at different temperatures, and with different buffers and salts (sodium sulfate, for example). Other concentrations of salt in the HIC Load (1.5 M ammonium sulfate, for example) may be used to bind IL-29 to the HIC resin by enhancing the hydrophobic effect, and other gradient or step elution strategies may be employed to elute IL-29 from the column. One can also use displacement chromatography on HIC resins to purify 1'-29, while leaving variants of increased hydrophobicity bound to the column.

B. Polish Purification of Recombinant Human IL-29

This step employs high performance cation exchange chromatography to remove charged variants from the IL-29 solution. The term "high-performance" refers to the ability to better resolve different charged components from one another due in large part to a reduced resin bead size. In the process described here, the high performance cation exchange resin bead is approximately 9-fold smaller than the cation exchange resin bead used for the lower resolution capture (SP550C) step. For this purification step, SP Sepharose HP resin (GE Healthcare) is used. The resin is equilibrated with 50 mM sodium acetate, 300 mM sodium chloride, pH 5.5. The pool from the HIC column is diluted 6-fold in water or low ionic strength buffer, then 0.2 µm filtered in preparation for loading to the column. The adjusted and filtered IL-29 solution is then loaded onto the equilibrated resin to a load factor between 1.0-50 g IL-29 per liter resin, and preferably to between 15-30 g IL-29 per liter resin. The column is washed with equilibration buffer to remove unbound material and then IL-29 is eluted with a linear gradient to 50 mM sodium acetate, 800 mM sodium chloride, pH 5.5. IL-29 elutes from the column from approximately 0.4 M to 0.6 M sodium chloride.

One can use any of many different cation exchange resins for this step, including other sulfopropyl resins, or weak cation exchangers such as carboxymethyl, as well as different types of solid supports such as agarose or cellulose, and different resin bead particle sizes. One can also run this column at different pH's in the range from 5.0 to 7.0, and with different buffers and salts. The addition of organic modifiers (such as 10% isopropanol or 10% ethanol) to the equilibration and elution buffers may be used to alter column resolution and selectivity. Modified gradient or step elution strategies may be employed to elute IL-29 from the column.

C. Concentration of IL-29

This step is designed to concentrate the SP HP column eluate, generating IL-29 bulk intermediate. The SPHP pool is concentrated approximately 2-4 fold using a 5-kDa molecular weight cut-off polyether sulfone tangential flow filtration (TFF) plate and frame membrane at a transmembrane pressure of 15-25 psi. After the concentrated retentate is removed from the TFF system, the system is rinsed with buffer (such as 50 mM sodium acetate, pH 5.5), and the rinse is combined with the concentrated retentate. This solution is then filtered through a 0.2 µm membrane, then filled in appropriate containers and stored in preparation for the subsequent PEGylation reaction. One can use membranes of different composition, such as those constructed of regenerated cellulose, and/or of different porosity, such as a 3 kDa molecular weight cut-off plate and frame membrane or a 10 kDa molecular weight cut-off hollow fiber system, to accomplish this ultrafiltration step. Alternatively this concentration step may be skipped, if the SPHP pool is of sufficient IL-29 concentration to execute the PEGylation reaction described below.

D. Properties of Purified Recombinant Human IL-29 Bulk Intermediate

The purity of IL-29 bulk intermediate is at least 95%, at least 96%, at least 97%, at least 98%, or at least 99% by sodium dodecyl sulfate polyacrylamide gel analysis. Aggregates are less than 1.0%, less than 0.9%, less than 0.8%, less than 0.7%, less than 0.6%, less than 0.5%, less than 0.4, less than 0.3%, less than 0.2%, less than 0.1%, or less than 0.005% by size exclusion HPLC. Charge heterogeneity by cation exchange HPLC is about 10%, 9%, 8%, 7%, 6%, 5%, 4%, 3%, 2% or 1% and the purity measured by reversed phase HPLC is at least 90%, 91%, 92%, 93%, 94%, 95%, 96%, 97%, 98%, or 99%.

The potency of IL-29 (same assays for PEG-IL-29) was measured using a cell-based activity assay. The bioassay utilizes a 293 human embryonic kidney (293 HEK) reporter cell line that was engineered to over-express the human IL-29 receptor, and contains a firefly luciferase reporter construct (KZ157), which includes ISRE and STAT binding elements placed directly upstream of the luciferase gene. The IL-29 receptor is a heterodimer consisting of IL-10 receptor β (IL-10Rβ) and IL-28 receptor alpha (IL-28Rα) subunits. Overexpression of the IL-29 receptor was achieved by stable transfection of 293 HEK cells with the IL-28Rα cDNA, which along with endogenously expressed IL-10Rβ form the heterodimeric IL-29 receptor. Binding of IL-29 (or PEG-IL-29) to the IL-29 receptor activates the JAK/STAT signaling pathway and results in the formation of the intracellular transcription factor, ISGF3. Subsequent binding of ISGF3 to ISRE/STAT DNA sequence elements resulted in expression of the firefly luciferase gene product. Recombinant human IL-29 was active in the IL-29 cell-based potency bioassay.

In the bioassay, the assay cells were stimulated with IL-29 (or PEG-IL-29) for 4 hours and then lysed. After addition of a luciferase substrate luciferin to the lysed cells, luciferase expression was measured indirectly in relative light units (RLU) using a luminometer. A calibration curve was generated using a IL-29 (or PEG-IL-29) reference standard, relating the luminescence signal to the concentration of the IL-29 reference standard, from which the potency of control and test samples was calculated. Results were reported as relative potency units per milligram (RPU/mg) calculated relative to the reference standard. A development reference lot for IL-29 and PEG-IL-29 were assigned relative potency units of one per milligram of protein (1 RPU/mg).

PEGylation OF IL-29

IL-29 polypeptides, fusion, fragments, mutants, and variants of the present invention can be modified with polyethylene glycol ("PEG"), a process known as "PEGylation." PEGylation of an IL-29 polypeptide can be carried out by any of the PEGylation reactions known in the art (see, for example, EP 0 154 316, Delgado et al., *Critical Reviews in Therapeutic Drug Carrier Systems,* 9:249 (1992), Duncan and Spreafico, *Clin. Pharmacokinet.* 27:290 (1994), and Francis et al., *Int J Hematol* 68:1 (1998)). For instance, PEGylation can be performed by an acylation reaction or by an alkylation reaction with a reactive polyethylene glycol molecule. In an alternative approach, IL-29 polypeptide conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with an IL-29 polypeptide. An example of an activated PEG ester is PEG esterified to N-hydroxysuccinimide. As used herein, the term "acylation" includes the following types of linkages between IL-29 polypeptide and a water-soluble polymer: amide, carbamate, urethane, and the like. Methods for preparing PEGylated IL-29 by acylation will typically comprise the steps of (a) reacting an IL-29 polypeptide with PEG (such as a reactive ester of an aldehyde derivative of PEG) under conditions whereby one or more PEG groups attach to IL-29, and (b) obtaining the reaction product(s). Generally, the optimal reaction conditions for acylation reactions will be determined based upon known parameters and desired results. For example, the larger the ratio of PEG:IL-29, the greater the percentage of polyPEGylated IL-29 product.

PEGylation by alkylation generally involves reacting a terminal aldehyde, e.g., propionaldehyde, butyraldehyde, acetaldehyde, and the like, derivative of PEG with IL-29 polypeptide in the presence of a reducing agent. PEG groups are preferably attached to the polypeptide via a —CH2-NH2 group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups.

Reductive alkylation to produce a substantially homogenous population of monopegylated IL-29 conjugate molecule can comprise the steps of: (a) reacting an IL-28 or IL-29 polypeptide with a reactive PEG under reductive alkylation conditions at a pH suitable to permit selective modification of the α-amino group at the amino terminus of the IL-29 polypeptide, and (b) obtaining the reaction product(s). The reducing agent used for reductive alkylation should be stable in aqueous solution and preferably be able to reduce only the Schiff base formed in the initial process of reductive alkylation. Preferred reducing agents include sodium borohydride, sodium cyanoborohydride, dimethylamine borane, trimethylamine borane, and pyridine borane.

For a substantially homogenous population of monopegylated IL-29 conjugates, the reductive alkylation reaction conditions are those that permit the selective attachment of the water-soluble polymer moiety to the N-terminus of IL-29 polypeptide. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer: L-29 need not be as large because more reactive groups are available. Typically, the pH will fall within the range of 3-9, or 3-6. Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 40 kDa. The molar ratio of water-soluble polymer to IL-29 will generally be in the range of 1:1 to 100:1. Typically, the molar ratio of water-soluble polymer to IL-29 will be 1:1 to 20:1 for polyPEGylation, and 1:1 to 5:1 for monoPEGylation.

In preparation for a PEGylation reaction, the recombinant IL-29 bulk intermediate is thawed and transferred to a reaction vessel. Buffer for dilution, sodium cyanoborohydride reductant stock solution, and derivatized polyethylene glycol ("PEG") (e.g., 20 kDa linear methoxyPEG-propionaldehyde) stock solution, are added to the reaction to create a mixture with 5 g/L IL-29, 10 g/L derivatized PEG, and 20 mM sodium cyanoborohydride at pH 5.5 in 50 mM sodium acetate buffer. The reaction is allowed to proceed with mixing for ~18 hr at 16-20° C.

This step is used to covalently attach polyethylene glycol (PEG) molecules to IL-29, and preferentially a single PEG at the protein's amino-terminus. A PEG stock solution, composed of, for example, 20 kDa linear methoxyPEG-propionaldehyde (from, for example, Nippon Oil & Fat), at 20-200 mg/ml concentration in 50 mM sodium acetate, pH 4.5-6.5, and preferably at 100 mg/ml concentration, pH 5.5, is prepared. A reductant stock solution, comprised of 5-500 mM sodium cyanoborohydride (preferably 100-200 mM) in 50 mM sodium acetate buffer, with pH in the range of 4.5-6.5 (preferably pH 5.5), is also prepared. The IL-29 bulk intermediate solution is transferred to a reaction vessel of appropriate size. Buffer (such as 50 mM sodium acetate, pH 5.5), reductant stock solution, and PEG stock solution are added sequentially in that order such that the final mixture contains a 2-6 g/L IL-29 concentration, a 1-to-4-fold molar excess of PEG over IL-29, and a 5-40 mM concentration of sodium cyanoborohydride, at a pH ranging from 4.5-6.5. The reaction solution is then mixed for 2-24 hr at 16-24° C. In a preferred case, the final reaction mixture contains IL-29 at 3-5 g/L concentration, with a 2-fold molar excess of PEG relative to the IL-29 polypeptide concentration, and with 10-20 mM sodium cyanoborohydride, at pH 5.5. This reaction is allowed to mix for 14-18 hr at 16-20° C.

One skilled in the art would know to use other PEG molecules, of longer or shorter chain length, to PEGylate the protein. For example, a 30 kDa linear methoxyPEG-propionaldehyde to PEGylate IL-29 under the conditions described above has also been used. One can use branched chain, rather than linear, PEG molecules in the reaction. The activated PEG may also be derivatized using other aldehydes, such as butyraldehyde, or may be derivatized with other amine-reactive compounds. Other site-specific PEG chemistries could be used to target other specific sites on IL-29 for derivatization. For the reactive aldehydes example, other reducing agents that would selectively reduce an imine to the amine may be substituted for the sodium cyanoborohydride. Other reaction conditions, varying temperature, pH, salt composition and concentration, may also be tried to enhance yields of the desired N-terminally monoPEGylated species.

Purification of PEG-IL-29

Afterwards the pegylating IL-29, the reaction is diluted 2-fold with 50 mM sodium acetate, pH 5.5 then 0.2 μm filtered and loaded to a second cation exchange column (e.g, SP Sepharose HP (GE Healthcare)), equilibrated in 50 mM sodium acetate, 200 mM sodium chloride, pH 5.5. The high performance cation exchange column is washed with equilibration buffer and then eluted with a linear gradient to 50 mM sodium acetate, 500 mM sodium chloride, pH 5.5. The eluate pool containing monoPEGylated IL-29 is then concentrated by ultrafiltration in a tangential flow filtration system equipped with a 5 kDa molecular weight cut-off polyether sulfone membrane. After concentration, the retentate is diafiltered against 7 diavolumes of formulation buffer to generate monopegylated IL-29 ("PEG-IL-29") bulk drug substance. The formulated bulk drug substance is then 0.2 μm filtered, filled, and stored at ≤−60° C. for future use.

A. High Performance Cation Exchange Purification of PEG-IL-29

This step employs high performance cation exchange chromatography to separate multi-PEGylated (containing two or more PEG groups per protein) and unPEGylated IL-29 proteins from the desired monoPEGylated species. Here, SP Sepharose HP resin (GE Healthcare) is used. The resin is equilibrated with 50 mM sodium acetate, 200 mM sodium chloride, pH 5.5. The reaction mixture is diluted 2-fold in water or low ionic strength buffer (preferably 50 mM sodium acetate, pH 5.5), then 0.2 μm filtered in preparation for loading to the column. The adjusted and filtered solution is then loaded onto the equilibrated resin, which is then washed with equilibration buffer to remove unbound material. PEGylated IL-29 proteins are eluted with a linear gradient to 50 mM sodium acetate, 500 mM sodium chloride, pH 5.5. MonoPEGylated IL-29 elutes from the column from approximately 0.3 M to 0.5 M sodium chloride. A step to 50 mM sodium acetate, 1 M sodium chloride, pH 5.5, is then used to elute unPEGylated IL-29 from the column.

One of skill in the art would know how to use any of many different cation exchange resins for this step, including other sulfopropyl resins, or weak cation exchangers such as carboxymethyl, as well as different types of solid supports such as agarose or cellulose, and different resin bead particle sizes. A skilled artisan would also know to run this column at different pH's in the range from 5.0 to 7.0, and with different buffers and salts. Modified gradient or step elution strategies may be employed to elute PEGylated IL-29 from the column.

B. Concentration and Diafiltration of PEG-IL-29

This step is designed to concentrate the SP HP column eluate containing PEG-IL-29, and exchanging the solution into formulation buffer, generating PEG-IL-29 bulk drug substance. The SPHP pool is concentrated approximately 10-15 fold using a 5 kDa molecular weight cut-off polyether sulfone tangential flow filtration (TFF) plate and frame membrane. After concentration, the solution is diafiltered for 5-10 diavolumes against formulation buffer. Both concentration and buffer exchange occur at transmembrane pressures in the range of 15-25 psi. The buffer exchanged concentrate is then removed from the TFF system, the system is rinsed with buffer, and the rinse is combined with the concentrated retentate. This solution is then filtered through a 0.2 μm membrane, then filled in appropriate containers and stored as bulk drug substance.

One can also use membranes of different composition, such as those constructed of regenerated cellulose, and/or of different porosity, such as a 3 kDa molecular weight cut-off plate and frame membrane or a 10 kDa molecular weight cut-off hollow fiber system, to accomplish this ultrafiltration/diafiltration step.

Additional Purification of IL-29 and PEG-IL-29

It may be necessary to further purify either IL-29 or PEG-IL-29 to remove remaining impurities and contaminants. An anion exchange column may be used to reduce the endotoxin level. IL-29 is diluted to a conductivity level of <10 mS/cm and the pH is adjusted to 8.0. It is applied to a Q Sepharose FF column that has been equilibrated to 20 mM Tris, pH 8.0. The IL-29 should pass through the column and have an approximately 80% reduction in endotoxin compared to the load. IL-29 polypeptide or PEG-IL29 polypeptide will have an endotoxin level of less than 10 endotoxin units per milligram of IL-29 polypeptide or PEG-IL29 polypeptide in a Limulus amoebocyte lysate assay based on USP <85> (See, for example, R. Nachum and R. N. Berzofsky, *J. Clinical Microbiology*, 21(5):759-763 (May 1985)). Mustang Q or Mustang E charged membranes (Pall) may also be used to reduce endotoxin levels in solutions between pH 5.0 and 9.0.

Other purification steps that can be used to further purify IL-29 include immobilized metal affinity chromatography, anion exchange chromatography, or hydrophobic charge induction chromatography. One may be able to use displacement chromatography to purify IL-29 or PEG-IL-29, whereby high protein loading of the column causes the protein of interest to elute due to being displaced by more tightly binding impurities. Alternatively, it may be possible to utilize a flow-through mode of chromatography whereby impurities bind to the resin, while IL-29 or PEG-IL-29 pass through during the load step (as in the endotoxin removal example on Q Sepharose, above).

Properties of Purified PEG-IL-29

The purity of PEG-IL-29 bulk drug substance is at least 95%, at least 96%, at least 97%, at least 98%, at least 99%, or greater than 99% by sodium dodecyl sulfate polyacrylamide gel analysis. Aggregates are less than 1.0%, less than 0.9%, less than 0.8%, less than 0.7%, less than 0.6%, less than 0.5%, less than 0.4, less than 0.3%, less than 0.2%, less than 0.1%, or less than 0.005% by size exclusion HPLC. Charge heterogeneity by cation exchange HPLC is about 10%, 9%, 8%, 7%, 6%, 5%, 4%, 3%, 2% or 1% and the monoPEG purity measured by reversed phase HPLC is at least 95%, at least 96%, at least 97%, at least 98%, at least 99%, or greater than 99%. The potency of PEG-IL-29 was measured using a cell-based activity assay as described above. PEG-IL-29 was active in the IL-29 cell-based potency bioassay.

The invention is further illustrated by the following non-limiting examples.

EXAMPLES

Example 1

Construction of Expression Vector, pTAP395

The backbone used to construct the *E. coli* expression vector for IL-29 C172S d2-7 (SEQ ID NO:5) was pTAP395. pTAP395 contained the srp promoter, two transcriptional terminators, rrnB T1 and rrnB T2, kanamycin resistance gene, origin of replication, URA3 selection marker and the ARS-CENS6 locus for plasmid replication in yeast. pTAP395 was generated from pTAP238 but has a different translational enhancer from pTAP238. pTAP395 had the translational enhancer known as chan2 or zymo2 (SEQ ID NO:13). pTAP395 was constructed using oligos zc42188 (SEQ ID NO:14), zc42187 (SEQ ID NO:15), zc42194 (SEQ ID NO:16), and zc29741 (SEQ ID NO:17) by implementing an overlap-PCR strategy. The ends of the PCR fragment were homologous to pTAP395. The central region between the XbaI and SmaI sites contained the zymo2 ((SEQ ID NO:13)) translational enhancer. The PCR reagent concentrations were as follows: 1 μM of zc42188 (SEQ ID NO:14) and zc29741 (SEQ ID NO:17); 50 nM of zc42187 (SEQ ID NO:15) and zc42194 (SEQ ID NO:16); 0.2 mM dNTPs; 1× reaction buffer; and 0.05 U/4, Pwo (Roche). The reaction consisted of 10 cycles of the following: 94° C. for 30 seconds, 55° C. for 30 seconds, and 72° C. for 30 seconds. Four reactions were done in all. The DNA was precipitated using two volumes of 100% ethanol and centrifuging in a micro-centrifuge. The supernatant was discarded, and the pellet was resuspended in 10 μL of water. The resulting DNA fragment was checked for size by electrophoresis of 2 μL on a 2% 1×TBE agarose gel. The size of the PCR fragment was approximately 150 bp, as expected. The remaining DNA was mixed with 100 ng of pTAP238 digested with SmaI. The DNA mixture was then mixed with 100 μL of electrocompetent SF838-9Dα yeast cells (*S. cerevisiae*) and electroporated under the following conditions: 25 μF, 0.75 kV, and ∞ ohms. Six hundred microliters of 1.2 M sorbitol were added to the cells, which were then spread on −Ura D plates and incubated at 30° C. for approximately 72 hours. The Ura+ yeast transformants from a single plate were suspended in 2-3 mL H$_2$O and centrifuged briefly to pellet the cells. The cell pellet was resuspended in 1 mL of lysis buffer (2% Triton X-100, 1% SDS, 100 mM NaCl, 10 mM Tris, pH 8.0, 1 mM EDTA). Five hundred microliters of the lysis mixture were added to an Eppendorf tube containing 300 μL acid washed glass beads and 500 μL phenol-chloroform. The sample was vortexed for 1-minute intervals two or three times and then centrifuged for 5 minutes in an Eppendorf centrifuge at maximum speed. Three hundred microliters of the aqueous phase were transferred to a fresh tube. The DNA was precipitated with 600 μL 100% ethanol and centrifuged for 10 minutes at 4° C. The DNA pellet was resuspended in 100 µL H₂O. Forty microliters of electrocompetent MC1061 cells were transformed with 1 µL of the plasmid DNA prep. The cells were pulsed at 2.0 kV, 25 µF and 400 ohms. Following electroporation, 600 µL SOC were added to the cells which were allowed to recover at 37° C. for one hour. The cells were then plated as one aliquot onto LB plates (LB broth (Lennox), 1.8% Bacto™ Agar (Difco)) containing 25 µg/mL kanamycin and grown overnight at 37° C. Screening via colony PCR using primers, zc42188 (SEQ ID NO:14) and zc29741 (SEQ ID NO:17), identified cells harboring the correct construct containing the DNA sequence for the altered translational enhancer. The PCR conditions were as follows: 0.2 µM of each oligo; 0.2 mM dNTPs; 1× reaction buffer; and 0.05 U/µL Taq (Roche). The template for each reaction was a single colony picked from the transformation plate and suspended in 10 µL of LB. The PCR consisted of 25 cycles of the following: 94° C. for 30 seconds, 55° C. for 30 seconds, and 72° C. for 1 minute. All eight clones were positive as judged by analysis on a 2% agarose gel, and three were subjected to sequence analysis. The correct clone became known as pTAP395.

Example 2

Construction of Codon Optimized IL-29 Gene

The IL-29 coding sequence with codon optimized for translation in *E. coli* was constructed from ten overlapping oligonucleotides (Oligo number: zc44,559 (SEQ ID NO:18), zc44,566 (SEQ ID NO:19), zc44,565 (SEQ ID NO:20), zc44, 562 (SEQ ID NO:21), zc44,563 (SEQ ID NO:22), zc44,560 (SEQ ID NO:23), zc44,561 (SEQ ID NO:24), zc44,564 (SEQ ID NO:25), zc44,557 (SEQ ID NO:26) and zc44,558 (SEQ ID NO:27). Primer extension followed by PCR amplification produced a full-length, optimized IL-29 gene. The final PCR product was inserted into the cloning vector, pCR-Blunt II TOPO by ligation. The ligation mix was transformed into competent *E. coli* TOP10. Kanamycin resistant clones were screened by colony PCR. A positive clone was verified by DNA sequencing.

Example 3

Construction of Expression Vector pCHAN15

The strategy used to generate the IL-29 C172S (SEQ ID NO: 1) mutant is based on the QuikChange® Site-Directed Mutagenesis Kit (Stratagene, La Jolla, Calif.). Primers were designed to introduce the C172S mutation according to the manufacturer's suggestions. The primers were designated zc44,340 (SEQ ID NO:28) and zc44,341 (SEQ ID NO:29). PCR was performed to generate the IL-29 C172S mutant according to instructions provided with the QuikChange Mutagenesis Kit. Five identical 50 µL reactions were set-up. Each reaction contained 2.5 µL of pSDH175 (expression construct with the optimized IL-29 gene sequence) as template. The PCR cocktail contained the reagents: 30 µL 10×PCR buffer, 125 ng (27.42 µL) zc44,340 (SEQ ID NO:28). 125 ng (9.18 µL) zc44,341 (SEQ ID NO:29), 6 µL dNTP, 6 µL Pfu Turbo polymerase (Strategene), and 206.4 µL water. Each reaction received 47.5 µL of the cocktail. The PCR conditions were as follows: 1 cycle of 95° C. for 30 seconds followed by 16 cycles of 95° C. for 30 seconds, 55° C. for 1 minute, 68° C. for 7 minutes, and 1 cycle at 68° C. for 7 minutes. After the last cycle, the reaction was held at 4° C. All five PCR reactions were consolidated into one tube. As per manufacturer's instructions, 5 µL of the restriction enzyme DpnI was added to the PCR reaction and the mixture was incubated at 37° C. for 2 hours. DNA was precipitated by adding 10% 3M sodium acetate and two volumes of 100% ethanol. The DNA pellet was resuspended in 20 µL water and transformed into *E. coli* strain DH10B. Electroporated cells were then allow to recover at 37° C. for 1 hour. The cells were plated on an LB agar containing 25 µg/mL kanamycin and incubated at 37° C. overnight. Ten clones were screened for the presence of an insert containing IL-29 C172S. DNA was isolated from all ten clones using the QIAprep™ Spin Miniprep Kit (Qiagen) and analyzed for presence of insert by digestion with XbaI (Roche) and PstI (New England Biolabs). Nine clones contained the insert and were sequenced to insure that the IL-29 C172S mutation had been introduced. One clone for which the sequence was verified was saved and labeled pSDH188. Subsequently, the IL-29 C172S insert was sub-cloned into the expression vector, pTAP395. The resulting construct became known as pCHAN15.

Example 4

Construction of Expression Vector, pTAP440

The oligos used for the construction of pTAP440 were zc49249 (forward primer) (SEQ ID NO:30) and zc45403 (reverse primer) (SEQ ID NO:31). The first 38 bases on the 5' end of zc49249 are homologous to the vector backbone, pTAP395. The remaining 26 bases contained the initial methionine codon (ATG) followed by DNA sequence homologous to the IL-29 gene, starting at the eighth codon. The 5' end of the reverse primer, zc45403 (SEQ ID NO:31), consists of 39 bases homologous to the vector backbone. The second half, 25 bases, of the oligo are homologous to the optimized IL-29 gene which contained the base pair changes coding for the C172S mutation. To amplify the gent for IL-29 the following final concentrations of reagents were used in a total reaction volume of 100 µL: 0.2 µM of each oligo; 0.2 mM dNTPs; 1× reaction buffer; 10% DMSO; and 0.05 U/µl Pwo (Roche). The template used for amplification was pCHAN15. The reaction consisted of 25 cycles of the following: 94° C. for 30 seconds, 55° C. for 30 seconds, and 72° C. for 1 minute. The DNA was precipitated using two volumes of 100% ethanol and pelleted in a micro-centrifuge. The supernatant was discarded, and the pellet was resuspended in 10 µL of water. The resulting DNA fragment was checked for size by electrophoresis of 2 µL on a 1% 1×TBE agarose gel. The size of the PCR fragment was approximately 500 bp, as expected. Eight microliters of the DNA were mixed with 2 µL of pTAP395 digested with SmaI.

The DNA mixture was mixed with 100 µL of electrocompetent SF838-9Dα yeast cells (*S. cerevisiae*) and electroporation was performed under the following conditions: 25 µF, 0.75 kV, and ∞ ohms. Six hundred microliters of 1.2 M sorbitol were added to the cells. The cells were spread on –Ura D plates and incubated at 30° C. for approximately 72 hours. The Ura+ transformants from a single plate were resuspended in 2-3 mL H₂O and centrifuged briefly to pellet the cells. The cell pellet was resuspended in 1 mL of lysis buffer (2% Triton X-100, 1% SDS, 100 mM NaCl, 10 mM Tris, pH 8.0, 1 mM EDTA). Five hundred microliters of the lysis mixture were added to an Eppendorf tube containing 300 µL acid washed glass beads and 500 µL phenol-chloroform. The sample was vortexed for 1-minute intervals two or three times and centrifuged for 5 minutes in an Eppendorf centrifuge at maximum speed. Three hundred microliters of the aqueous phase were transferred to a fresh tube. The DNA was precipitated with 600 µL of 100% ethanol and centrifuged for 10 minutes at 4° C. The DNA pellet was resuspended in 50 µL H$_2$O.

Transformation of electrocompetent *E. coli* cells was performed using 1 µl of the plasmid DNA prep and 40 µL of MC1061 cells. The cells were pulsed at 2.0 kV, 25 µF and 400 ohms. Following electroporation, 600 µL of Terrific Broth were added to the cells which were allowed to recover at 37° C. for one hour. The cells were plated on LB agar containing 25 µg/mL kanamycin and grown overnight at 37° C. Screening via colony PCR using primers, zc49249 (SEQ ID NO:30) and zc45403 (SEQ ID NO:31), identified the cells harboring the correct expression construct which contained the DNA sequence for IL-29 C172S d2-7 (SEQ ID NO:5). The PCR conditions were as follows: 0.2 µM of each oligo; 0.2 mM dNTPs; 1× reaction buffer; 10% DMSO; and 0.05 U/µL Pwo (Roche).

The template for each reaction was a single colony picked from the transformation plate and suspended in 10 µL of LB. The PCR consisted of 25 cycles of the following: 94° C. for 30 seconds, 55° C. for 30 seconds, and 72° C. for 1 minute. All eight clones tested were positive by analysis on a 1% agarose gel, and four were subjected to sequence analysis. One of the clones, now known as pTAP440, was selected from the four submitted to sequencing. Ten microliters of DNA were digested in a reaction that contained 2 µL of Not1, 3 µL of NEB buffer 3, and 15 µL of water for one hour at 37° C. Then 7 µL of this reaction were mixed with 2 µL of 5× buffer and 1 µL of T4 DNA ligase. This reaction incubated at room temperature for one hour. One microliter of the ligation reaction was used to transform strain W3110 [F⁻ IN(rrnD⁻ rrnE)1 lambda⁻] (obtained, for instance, from ATCC) by electroporation.

The cells were pulsed at 2.0 kV, 25 µF and 400 ohms. Following electroporation, 600 µL SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) were added to the cells. The cells grew at 37° C. for one hour and were plated in one aliquot on an LB agar containing 25 µg/mL kanamycin. The plate was incubated at room temperature for 48 hours. Four colonies were picked and grown overnight in LB containing 25 µg/mL kanamycin at 37° C. Plasmid DNA was isolated using a QIAprep Spin Miniprep Kit (Qiagen). The DNA was digested with PvuII to confirm the loss of yeast URA3 and CEN/ARS elements: 12.5 µL DNA, 1 µL PvuII, 1.5 µL buffer 2 NEB at 37° C. for one hour. One of the correct clones lacking the yeast elements was used to transform 40 µL electrocompetent ZGOLD5 [F⁻ IN(rrnD-rrnE)1 lambda⁻ ΔompT::tet ΔfhuA::Cm]. The cells were pulsed at 2.0 kV, 25 µF and 400 ohms. Following the electroporation, 600 µL SOC were added to the cells. The cells were grown at 37° C. for one hour and then plated on LB agar containing 25 µg/mL kanamycin. The plates were incubated at 37° C. for 24 hours. Since the bacteria were transformed with pure plasmid, it was assumed that kanamycin resistant bacteria harbored the plasmid. ZGOLD5 transformed with pTAP440 was preserved and stored frozen.

Example 5

Glucose Fed Batch Fermentation

ECD686 (IL-29: C172S)

A shake flask (baffled 500 ml flask with 100 ml medium) was prepared with ZSM medium. Growth was started by inoculating the shake flask with a 0.10 mL of *E. coli* W3110 containing the expression vector pSDH177 (EE675) from a vial of a research working cell bank. This vector codes for the C172S form of the IL-29 molecule. Growth in the shake flask was at a temperature of 32° C. with the agitation set at 250 rpm. The culture was grown overnight (16 hours) until the OD$_{600}$ was between 8 and 20 units.

A 6 L fermentation vessel was prepared with 3.0 L of PCOL-01 medium and sterilized. After sterilization the medium was supplemented with glucose at 20 g/L, 1 M MgSO4 (10 ml/L) and kanamycin at 25 ug/ml. The pH of the medium was adjusted to a pH of 6.8. The vessel aeration was set to 1 vvm and agitation at 350 rpm, temperature was set to 37° C. The fermentor was inoculated from a shake flask culture that had been grown for 16 hours and had an OD of 10.9 at 600 nm. The inoculation level was 5% volume/volume. The dissolved oxygen level was maintained above 30% saturation by increasing agitation speed.

A carbohydrate solution was fed into the fermentor starting at 9 hours EFT. The feed was continued until the end of the fermentation. The feed solution was glucose prepared at 50% w/w. The feed rate was 10.8 grams of glucose per liter per hour based on the initial starting volume. At 24 hours EFT, IPTG was added to the culture to a concentration of 1 mM. At 48 hours EFT, the fermentation was harvested. The biomass reached 58.8 g dry cell weight (DCW)/L at harvest with a fermentation titer of 4.6 g IL-29/L fermentor broth.

Example 6

Glucose Fed Batch Fermentation

ECD712 (IL-29 C172S)

A shake flask (baffled 500 ml flask with 100 ml medium) was prepared with ZSM medium. Growth was started by inoculating the shake flask with a 0.10 mL of *E. coli* ZGOLD1 [F− IN(rrnD-rrnE)1 lambda⁻ ΔompT::tet] containing the expression vector pCHAN15 (EE733) from a vial of a research working cell bank. This vector codes for the C172S form of the IL-29 molecule. Growth in the shake flask was at a temperature of 32° C. with the agitation set at 250 rpm. The culture was grown overnight (16 hours) until the OD$_{600}$ was between 8 and 20 units.

A 6 L fermentation vessel was prepared with 3.0 L of PCOL-01 medium and sterilized. After sterilization the medium was supplemented with glucose at 20 g/L, 1 M MgSO4 (10 ml/L) and kanamycin at 25 ug/ml. The pH of the medium was adjusted to a pH of 6.8. The vessel aeration was set to 1 vvm and agitation at 350 rpm, temperature was set to 37° C. The fermentor was inoculated from a shake flask culture that has been grown for 16 hours and had an OD of 13.1 at 600 nm. The inoculation level was 5% v/v. The dissolved oxygen level was maintained above 30% saturation by increasing agitation speed.

A carbohydrate solution was fed into the fermentor starting at 9.5 hours EFT. The feed was continued until the end of the fermentation. The feed solution was glucose prepared at 50% w/w %. The feed rate was 9.5 grams of glucose per liter per hour based on the initial starting volume. At 24 hours EFT, IPTG was added to the culture to a concentration of 1 mM. At 48 hours EFT, the fermentation was harvested. The biomass reached 67.4 g dry cell weight (DCW)/L at harvest with a fermentation titer of 3.6 g IL-29/L fermentor broth.

Example 7

Glucose Fed Batch Fermentation

ECD856 (IL-29: C172S+Leucine)

A shake flask (baffled 500 ml flask with 100 ml medium) was prepared with ZSM medium. Growth was started by inoculating the shake flask with a 0.10 mL of *E. coli* ZGOLD1 containing the expression vector pTAP438 (EE831) from a vial of a research working cell bank. This vector codes for a C172S form of the IL-29 molecule that contains an added leucine after the N-terminal methionine. Growth in the shake flask was at a temperature of 32° C. with the agitation set at 250 rpm. The culture was grown overnight (16 hours) until the $OD_{600}$ was between 8 and 20 units.

A 6 L fermentation vessel was prepared with 3.0 L of PCOL-13 medium and sterilized. After sterilization the medium was supplemented with glucose at 20 g/L, 1 M MgSO4 (10 ml/L) and kanamycin at 25 ug/ml. The pH of the medium was adjusted to a pH of 6.8. The vessel aeration was set to 1 vvm and agitation at 350 rpm, temperature was set to 37° C. The fermentor was inoculated from a shake flask culture that has been grown for 16 hours and had an OD of 13.8 at 600 nm. The inoculation level was 5% volume/volume. The dissolved oxygen level was maintained above 30% saturation by increasing agitation speed.

A carbohydrate solution was fed into the fermentor starting at 8 hours EFT. The feed was continued until the end of the fermentation. The feed solution was glucose prepared at 50% w/w %. The feed rate was 9.5 grams of glucose per liter per hour based on the initial starting volume. At 24 hours EFT, IPTG was added to the culture to a concentration of 1 mM. At 50 hours EFT, the fermentation was harvested. The biomass reached 70.0 g DCW/L at harvest with a fermentation titer of 7.3 g IL-29/L fermentor broth.

Example 8

Glucose Fed Batch Fermentation

ECD859 (IL-29 C172S d2-7)

A shake flask (baffled 500 ml flask with 100 ml medium) was prepared with ZSM medium. Growth was started by inoculating the shake flask with a 0.10 mL of *E. coli* ZGOLD1 containing the expression vector pTAP440 (EE833) from a vial of a research working cell bank. This vector codes for a form of the IL-29 molecule that contains a deletion of the second through seventh amino acids. Growth in the shake flask was at a temperature of 32° C. with the agitation set at 250 rpm. The culture was grown overnight (16 hours) until the $OD_{600}$ was between 8 and 20 units.

A 6 L fermentation vessel was prepared with 3.0 L of PCOL-13 medium and sterilized. After sterilization the medium was supplemented with glucose at 20 g/L, 1 M MgSO4 (10 ml/L) and kanamycin at 25 ug/ml. The pH of the medium was adjusted to a pH of 6.8. The vessel aeration was set to 1 vvm and agitation at 350 rpm, temperature was set to 37° C. The fermentor was inoculated from a shake flask culture that has been grown for 16 hours and had an OD of 12.5 at 600 nm. The inoculation level was 5% v/v. The dissolved oxygen level was maintained above 30% saturation by increasing agitation speed.

A carbohydrate solution was fed into the fermentor starting at 8 hours EFT. The feed was continued until the end of the fermentation. The feed solution was glucose prepared at 50% w/w. The feed rate was 9.5 grams of glucose per liter per hour based on the initial starting volume. At 24 hours EFT, IPTG was added to the culture to a concentration of 1 mM. At 50 hours EFT, the fermentation was harvested. The biomass reached 82.8 g dry cell weight (DCW)/L at harvest with a fermentation titer of 11.3 g IL-29/L fermentor broth.

Example 9

Glucose Fed Batch Fermentation+Soy Peptone

ECD892 (IL-29 C172S d2-7)

A shake flask (baffled 500 ml flask with 100 ml medium) was prepared with ZSM medium. Growth was started by inoculating the shake flask with a 0.10 mL of *E. coli* W3110 containing the expression vector pTAP440 (EE826) from a vial of a research working cell bank. This vector codes for a form of the IL-29 molecule that contains a deletion of the second through seventh amino acids. Growth in the shake flask was at a temperature of 32° C. with the agitation set at 250 rpm. The culture was grown overnight (16 hours) until the $OD_{600}$ was between 8 and 20 units.

A 6 L fermentation vessel was prepared with 3.0 L of PCOL-13 medium, containing 10.0 g/L of soy hydrolysate, and sterilized. After sterilization the medium was supplemented with glucose at 20 g/L, 1 M MgSO4 (10 ml/L) and kanamycin at 25 ug/ml. The pH of the medium was adjusted to a pH of 6.8. The vessel aeration was set to 1 vvm and agitation at 350 rpm, temperature was set to 37° C. The fermentor was inoculated from a shake flask culture that has been grown for 16 hours and had an OD of 11.5 at 600 nm. The inoculation level was 5% volume/volume. The dissolved oxygen level was maintained above 30% saturation by increasing agitation speed.

A carbohydrate solution was fed into the fermentor starting at 8 hours EFT. The feed was continued until the end of the fermentation. The feed solution was glucose prepared at 50% w/w %. The feed rate was 9.5 grams of glucose per liter per hour based on the initial starting volume. At 24 hours EFT, IPTG was added to the culture to a concentration of 1 mM. At 50 hours EFT, the fermentation was harvested. The biomass reached 73.3 g dry cell weight (DCW)/L at harvest with a fermentation titer of 12.5 g IL-29/L fermentor broth.

Example 10

Glucose Fed Batch Fermentation+Yeast Extract

ECD880 (IL-29 C172S d2-7)

A shake flask (baffled 500 ml flask with 100 ml medium) was prepared with ZSM medium. Growth was started by inoculating the shake flask with a 0.10 mL of *E. coli* ZGOLD1 containing the expression vector pTAP440 (EE833) from a vial of a research working cell bank. This vector codes for a form of the IL-29 molecule that contains a deletion of the second through seventh amino acids. Growth in the shake flask was at a temperature of 32° C. with the agitation set at 250 rpm. The culture was grown overnight (16 hours) until the $OD_{600}$ was between 8 and 20 units.

A 6 L fermentation vessel was prepared with 3.0 L of PCOL-13 medium, containing 20.0 g/L of yeast extract, and sterilized. After sterilization the medium was supplemented with glucose at 20 g/L, 1 M MgSO$_4$ (10 ml/L) and kanamycin at 25 ug/ml. The pH of the medium was adjusted to a pH of 6.8. The vessel aeration was set to 1 vvm and agitation at 350 rpm, temperature was set to 37° C. The fermentor was inoculated from a shake flask culture that has been grown for 16 hours and had an OD of 8.9 at 600 nm. The inoculation level was 1% volume/volume. The dissolved oxygen level was maintained above 30% saturation by increasing agitation speed.

A carbohydrate solution was fed into the fermentor starting at 8 hours EFT. The feed was continued until the end of the fermentation. The feed solution was glucose prepared at 50% w/w %. The feed rate was 9.5 grams of glucose per liter per hour based on the initial starting volume. At 24 hours EFT, IPTG was added to the culture to a concentration of 1 mM. At 49 hours EFT, the fermentation was harvested. The biomass reached 66.7 g dry cell weight (DCW)/L at harvest with a fermentation titer of 10.4 g IL-29/L fermentor broth.

Example 11

Glucose Fed Batch Fermentation+Yeast Extract Feed

ECD920 (IL-29 C172S d2-7)

A shake flask (baffled 500 ml flask with 100 ml medium) was prepared with ZSM medium. Growth was started by inoculating the shake flask with a 0.10 mL of *E. coli*, ZGOLD1 containing the expression vector pTAP440 (EE833) from a vial of a research working cell bank. This vector codes for a form of the IL-29 molecule that contains a deletion of the second through seventh amino acids. Growth in the shake flask was at a temperature of 32° C. with the agitation set at 250 rpm. The culture was grown overnight (16 hours) until the OD$_{600}$ was between 8 and 20 units.

A 6 L fermentation vessel was prepared and sterilized with 3.0 L of PCOL-18 medium (PCOL-13 medium containing 10.0 g/L of soy peptone). After sterilization the medium was supplemented with glucose at 20 g/L, 1 M MgSO$_4$ (10 mL) and kanamycin at 25 ug/ml. The pH of the medium was adjusted to a pH of 6.8. The vessel aeration was set to 1 vvm and agitation at 350 rpm, temperature was set to 37° C. The fermentor was inoculated from a shake flask culture that has been grown for 16 hours and had an OD of 9.6 at 600 nm. The inoculation level was 1% volume/volume. The dissolved oxygen level was maintained above 30% saturation by increasing agitation speed.

A glucose solution (50% w/w) was fed into the fermentor starting at 8 hours EFT. The feed rate was 9.5 grams of glucose per liter per hour based on the initial starting volume. The feed rate was decreased at 24 hours EFT to 4.75 g glucose/L/hr (starting volume) and a feed of 25% w/w yeast extract solution was also fed into the fermentor at 4.75 g yeast extract/L/hr (starting volume). At 24 hours EFT, IPTG was added to the culture to a concentration of 1 mM. At 48 hours EFT, the fermentation was harvested. The biomass reached 74.8 g dry cell weight (DCW)/L at harvest with a fermentation titer of 10.1 g IL-29/L fermentor broth.

Example 12

Glucose Fed Batch Fermentation+Yeast Extract Feed

ECD 964 (IL-29: D2-7)

A shake flask (baffled 500 ml flask with 100 ml medium) was prepared with ZSM medium. Growth was started by inoculating the shake flask with a 0.10 mL of *E. coli*, ZGOLD5 containing the expression vector pTAP440 (EE867) from a vial of a research working cell bank. This vector codes for a form of the IL-29 molecule that contains a deletion of the second through seventh amino acids. Growth in the shake flask was at a temperature of 32° C. with the agitation set at 250 rpm. The culture was grown overnight (16 hours) until the OD$_{600}$ was between 8 and 20 units.

A 6 L fermentation vessel was prepared and sterilized with 3.0 L of PCOL-18 medium (PCOL-13 medium containing 10.0 g/L of soy peptone). After sterilization the medium was supplemented with glucose at 20 g/L, 1 M MgSO$_4$ (10 ml/L) and kanamycin at 25 ug/ml. The pH of the medium was adjusted to a pH of 6.8. The vessel aeration was set to 1 vvm and agitation at 350 rpm, temperature was set to 37° C. The fermentor was inoculated from a shake flask culture that has been grown for 16 hours. The inoculation level was 1% volume/volume. The dissolved oxygen level was maintained above 30% saturation by increasing agitation speed.

A glucose solution (50% w/w) was fed into the fermentor starting at 8 hours EFT. The feed rate was 9.5 grams of glucose per liter per hour based on the initial starting volume. The feed rate was decreased at 24 hours EFT to 4.75 g glucose/L/hr (starting volume) and a feed of 25% w/w yeast extract solution was also fed into the fermentor at 4.75 g yeast extract/L/hr (starting volume). At 24 hours EFT, IPTG was added to the culture to a concentration of 1 mM. At 48 hours EFT, the fermentation was harvested. The biomass reached 71.1 g dry cell weight (DCW)/L at harvest with a fermentation titer of 9.8 g IL-29/L fermentor broth.

Example 13

Glucose Fed Batch Fermentation+Yeast Extract Feed

ECD 1065 (IL-29 C172S d2-7)

A shake flask (baffled 500 ml flask with 100 ml medium) was prepared with ZSM medium. Growth was started by inoculating the shake flask with a 0.10 mL of *E. coli*, ZGOLD5 containing the expression vector pTAP440 (EE867) from a vial of a research working cell bank. This vector codes for a form of the IL-29 molecule that contains a deletion of the second through seventh amino acids. Growth in the shake flask was at a temperature of 32° C. with the agitation set at 250 rpm. The culture was grown overnight (16 hours) until the OD$_{600}$ was between 8 and 20 units.

A 6 L fermentation vessel was prepared and sterilized with 3.0 L of PCOL-18A medium (PCOL 18 medium containing only 10.0 g/L of glucose). After sterilization the medium was supplemented with glucose at 20 g/L, 1 M MgSO$_4$ (10 ml/L) and kanamycin at 25 ug/ml. The pH of the medium was adjusted to a pH of 6.8. The vessel aeration was set to 1 vvm and agitation at 350 rpm, temperature was set to 37° C. The fermentor was inoculated from a shake flask culture that has been grown for 16 hours and had an OD of 11.8 at 600 nm. The inoculation level was 1% volume/volume. The dissolved oxygen level was maintained above 30% saturation by increasing agitation speed.

A glucose solution (50% w/w) was fed into the fermentor starting at 8 hours EFT. The feed rate was 4.0 grams of glucose per liter per hour based on the initial starting volume from 8-9 hours EFT. AT 9 hours EFT, the feed rate was increased to 8.0 grams of glucose per liter per hour based on the initial starting volume. The feed rate was decreased at 24 hours EFT to 4.0 g glucose/L/hr (starting volume) and a feed of 25% w/w yeast extract solution was also fed into the fermentor at 4.0 g yeast extract/L/hr (starting volume). At 24 hours EFT, IPTG was added to the culture to a concentration of 1 mM. At 47 hours EFT, the fermentation was harvested. The biomass reached 66.9 g dry cell weight (DCW)/L at harvest with a fermentation titer of 9.3 g IL-29/L fermentor broth.

Example 14

Direct Homogenization and Batch Centrifugation of Fermentation Broth

Fermentation broth (0.90 L) from ECD892 (described above) was mixed with 0.90 L of deionized water. The diluted broth mixture was passed through an APV-Gaulin 2000 homogenizer at 10,000 psi. The outlet of the homogenizer was connected with a heat exchanger hooked up to a recirculating water bath set at 2-8° C. The mixture was collected after passing through the homogenizer and was passed through a second time at 10,00 psi. This process was repeated a third and final time. The IL-29 yield in the homogenate was 10.9 g/L fermentor broth for an 87% process yield The homogenate was transferred to 1.0 L Beckman centrifuge bottles, adding 0.90 L of homogenate per bottle. The mixture was then centrifuged for 30 minutes in a Beckman Avanti JHC centrifuge at 15,000×g and 4° C. using a Beckman JLA-8.1 fixed angle rotor.

After centrifuging water was added in an equal volume to the supernatant decanted. The pellet was re-suspend by mixing with a spatula followed by mixing with an Omni EZ hand held homogenizer. The mixture was homogenized using the appropriate sized metal probe at half power for ~15 seconds or until the cell pellet was well suspended. The mixture was then re-centrifuged at 15,000×G using Beckman Avanti JHC centrifuge with the Beckman JLA-8.1 fixed angle rotor for 30 minutes at 4° C. This process was repeated an additional time and the resulting washed inclusion body (WIB) pellet was ready for refolding. The WIB yield was equalized to 9.6 g IL-29 per liter fermentor broth. The step yield from homogenate was 88% and the overall yield from fermentor broth was 76.8%.

Example 15

Direct Homogenization and Continuous Centrifugation of Fermentation Broth

Fermentation broth (80.0 Kg) from ECD967 (IL-29=8.0 g/L) was mixed with 80.0 Kg of deionized water. The diluted broth mixture was passed through a Niro-Sovai homogenizer at 800 bar. The outlet of the homogenizer was connected with a heat exchanger hooked up to chilled water set at 2-8° C. The mixture was collected after passing through the homogenizer and was passed through a second time at the same pressure. This process was repeated a third and final time. The IL-29 yield in the homogenate was 7.24 g/L fermentor broth for a 90% process yield.

The homogenate containing 3% solids (wt/wt) was then centrifuged and washed on a Westfalia C6 disc stack centrifuge. The solution was passed into the centrifuge at 1.5 L/minute with the G force set at 15,000×g. The solids were kept in the bowl, while the supernatant stream was continuously discharged. At a predetermined set point, the homogenate feed was stopped and purified water was passed over the solids at 1.5 L/minute. This water wash displaced supernatant in the bowl. The solids and water in the bowl of the centrifuge were then discharged. The discharged solids (19.81 Kg) contained 17.6% solids (wt/wt) while the supernatant contained approximately 1% solids. The discharged solids were split into 8 containers each containing 2.4 Kg of material.

Example 16

Solubilization of WIB Pellets Using Guanidine Solutions

A WIB pellet was produced from fermentation ECD917 as described in Example 14. The wet weight of the WIB pellet from 2 liters of fermentation broth was approx. 400 g. A 6M Guanidine HCl solution containing 40 mM dithiothreitol was prepared as described in Table 4 below. Three hundred milliliters of this solution was added to the WIB pellet and the pellet was distributed into the solution using a small hand held homogenizer. The solution was allowed to solubilized for 1 hours at room temperature. After solubilization, 700 ml of solute was obtained. This material had an IL-29 content of 19.5 mg/ml and the solute contained 13.65 g of IL-29. This was equivalent to 6.82 g of IL-29 per liter fermentation broth and the process yield was 70%.

TABLE 4

| Guanidine HCl/DTT solution | | |
| --- | --- | --- |
| Component | Formula Weight | Amount/L |
| 2M Tris Stock pH 8.0 | | 50 mL |
| Guanidine HCl | 95.53 g/mol | 573.18 g |
| DTT | 154.25 g/mol | 3.09 g |
| Deionized Water | | QS to 1000 mL |

Example 17

Solubilization of Discharged Solids Using Guanidine Powders

Tris base (11.0 g) and Tris HCl (23.4 g) powders were added to 2.4 Kg of ECD967 discharged solids as described in Example 15. The powders were mixed into solution and the pH adjusted to 8.0. Dithiothreitol (14.8 g) and guanidine HCl (1.37 Kg) were added to the mixture. The solution was allowed to mix for 1 hour without temperature adjustment. After solubilization the mixture weighed 3.78 Kg and contained 55.72 grams IL-29.

Example 18

Refolding of Solubilized WIB Pellets Using Cysteine and Cystine

A 5.0 L glass refold vessel was filled with 3.0 L of 1.1 M Arginine HCl buffer and 0.167 L of 20× salts (see Table 5 below). A stir bar was added to the vessel and the vessel was placed on a stir plate. This unit was then placed into a refrigerated incubator at 8° C. with mixing set at a low speed. To this solution 0.77 g DTT and 0.167 L of 120 mM cystine solution (See Table 6 below) were added. This mixture is used to make a cysteine and cystine redox pair at a ratio of 6:1. The pH was adjusted to 8.0 with NaOH. After preparation, 0.3 L of buffer was removed from the vessel and replaced with 300 ml of the solute solution from ECD917 as described above in Example 16. The 300 ml of solute contained 5.85 g of IL-29 and the starting concentration of unfolded IL-29 was 1.95 mg/mL. The solution was allowed to refold for 6 hours and was stopped by adjusting the pH to 5.5 with 20% acetic acid. The final concentration of refolded was 1.12 mg/mL. The refolding yield was 57% and produced 3.4 g of refolded IL-29.

TABLE 5

1.1M Arginine buffer solution

| Component | Formula Weight | Molarity | Amount [g or mL/L] |
|---|---|---|---|
| 2M Tris stock pH 8.0 | N/A | 0.05M | 27.5 mL |
| Arginine HCl | 210.67 | 1.1M | 231.7 |
| PEG 3400 | 3350 | | 0.55 g |
| Deionized Water | | | QS to 1000 mL |

TABLE 6

120 mM Cystine solution prepared in 0.25M NaOH solution

| Component | Formula Weight | Amount [g or mL/L] |
|---|---|---|
| L-Cystine | 240.3 g | 28.8 g |
| 10M NaOH solution to make 0.25M NaOH | N/A | 25.0 mL |
| Water | | QS to 1000 mL |

Example 19

Refolding of Discharged Solids Using Cysteine and Cystine

Refold buffer containing 1.1 M arginine HCL was prepared as described above in Table 5. Salts solutions (20×) and 120 mM cystine solution were also prepared as described below in Table 7. Arginine buffer (30.0 L) was dispensed into a 50 L jacketed tank with agitation (100 rpm) and cooling set at 8° C. To the arginine buffer solution, 1.67 L of 20 salts and 1.67 L of 120 mM cystine solution were added. Dithiothreitol (7.7 g) was added and the pH was adjusted to pH 8.0 with 10 N NaOH. The solute (3.35 L) prepared in Example 17 was added to the mixture over a 4 hour period. The starting refold concentration of unfolded IL-29 was 1.72 mg/ml. The refold was allowed to proceed for an additional 2 hours before stopping the reaction by adding 20% acetic acid until the pH was lowered to 5.5. The solution was diluted by adding 120 L of 25 mM acetate buffer pH 5.5. The solution was allowed to settle overnight at room temperature. The mixture was filtered using a Cuno BioPlus filter. The IL-29 concentration after refolding was 0.90 mg/mL. The IL-29 concentration in the diluted and clarified solution was 0.19 mg/mL. The overall refolded IL-29 in the clarified broth was 29.85 g for a 54% refolding yield.

TABLE 7

20 X salts solution

| Component | Molarity of Solution |
|---|---|
| 20 X salt stock solution | 0.20M NaCl |
| | 0.04M $MgCl_2$—$6H_2O$ |
| | 0.01M KCl |
| | 0.04M $CaCl_2$—$2H_2O$ |

Example 20

Clarification and Capture of Renatured IL-29

Reducing the pH to 6.0 quenches the IL-29 refolding reaction. The acidified refold is diluted 4.25-fold in 25 mM sodium acetate, pH 5.6 to precipitate misfolded and unfolded proteins and to condition the refold for loading to the capture column. The precipitate is allowed to settle overnight and then the supernatant is clarified through a depth filter train composed of a coarse Cuno Zeta Plus Maximizer 30M03 (nominal 0.8 μm) and fine Cuno Zeta Plus Maximizer 90M05 (nominal 0.2 μm) filter in series.

The clarified, diluted IL-29 is captured on a ToyoPearl SP550C (Tosoh Bioscience) cation exchange column at pH 5.5. In this case, a 14.5 cm tall×14 cm diameter column (2.23 L column volume) is used at 180 cm/hr to capture renatured IL-29 C172S d2-7 originating from 10 L of fermentation broth. The column is equilibrated with 50 mM sodium acetate, pH 5.5, and then loaded with 29 g IL-29 (13 g/L resin). After washing with equilibration buffer, bound IL-29 is eluted with an increasing linear gradient to 2 M sodium chloride, in 50 mM sodium acetate, pH 5.5, over 5 column volumes. Based on absorbance at 280 nm, one pool of eluted material is collected from 0.2 AU to 1.0 AU on the front side of the elution peak. A second pool is collected from 1.0 AU on the front side to 0.2 AU on the trailing edge of the elution peak. The first pool, comprised mostly of non-IL-29 proteins, is discarded. The second pool is carried forward for intermediate purification. Similar methods have been used to capture other IL-29 variants, including the native, the C172S, and the C172S Leu insert forms.

Alternatively, an isocratic salt elution may be used to displace IL-29 from the column. In this example, a 10 cm tall× 1.6 cm diameter column of ToyoPearl SP550C resin is used at 180 cm/hr to capture renatured C172S IL-29 originating from 4 L of fermentation broth. The column is equilibrated with 50 mM sodium acetate, pH 5.5, and then loaded with 136 mg IL-29 (6.8 g/L resin). After washing with equilibration buffer, bound IL-29 is eluted with a 10 CV step at 600 mM NaCl, in 50 mM sodium acetate, pH 5.5. Based on absorbance at 280 nm, material eluted from ~20% of maximal signal on the upslope of the peak to ~20% of the maximal signal on the downslope is pooled and carried forward for intermediate purification. Substantially similar step elution methods have also been used to capture and elute the IL-29 C172 d2-7 variant.

Example 21

Hydrophobic Interaction Chromatography Using Super Butyl 550C Resin

A capture pool containing the IL-29 C172S d2-7 protein was adjusted to 1.0 M $(NH_4)_2SO_4$ by performing a 2-fold dilution with 50 mM sodium acetate, 2.0 M $(NH_4)_2SO_4$, pH 5.5. This solution was passed through a 0.45 μm filter to remove insoluble material. The filtered and conditioned HIC load solution was applied to a ToyoPearl Super Butyl 550C (Tosoh Bioscience) column, previously equilibrated with 50 mM sodium acetate, 1.5 M $(NH_4)_2SO_4$, pH 5.5. Here, a 14 cm tall×14 cm diameter column (2.16 L CV) was operated at 150 cm/hr and at room temperature to purify IL-29 originating from 10 L of fermentation broth (12.4 g IL-29 loaded per liter resin). The HIC column was washed with equilibration buffer to remove unbound material and then IL-29 was eluted with a linear gradient to 50 mM sodium acetate, pH 5.5, over 10 column volumes (CV). Based on absorbance at 280 nm, $\frac{1}{3}^{rd}$ CV fractions were collected from 0.1 AU on the leading edge to 0.1 AU on the trailing edge of the elution peak. Measurements of 280 nm absorbance were collected for each fraction, and the fraction with maximal A280 identified. For pooling, fractions containing at least 20% of the maximal OD280 on the up slope to those containing at least 45% of the maximal OD280 on the down slope are combined.

Example 22

Hydrophobic Interaction Chromatography Using Butyl 650M Resin

A capture pool containing the IL-29 C172S d2-7 protein was adjusted to 1.0 M $(NH_4)_2SO_4$ by performing a 2-fold dilution with 50 mM sodium acetate, 2.0 M $(NH_4)_2SO_4$, pH 5.5. This solution was passed through a 0.45 µm filter to remove insoluble material. The filtered and conditioned HIC load solution was applied to a to a ToyoPearl Butyl 650M (Tosoh Bioscience) column, previously equilibrated with 50 mM sodium acetate, 1.5 M $(NH_4)_2SO_4$, pH 5.5. Here, a 11 cm tall×10 cm diameter column (0.86 L CV) was operated at 150 cm/hr and at room temperature to purify IL-29 originating from 4 L of fermentation broth (8.6 g IL-29 loaded per liter resin). The HIC column was washed with equilibration buffer to remove unbound material and then IL-29 was eluted with a linear gradient to 50 mM sodium acetate, pH 5.5, over 10 column volumes (CV). Substantially similar methods have been used to purify the C172S Leu Insert variants of IL-29 on Butyl 650M resin.

Example 23

Hydrophobic Interaction Chromatography Using Phenyl 650M Resin

A capture pool containing the IL-29 C172S protein was adjusted to 1.0 M $(NH_4)_2SO_4$ by performing a 2-fold dilution with 50 mM sodium acetate, 2.0 M $(NH_4)_2SO_4$, pH 5.5. This solution was passed through a 0.45 µm filter to remove insoluble material. The filtered and conditioned HIC load solution was applied to a ToyoPearl Phenyl 650M (Tosoh Bioscience) column, previously equilibrated with 50 mM sodium acetate, 1.5 M $(NH_4)_2SO_4$, pH 5.5. Here, a 10 cm tall×10 cm diameter column (0.785 L CV) was operated at 150 cm/hr and at room temperature to purify IL-29 originating from 5 L of fermentation broth (7.0 g IL-29 loaded per liter resin). The HIC column was washed with equilibration buffer to remove unbound material and then IL-29 was eluted with a linear gradient to 50 mM sodium acetate, pH 5.5, over 10 column volumes (CV). Substantially similar methods have been used to purify the native IL-29 protein on Phenyl 650M resin.

Example 24

Hydrophobic Interaction Chromatography Using Other HIC Resins

A capture pool containing the native IL-29 protein was adjusted to 1.5 M $(NH_4)_2SO_4$ by performing a 2-fold dilution with 50 mM sodium acetate, 3.0 M $(NH_4)_2SO_4$, pH 5.5. This HIC load solution was passed through a 0.45 µm filter to remove insoluble material. The filtered and conditioned solution was divided and loaded to six separate columns, each previously equilibrated with 50 mM sodium acetate, 1.5 M $(NH_4)_2SO_4$, pH 5.5. Resins tested include: Ether 650M (Tosoh Bioscience), PPG 600M (Tosoh Bioscience), Octyl Sepharose (GE Healthcare), Phenyl Sepharose 6 Fast Flow (low substitution version, GE Healthcare), Butyl Sepharose 4 Fast Flow (GE Healthcare), and Phenyl Sepharose 6 Fast Flow (high substitution version, GE Healthcare). Here, each 8 cm tall×1.6 cm diameter column (16 mL CV) was operated at 150 cm/hr and at room temperature to purify IL-29 at a 5 g IL-29 per liter resin load factor. Each HIC column was washed with equilibration buffer to remove unbound material and then IL-29 was eluted with a linear gradient to 50 mM sodium acetate, pH 5.5, over 10 column volumes (CV).

Example 25

Purification of IL-29 by High Performance Cation Exchange Chromatography

A HIC eluate pool containing the IL-29 C172S d2-7 was diluted 6-fold in water then 0.2 µm filtered and applied to an SP Sepharose HP (GE Healthcare) column, equilibrated in 50 mM sodium acetate, 300 mM sodium chloride, pH 5.5. Here, a 16 cm tall×10 cm diameter column (1.26 L CV) was operated at 125 cm/hr to purify IL-29 after loading to a 15.6 g IL-29 per liter resin load factor. The high performance cation exchange column was washed with equilibration buffer and then eluted with a 20 CV linear gradient to 50 mM sodium acetate, 800 mM sodium chloride, pH 5.5. Based on absorbance at 280 nm, one-third CV fractions were collected from 0.1 AU on the leading edge to 0.1 AU on the trailing edge of the elution peak. Measurements of 280 nm absorbance were collected for each fraction, and the fraction with maximal A280 identified. For pooling, fractions containing at least 80% of the maximal OD280 on the up slope to those containing at least 20% of the maximal OD280 on the down slope were combined. Similar methods have been used to purify the C172S and the C172S Leucine Insert forms of IL-29.

Alternatively, an isocratic salt elution may be used to displace IL-29 from the column. In this example, a 15.8 cm tall×1.6 cm diameter column (31.6 mL CV) of SP Sepharose HP (GE Healthcare) is used at 150 cm/hr to purify IL-29 from diluted and filtered HIC Pool. The column is equilibrated with 50 mM sodium acetate, 300 mM sodium chloride, pH 5.5, and then loaded with 304 mg IL-29 (9.6 g IL-29 per L resin). After washing with equilibration buffer, bound IL-29 is eluted with a 10 CV step at 450 mM NaCl, in 50 mM sodium acetate, pH 5.5.

Example 26

Purification of IL-29 Using Other Cation Exchange Resins

A capture pool containing native IL-29 was diluted in 50 mM sodium acetate, pH 5.5 to a conductivity of <40 mS/cm, then filtered to generate the column load. The filtered and conditioned solution was divided and loaded to two separate columns, each previously equilibrated with 50 mM sodium acetate containing sodium chloride, at pH 5.5. Resins tested include: CM Sepharose Fast Flow (GE Healthcare), and Fractogel $SO_3^-$ (EMD Biosciences). Here, each 8 cm tall×1.6 cm diameter column (16.1 mL CV) was operated at 150 cm/hr and at room temperature to purify IL-29 after column loading at a 5 g IL-29 per liter resin load factor. Each cation exchange column was washed with equilibration buffer to remove unbound material and then IL-29 was eluted with a linear gradient of increasing salt concentration in 50 mM sodium acetate, pH 5.5, over 20 column volumes (CV). For the CM Sepharose column the gradient spanned from 100 to 800 mM sodium chloride, while for the Fractogel resin the gradient was from 400 mM to 2 M sodium chloride.

Example 27

Purification of IL-29 by Hydrophobic Charge Induction Chromatography

A HIC eluate pool containing IL-29 C172S was concentrated and buffer exchanged into 50 mM Tris, 100 mM NaCl, pH 8. The material was applied to a mercaptoethyl pyridine (MEP) HyperCel (BioSepra) column, previously equilibrated with 50 mM Tris, 100 mM NaCl, pH 8. Here, a 6 cm tall×1.1 cm diameter column (5.7 mL CV) was operated at 90 cm/hr to purify IL-29 at an ~10 g IL-29 per liter resin load factor. The MEP HyperCel resin was washed with equilibration buffer at pH 8 then washed with a citrate-phosphate buffer at pH 6.5. Recombinant IL-29 was then eluted from the HCIC resin with a 10 CV linear gradient to citrate-phosphate buffer at pH 4.5.

Example 28

Purification of IL-29 by Immobilized Metal Affinity Chromatography

A capture pool containing the native form of IL-29 was applied to a Chelating Sepharose (GE Healthcare) column previously charged with copper (from cupric sulfate) and equilibrated in 50 mM sodium acetate, 800 mM sodium chloride, pH 5.5. The 8 cm tall×1.6 cm diameter column (16.1 mL CV) was operated at 150 cm/hr to purify IL-29 at an ~5 g IL-29 per liter resin load factor. The copper chelated resin was washed with equilibration buffer, and IL-29 eluted with a 10 CV linear gradient to a buffer containing 25 mM sodium acetate, 800 mM sodium chloride, 500 mM imidazole, pH 5.5. Similar results were obtained when either nickel (from nickel sulfate) or zinc (from zinc chloride) was used as the chelated divalent cation.

Example 29

Concentration of Purified IL-29 Bulk Intermediate

The SPHP pool was concentrated approximately 2-3 fold using a 5 kDa molecular weight cut-off polyether sulfone tangential flow filtration (TFF) plate and frame membrane at a transmembrane pressure of ~20 psi. For the 10 L scale process described here, a membrane surface area of 0.1 m$^2$ and an inlet flow rate of 15 L/hr was used. After the retentate has been concentrated to ~15 mg/mL, it was removed from the TFF system, the system was rinsed with 50 mM sodium acetate, pH 5.5. The rinse was combined with the concentrated retentate to achieve a final ~12.5 mg/mL concentration. This solution is then filtered through a 0.2 μm membrane, then filled in appropriate containers and stored at ≤−60° C. in preparation for the subsequent PEGylation reaction.

Example 30

PEGylation of IL-29 with 20 kDa Linear mPEG-Propionaldehyde

In preparation for a PEGylation reaction, IL-29 bulk intermediate was thawed and transferred to a reaction vessel. Buffer for dilution, 100 mM sodium cyanoborohydride reductant stock solution, and 100 g/L derivatized PEG (20 kDa linear methoxyPEG-propionaldehyde) stock solution, was added to the reaction to create a mixture with 5 g/L IL-29, 10 g/L derivatized PEG (2 PEG per IL-29 on a molar basis), and 20 mM sodium cyanoborohydride at pH 5.5 in 50 mM sodium acetate buffer. In the current example, 16 g of IL-29 bulk intermediate at 13.54 g/L (1.18 L volume) was mixed with 1.06 L of 50 mM sodium acetate, pH 5.5, 0.64 L of 100 mM reductant stock, and 0.32 L of 100 g/L PEG stock to make a 3.2 L volume with the reaction parameters described above. The reaction was allowed to proceed with mixing for ~18 hr at 20° C. under subdued lighting. These reaction conditions resulted in a mixture of 65-75% monoPEGylated IL-29, with 10-20% each of the unPEGylated and multi-PEGylated species, when using the C172S Leucine Insert or C172S d2-7 form of recombinant IL-29 as starting material. Similar results were also obtained when IL-29 at a 3 g/L concentration was reacted with 6 g/L derivatized PEG (2 PEG per IL-29 on a molar basis), and 20 mM sodium cyanoborohydride at pH 5.5 in 50 mM sodium acetate buffer.

Example 31

PEGylation of IL-29 with 30 kDa Linear mPEG-Propionaldehyde

In preparation for a PEGylation reaction, IL-29 bulk intermediate was thawed and transferred to a reaction vessel. Buffer for dilution, 100 mM sodium cyanoborohydride reductant stock solution, and 150 g/L derivatized PEG (30 kDa linear methoxyPEG-propionaldehyde) stock solution, were added to the reaction to create a mixture with 5 g/L IL-29, 15 g/L derivatized PEG (2 PEG per IL-29 on a molar basis), and 20 mM sodium cyanoborohydride at pH 5.5 in 50 mM sodium acetate buffer. In this example, 2.5 mg of IL-29 C172S bulk intermediate at 12.8 g/L (195 μL volume) was mixed with 155 μL of 50 mM sodium acetate, pH 5.5, 100 μL of 100 mM reductant stock, and 50 μL of 150 g/L PEG stock to make a 0.5 mL volume with the reaction parameters described above. The reaction was allowed to proceed with mixing for ~18 hr at 20° C. under subdued lighting. These reaction conditions resulted in a mixture with comparable levels of monoPEGylated IL-29 vs. a 5 g/L IL-29, 2:1 PEG:protein reaction with the 20 kDa version of mPEG-propionaldehyde.

Example 32

PEG-IL-29 Purification by High Performance Cation Exchange Chromatography

After the PEG reaction was completed, the reaction mixture was diluted 2-fold with 50 mM sodium acetate, pH 5.5 then 0.2 μm filtered and loaded to a SP Sepharose HP (GE Healthcare) column, equilibrated in 50 mM sodium acetate, 200 mM sodium chloride, pH 5.5. In this example, a 16 cm tall×10 cm diameter column (1.26 L CV) was operated at 125 μm/hr to purify PEG-IL-29 originating from a PEG reaction using 8 g of IL-29. The high performance cation exchange column was washed with equilibration buffer and then eluted with a 10 CV linear gradient to 50 mM sodium acetate, 500 mM sodium chloride, pH 5.5. Based on absorbance at 280 nm, one-third CV fractions were collected from 0.1 AU on the leading edge to 0.1 AU on the trailing edge of the elution peak. Fractions were analyzed for monoPEG-IL-29 content by reversed phase HPLC, and those fractions containing at least 99% mono-PEGylated IL-29 were pooled. Similar results were obtained regardless of whether the PEG-IL-29 was derived from the C172S Leucine Insert or C172S d2-7 form of the molecule.

PEG-IL-29 may also be eluted from the SP HP column using isocratic methods. In this example, a reaction mixture using IL-29 C172S d2-7 was diluted 2-fold with 50 mM sodium acetate, pH 5.5 then 0.2 μm filtered and loaded to a SP Sepharose HP (GE Healthcare) column, equilibrated in 50 mM sodium acetate, 200 mM sodium chloride, pH 5.5. Here, a 15.5 cm tall×1.6 cm diameter column (31 mL CV) was operated at 125 cm/hr to purify PEG-IL-29 after loading the column at a 9 g IL-29 per liter resin load factor. The high performance cation exchange column was washed with 5 CV equilibration buffer and with a 3CV step at 50 mM sodium acetate, 240 mM sodium chloride, pH 5.5. PEG-IL-29 was then eluted with a 4 CV step at 400 mM sodium chloride, in 50 mM sodium acetate, pH 5.5.

Example 33

Ultrafiltratian/Diafiltration of PEG-IL-29

The SP HP eluate pool containing monoPEGylated IL-29 was concentrated by ultrafiltration in a tangential flow filtration system equipped with a 5 kDa molecular weight cut-off polyether sulfone plate and frame membrane at a trans-membrane pressure of ~20 psi. For a 7.7 g scale process described here, a membrane surface area of 0.1 m² and an inlet flow rate of 15 L/hr was used. After the retentate has been concentrated to ~15-20 mg/mL, it was diafiltered against 7 diavolumes of formulation buffer. The formulated bulk was removed from the TFF system, and the system was rinsed with formulation buffer. The rinse was combined with the concentrated retentate to achieve a final ~12-14 mg/mL concentration. This solution was then filtered through a 0.2 μm membrane, then filled in appropriate containers and stored at ≤−60° C. to generate PEG-IL-29 bulk drug substance.

The complete disclosure of all patents, patent applications, and publications, and electronically available material (e.g., GenBank amino acid and nucleotide sequence submissions) cited herein are incorporated by reference in their entirety. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of producing IL-29 polypeptide comprising:
   (a) providing an *E. coli* host cell comprising an expression vector comprising the following operably linked elements:
      (i) a translational enhancer comprising SEQ ID NO:13; and
      (ii) a nucleic acid molecule encoding an IL-29 polypeptide comprising an amino acid sequence having at least 95% identity to SEQ ID NO:6;
   (b) culturing the *E. coli* host cell in a growth medium in a fermentation vessel;
   (c) harvesting the *E. coli* host cell; and
   (d) isolating the IL-29 polypeptide from the *E. coli* host cell.

2. The method of claim 1, wherein the *E. coli* host cell is ompT deficient.

3. The method of claim 2, wherein the *E. coli* host cell is fhuA deficient.

4. The method of claim 1, wherein the nucleic acid molecule encodes an IL-29 polypeptide comprising an amino acid sequence that is at least 98% identical to SEQ ID NO:6.

5. The method of claim 1, wherein the nucleic acid molecule encodes an IL-29 polypeptide comprising SEQ ID NO:6.

6. The method of claim 1, wherein the growth medium in the fermentation vessel has a pH ranging from 6.2 to 7.2.

7. The method of claim 1, further comprising feeding a carbohydrate feed solution into the fermentation vessel.

8. The method of claim 7, wherein the carbohydrate feed solution comprises a glycerol or glucose at a concentration ranging from 10 to 30 g/L growth medium.

9. The method of claim 7, wherein the carbohydrate feed solution is fed at a feed rate of 5-15 grams of glycerol or glucose per liter per hour.

10. The method of claim 7, wherein the carbohydrate feed solution is fed into the fermentation vessel at 6 to 8 hours elapsed fermentation time.

11. The method of claim 1, further comprising adding an inducing agent to the fermentation vessel.

12. The method of claim 11, wherein the inducing agent is isopropyl thiogalactopyranoside.

13. The method of claim 12, wherein isopropyl thiogalactopyranoside is added to the culture at a concentration ranging from 0.5 mM to 2 mM.

14. The method of claim 11, wherein the inducing agent is added at 20 to 30 hours elapsed fermentation time.

15. The method of claim 1, wherein the *E. coli* host cell is harvested at 48-56 hours elapsed fermentation time.

16. The method of claim 3, wherein the *E. coli* host cell is ZGOLD5.

17. A method of producing IL-29 polypeptide comprising:
   (a) providing an ompT deficient and fhuA deficient *E. coli* host cell comprising an expression vector comprising the following operably linked elements:
      (i) a translational enhancer comprising SEQ ID NO:13; and
      (ii) a nucleic acid molecule encoding an IL-29 polypeptide comprising SEQ ID NO:6;
   (b) culturing the *E. coli* host cell in a growth medium in a fermentation vessel;
   (c) harvesting the *E. coli* host cell; and
   (d) isolating the IL-29 polypeptide from the *E. coli* host cell.

18. An *E. coli* expression vector comprising the following operably linked elements:
   (i) a translational enhancer comprising SEQ ID NO:13; and
   (ii) a nucleic acid molecule encoding an IL-29 polypeptide comprising an amino acid sequence having at least 95% identity to SEQ ID NO:6.

19. The *E. coli* expression vector of claim 18, wherein the nucleic acid molecule encodes an IL-29 polypeptide comprising an amino acid sequence that is at least 98% identical to SEQ ID NO:6.

20. The *E. coli* expression vector of claim 18, wherein the nucleic acid molecule encodes an IL-29 polypeptide comprising SEQ ID NO:6.

\* \* \* \* \*